(12) United States Patent
Zhu et al.

(10) Patent No.: US 11,371,027 B2
(45) Date of Patent: Jun. 28, 2022

(54) MIRROR NUCLEIC ACID REPLICATION SYSTEM

(71) Applicant: Tsinghua University, Beijing (CN)

(72) Inventors: Ting Zhu, Beijing (CN); Lei Liu, Beijing (CN); Weiliang Xu, Beijing (CN); Zimou Wang, Beijing (CN); Wenjun Jiang, Beijing (CN); Jiaxing Wang, Beijing (CN); Linping Yu, Beijing (CN)

(73) Assignee: Tsinghua University, Beijing (CN)

( * ) Notice: Subject to any disclaimer, the term of this patent is extended or adjusted under 35 U.S.C. 154(b) by 194 days.

(21) Appl. No.: 16/092,757

(22) PCT Filed: Feb. 15, 2017

(86) PCT No.: PCT/CN2017/073573
§ 371 (c)(1),
(2) Date: Oct. 10, 2018

(87) PCT Pub. No.: WO2017/177759
PCT Pub. Date: Oct. 19, 2017

(65) Prior Publication Data
US 2019/0376050 A1   Dec. 12, 2019

(51) Int. Cl.
*C12N 9/12* (2006.01)
*C12N 15/10* (2006.01)

(52) U.S. Cl.
CPC ......... *C12N 9/1252* (2013.01); *C12N 15/10* (2013.01); *C12N 15/1068* (2013.01); *C12Y 207/07007* (2013.01)

(58) Field of Classification Search
CPC .. C12N 9/1252; C12N 15/10; C12N 15/1068; C12Y 207/07007
See application file for complete search history.

(56) References Cited

U.S. PATENT DOCUMENTS

| 2011/0229976 A1 | 9/2011 | Turner et al. |
| 2012/0167988 A1* | 7/2012 | Wang ............... B01L 3/50273 137/1 |

FOREIGN PATENT DOCUMENTS

| CN | 101818142 | 9/2010 |
| CN | 102517241 | 6/2012 |
| CN | 104379748 | 2/2015 |
| WO | WO 2013/170963 | 11/2013 |
| WO | WO 2017/028548 | 2/2017 |
| WO | WO 2017/177759 | 10/2017 |
| WO | WO 2015/074756 | 5/2020 |

OTHER PUBLICATIONS

Leva et al. (Chemistry & Biology, 2002, vol. 9, pp. 351-359) (Year: 2002).*
International Preliminary Report on Patentability dated Oct. 16, 2018 From the International Bureau of WIPO Re. Application No. PCT/CN2017/073573 and Its Translation Into English. (12 Pages).

(Continued)

*Primary Examiner* — Jeremy C Flinders

(57) ABSTRACT

Provided is a method for replicating a mirror nucleic acid, comprising: reacting a mirror nucleic acid template, a mirror nucleic acid primer and mirror dNTPs/rNTPs in the presence of a mirror nucleic acid polymerase, so as to obtain the mirror nucleic acid.

10 Claims, 29 Drawing Sheets

Specification includes a Sequence Listing.

(56) References Cited

OTHER PUBLICATIONS

International Search Report and the Written Opinion dated May 4, 2017 From the International Searching Authority Re. Application No. PCT/CN2017/073573 and Its Translation Into English. (18 Pages).
Notification of Office Action and Search Report dated Apr. 3, 2019 From the State Intellectual Property Office of the People's Republic of China Re. Application No. 201780026142.7 and Translation of Office Action Into English. (2 Pages).
Notification of Office Action and Search Report dated Jan. 4, 2019 From the State Intellectual Property Office of the People's Republic of China Re. Application No. 201780026142.7 and Translation of Office Action Into English. (4 Pages).
Notification of Office Action and Search Report dated Nov. 9, 2018 From the State Intellectual Property Office of the People's Republic of China Re. Application No. 201780026142.7 and Translation of Office Action Into English. (2 Pages).
Notification of Office Action and Search Report dated Jan. 17, 2019 From the State Intellectual Property Office of the People's Republic of China Re. Application No. 201780026142.7 and Translation of Office Action Into English. (2 Pages).
Supplementary European Search Report and the European Search Opinion dated Aug. 2, 2019 From the European Patent Office Re. Application No. 17781735.0. (7 Pages).
Jiang et al. "Mirror-Image Polymerase Chain Reaction", Cell Discovery, XP55608092, 3(17037): 7 P., Oct. 17, 2017.
Pech et al. "A Thermostable D-Polymerase for Mirror-Image Pcr", XP55608084, Nucleic Acids Research,45(7): 3997-4005, Feb. 2, 2017.
International Preliminary Report on Patentability dated Feb. 20, 2018 From the International Bureau of WIPO Re. Application No. PCT/CN2016/079006. (6 Pages).
International Search Report and the Written Opinion dated Jul. 15, 2016 From the International Searching Authority Re. Application No. PCT/CN2016/079006 and Its Translation Into English. (23 Pages).

Boudsocq et al. "Sulfolobus Solfataricus P2 DNA Polymerase IV (Dpo4): An Archaeal DinB-Like DNA Polymerase With Lesion-Bypass Properties Akin to Eukaryotic PolEta", Nucleic Acids Research, 29(22): 4607-4616, Nov. 15, 2001.
Brewster et al. "Left-Handed Comments", Science, New Series, 258(5086): 1289-1290, Nov. 20, 1992.
Church "Fabricating With DNA", 4th Fab Lab Forum & Digital Fabrication Symposium, Chicago, ILL., USA, Aug. 20-25, 2007, Slide Show, 22 P., Aug. 22, 2007.
Church "George Church—Life: What A Concept!", Edge Foundation, Conversation, 14 P., Aug. 12, 2018.
Oliveros et al. "Characterization of An African Swine Fever Virus 20-kDa DNA Polymerase Involved in DNA Repair", The Journal of Biological Chemistry, 272(49): 30899-30910, Dec. 5, 1997.
Wang et al. "Synthesis of New Chiral Compounds of Purine and Pyrimidine", Science in China Series B-Chemistry, 28(6): 531-539, Dec. 20, 1998 & English Abstract.
Zimou Wang, et al., A synthetic molecular system capable of mirror-image genetic replication and transcription, Nature Chemistry, Jul. 2016, vol. 8, 698-704.
Matthew T. Weinstock, et al., Synthesis and folding of a mirror-image enzyme reveals ambidextrous chaperone activity, PNAS, Aug. 12, 2014, vol. 111, No. 32, 11679-11684.
O174L DNA polymerase beta-like protein [ African swine fever virus ], Aug. 15, 2018, https://www.ncbi.nlm.nih.gov/gene/?term=NP_042790, 3 pages.
Communication Pursuant to Article 94(3) EPC Dated Aug. 20, 2020 From the European Patent Office Re. Application No. 17781735.0. (7 Pages).
Xu et al. "Total Chemical Synthesis of a Thermostable Enzyme Capable of Polymerase Chain Reaction", Cell Discovery, 3(1): 17008-1-17008-10, Published Online Feb. 28, 2017.
Communication Pursuant to Article 94(3) EPC Dated Jun. 24, 2021 From the European Patent Office Re. Application No. 17781735.0. (3 Pages).
Notification of Office Action and Search Report dated Dec. 1, 2021 From the State Intellectual Property Office of the People's Republic of China Re. Application No. 201780026142.7. (27 Pages).

* cited by examiner a

```
         10          20          30          40          50          60
MIVLFVDFDY FYAQVEEVLN PSLKGKPVVV CVFSGRFEDS GAVATANYEA RKFGVKAGIP
         70          80          90         100         110         120
IVEAKKILPN AVYLPMRKEV YQQVSSRIMN LLREYSEKIE IASIDEAYLD ISDKVRDYRE
        130         140         150         160         170         180
AYNLGLEIKN KILEKEKITV TVGISKNKVF AKIAADMAKP NGIKVIDDEE VKRLIRELDI
        190         200         210         220         230         240
ADVPGIGNIT AEKLKKLGIN KLVDTLSIEF DKLKGMIGEA KAKYLISLAR DEYNEPIRTR
        250         260         270         280         290         300
VRKSIGRIVT MKRNSRNLEE IKPYLFRAIE ESYYKLDKRI PKAIHVVAVT EDLDIVSRGR
        310         320         330         340         350
TFPHGISKET AYSESVKLLQ KILEEDERKI RRIGVRFSKF IEAIGLDKFF DT
                              WT Dpo4
``` b

```
              10          20          30          40          50          60
(His6)(Nle)VLFVDFDY FYAQVEEVLN PSLKGKPVVV (S)VFSGRFEDS GAVATANYEA RKFGVKAGIP
         70          80          90         100         110         120
IVEAKKILPN AVYLP(Nle)RKEV YQQVS(A)RI(Nle)N LLREYSEKIE IASIDEAYLD ISDKVRDYRE
        130         140         150         160         170         180
AY(A)LGLEIKN KILEKEKITV TVGISKNKVF AKIAAD(Nle)AKP NGIKVIDDEE VKRLIRELDI
        190         200         210         220         230         240
ADVPGIGNIT AEKLKKLGIN KLVDTL(A)EF DKLKG(Nle)GEA KAKYLISLAR DEYNEPIRTR
        250         260         270         280         290         300
VRKSIGRIVT (Nle)KRNSRNLEE IKPYLFRAIE ESYYKLDKRI PKAIHVVAVT EDLDIVSRGR
        310         320         330         340         350
TFPHGISKET AY(A)ESVKLLQ KILEEDERKI RRIGVRFSKF IEAIGLDKFF DT
                          Synthetic Dpo4-5m
```

FIG. 14

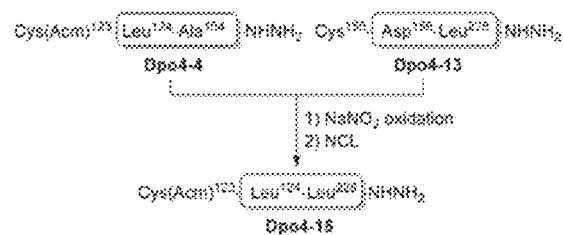
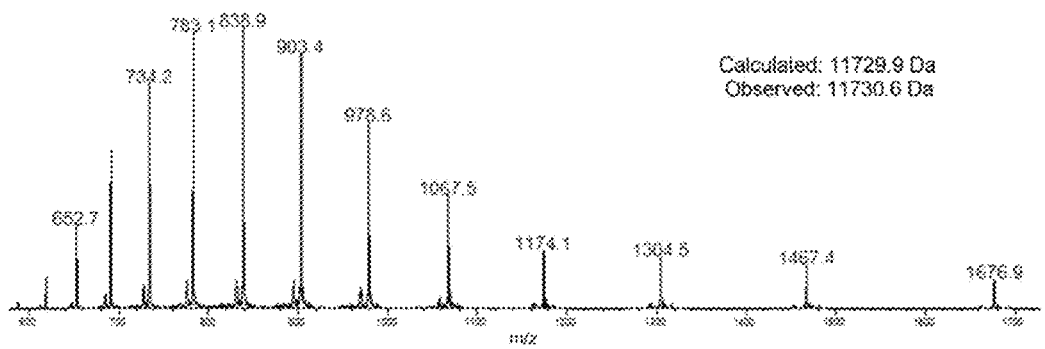
FIG. 24

MIRROR NUCLEIC ACID REPLICATION SYSTEM

CROSS REFERENCE TO RELATED APPLICATIONS

This application is the U.S. National Stage of International Patent Application No. PCT/CN2017/073573, filed Feb. 15, 2017, and PCT/CN2016/079006, filed Apr. 11, 2016, entitled "MIRROR NUCLEIC ACID REPLICATION SYSTEM", and the contents of which are herein incorporated by reference in their entirety.

FIELD OF THE INVENTION

The present invention relates to the field of genetic engineering, and more particularly to the replication and transcription of a mirror-image nucleic acid.

BACKGROUND OF THE INVENTION

Chirality is a basic property of some molecules in three-dimensional space, that is, an object cannot coincide with its image in the mirror. Like the left and right hands of a person, the two are in a relationship of an object and its mirror-image and cannot overlap regardless of how they are flipped in three-dimensional space. This is the chirality of an object in space. A mirror-image of a molecule is called its enantiomer. They have the same physical and chemical properties, and have the same melting point, molecular weight, solubility, density, and NMR spectrum. The mutually different nature of the enantiomers is their optical property—rotating the direction of a plane polzaried light. Chirality widely exists in nature. Biomacromolecules in living organisms such as proteins, polysaccharides, DNA and RNA are chiral. For all organisms on the earth, whether large plants, mammals or microorganisms that are invisible to the naked eye, among the 20 amino acids that constitute the protein, except for the fact that glycine has no chirality, the other 19 amino acids are all in L-form; while for DNA and RNA carrying genetic information, their riboses are all in D-form.

The amino acid has a chiral carbon atom in the immediate vicinity of the carboxyl group. As a chiral center, it makes the amino acids other than glycine have both L and D chirality. L refers to levorotatory or left-handed, and D refers to dextrorotatory or right-handed. For nucleic acids, D-form is the chirality found in nature, and the chiral center of a nucleic acid molecule is located on its backbone.

The biological activities of two compounds with different chirality in a living organism may be completely different. Enzymes and cell surface receptors in biological individuals are mostly chiral, and the two enantiomers are often absorbed, activated and degraded in different ways in the organism. For a common chiral drug, either the two enantiomers may have equivalent pharmacological activities, or one may be active, but the other may be inactive, even toxic. At present, it is believed that the molecules of proteins and nucleic acids present in living organisms have the characteristics of chiral unitarity. If a native protein sequence is incorporated with a mirror-image amino acid, its own secondary structure will be destroyed (Krause et al., 2000), and its protein function will be severely affected.

In early environment of the earth, there should be the presence of biomolecules such as amino acids and nucleic acids before the most primitive cells appeared. Although the theory of RNA as the origin of living matter is well-established, there is currently no evidence of which of the amino acid and nucleic acid first appeared on the earth. The study of the meteorite of Murchison, which fell in Australia in 1969, found that it contained a variety of amino acids, including glycine, alanine and glutamic acid. The two kinds of chiral amino acids were not 1:1, and the L-amino acid was more than the D-amino acid (Engel and Macko, 2001). Experiments by Breslow and Levine showed that even with small chiral difference, it was possible to retain more than 90% of a chiral amino acid in solution after two times of evaporation and crystallization of the solution (Breslow and Levine, 2006), and this process could occur in the early environment of the earth. In addition, there are other hypotheses that the chiral unitarity in evolution was derived from the optically active crystal generated by calcite that selectively adsorbed an optically active amino acid, increasing the proportion of the other in solution. In addition to the above two explanations, the current RNA origin of life hypothesis believes that RNA was formed by organic molecules in the early environment of the earth, and RNA had evolved into a biologically functional RNA, an RNA ribozyme, which had activity such as self-replication and self-cleavage; in further evolution, proteases or peptides composed of amino acids began to participate in catalyzing the replication, unwinding, and the like of RNA, and there might be a process of undergoing chiral selection during this stage, which led to the chiral unitarity in the complex living organisms that finally evolved.

SUMMARY OF THE INVENTION

In this study, we constructed a genetic information transcription and replication system based on D-ASFV pol X mirror-image polymerase by chemical synthesis, and realized two steps in the mirror-image center rule: replication of L-DNA and transcription into L-RNA. We confirmed that the replication and transcription of mirror-image DNA followed the base complementary pairing rules and have good chiral specificity. We found that when the natural and mirror-image DNA replication systems were placed in the same solution system, the two could work separately without serious mutual interference. The mirror-image polymerase system amplifies the L-DNAzyme deoxyribozyme sequence to achieve self-splicing activity corresponding to the native deoxyribozyme. The realization of mirror-image genetic information replication and transcription illustrates the potential for existence and biological activity of mirror-image life molecules, and also lays the foundation for the future construction of mirror-image cells in the laboratory environment. After further optimization of the system, the mirror-image replication system will also be used for efficient screening of a mirror-image nucleic acid drug by a biological method.

The present invention provides a method for replicating a mirror-image nucleic acid comprising: carrying out a reaction in the presence of a mirror-image nucleic acid polymerase, a mirror-image nucleic acid template, a mirror-image nucleic acid primer, and mirror-image dNTPs/rNTPs to obtain the mirror-image nucleic acid.

The present invention provides a method for performing mirror-image PCR, comprising: carrying out a reaction in the presence of a mirror-image nucleic acid polymerase, a mirror-image nucleic acid template, a mirror-image nucleic acid primer, and mirror-image dNTPs/rNTPs to obtain a mirror-image nucleic acid.

The present invention provides a method for screening a mirror-image nucleic acid molecule comprising: contacting a library of random mirror-image nucleic acid sequences with a target molecule under a condition that allows binding of the two; obtaining a mirror-image nucleic acid molecule that binds to the target molecule; and amplifying the mirror-image nucleic acid molecule that binds to the target molecule by mirror-image PCR.

The present invention also provides D-ASFV pol X, the sequence of which is set forth in SEQ ID NO: 17, wherein except for glycine which is not chiral, all other amino acids are D-form amino acids.

BRIEF DESCRIPTION OF THE DRAWINGS

FIG. 14 illustrates the total chemical synthesis design of mutant Dpo4 polymerase. (a) The amino acid sequence of wild-type Dpo4 polymerase (SEQ ID NO: 45); (b) The amino acid sequence of His6-tagged mutant Dpo4 polymerase (Dpo4-5m) corresponding to SEQ ID Nos: 46 and 47, wherein the highlighted amino acid sites were the four mutations introduced in order to increase the number of peptide ligation sites (S86A, N123A, 5207A and S313A), and a mutation site (C31S) introduced to prevent intramolecular dimerization caused by disulfide bond formation during folding, respectively. Furthermore, all methionines in the peptide chain were replaced with norleucine (Met1, Met76, Met89, Met157, Met216 and Met251) to prevent oxidation during solid phase peptide synthesis and peptide ligation. The colors of the nine peptide sgements in this figure correspond to the colors used in the peptide segments (Dpo4-1 to Dpo4-9) in FIG. 2.

1000 bp was extended for 10 minutes. The expected length of the amplicon is indicated above the lane and a primer dimer band can be seen below the main product band. The W/o template indicates a negative control without a template, and the reaction only had primer, enzyme and other PCR components. NC (110 bp)/NC (1 kb) indicates a negative control without enzyme addition, and the reaction only had primer, template (110 bp/1 kb) and other PCR components. (b) The synthesized Dpo4-5m polymerase was used to PCR amplify a 1.1 kb dpo4 gene, with 35 cycles per reaction, and the extension time in each cycle was set to 10 minutes. (c) The synthesized Dpo4-5m polymerase was used to PCR amplify the 120 kb 5S rRNA gene rrfB in *E. coli*, with 35 cycles per reaction, and the extension time in each cycle was set to 2 minutes. (d) The synthesized Dpo4-5m polymerase was used to PCR amplify the 1.5 kb 16S rRNA gene rrfC in *E. coli*, with 35 cycles per reaction, and the extension time in each cycle was set to 15 minutes. A primer dimer may be observed under the main product band. All PCR products were analyzed by 2% agarose gel electrophoresis and stained with GoldView. The expected amplicon length is indicated above the lane, NC represents the negative control without enzyme addition, and only the primer and template and other PCR components were present in the reaction, and M was a standard molecular weight DNA marker.

Figure 18:
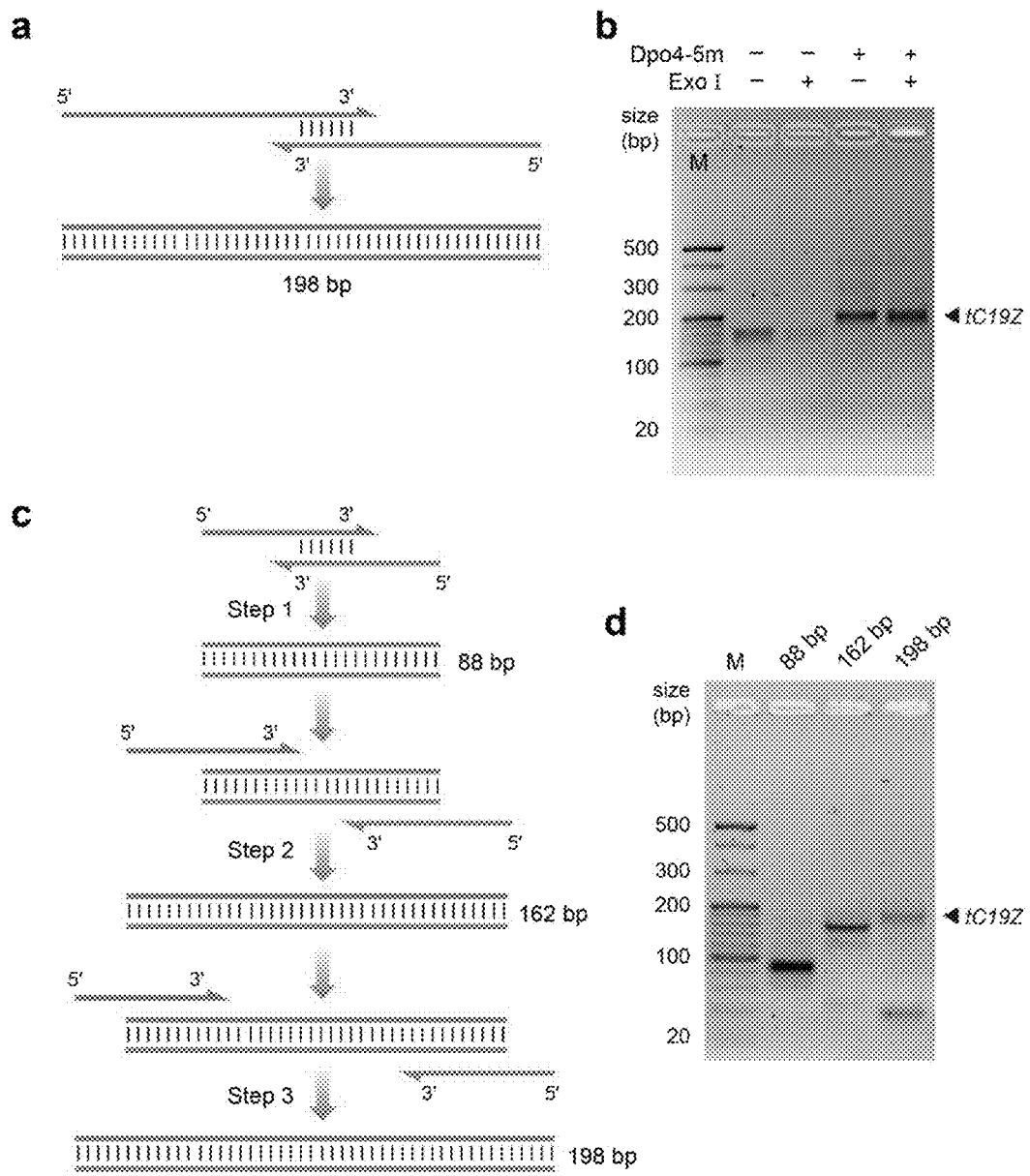

FIG. 18 illustrates the assembly PCR using the synthetic Dpo4-5m polymerase. (a, b) The PCR was carried out by two long primers (tC19Z-F115 and tC19Z-R113) sharing a 30 bp overlap region. The amplified target product was 198 bp tC19Z gene, and the reaction was carried out for 20 cycles. The PCR product was analyzed by 3% high resolution agarose gel electrophoresis and stained with GoldView (Solarbio). Exo I indicates treatment with exonuclease I, which digests only single-stranded DNA without digesting double-stranded DNA. (c, d) Three-step PCR reactions were performed with six short primers ranging in lengths from 47 nt to 59 nt, and the 198 bp long tC19Z gene was assembled. The PCR product was analyzed by 3% high resolution agarose gel electrophoresis and stained with GoldView (Solarbio). The numbers of cycles of the first, second, and third step of the PCR reaction were 5, 10, and 20, respectively. The sequence lengths expected to be amplified in each of the three steps of the PCR reactions were 88 bp, 162 bp, and 198 bp, respectively (labeled above the lane). A primer dimer may be observed under the main product band and M was a standard molecular weight DNA marker.

Figure 19:
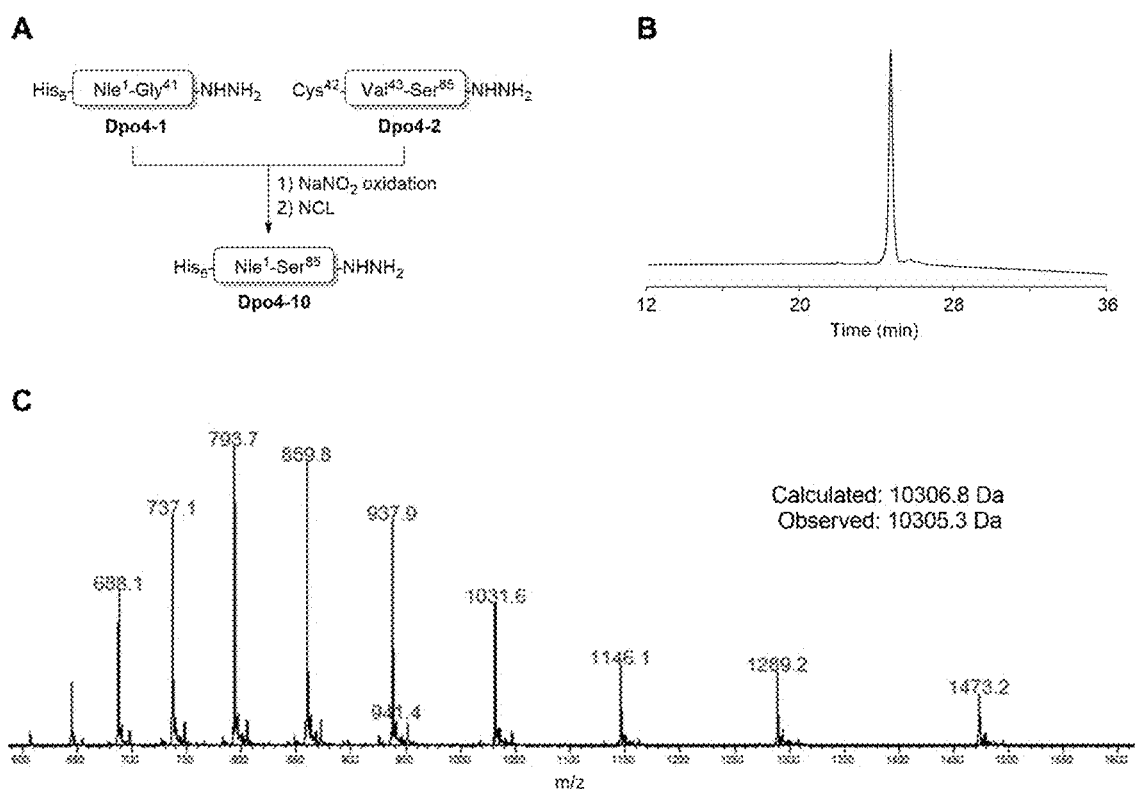

FIG. 19 illustrates the preparation of Dpo4-10. (A) 54 mg of Dpo4-1 was dissolved in 2 ml of an acidified ligation buffer (6 M Gn.HCl and 0.1 M $NaH_2PO_4$ in water, pH 3.0). The mixture was placed in an ice salt bath and cooled, then 200 µl of an acidified ligation buffer containing 0.5 M $NaNO_2$ was added, and after stirring for 30 minutes in an ice salt bath, 2 ml of 0.2 M MPAA (dissolved in 6 M Gn.HCl and 0.1 M $Na_2HPO_4$, pH 6.0) was added. Then 49 mg of Dpo4-2 was added and the pH of the solution was adjusted to 6.5 with sodium hydroxide solution at room temperature. After 15 hours of reaction, reduction with tris(2-carboxyethyl)phosphine followed by HPLC purification gave 52 mg of Dpo4-10 with a yield of 51%; (B) Analytical high performance liquid chromatogram of Dpo4-10 ($\lambda$=214 nm), column: Welch C4; gradient: mobile phase ratio $CH_3CN$:$H_2O$ from 20% to 70% (both with 0.1% TFA), elution for more than 30 minutes; (C) Electrospray ionization mass spectrum of Dpo4-10.

Figure 20:
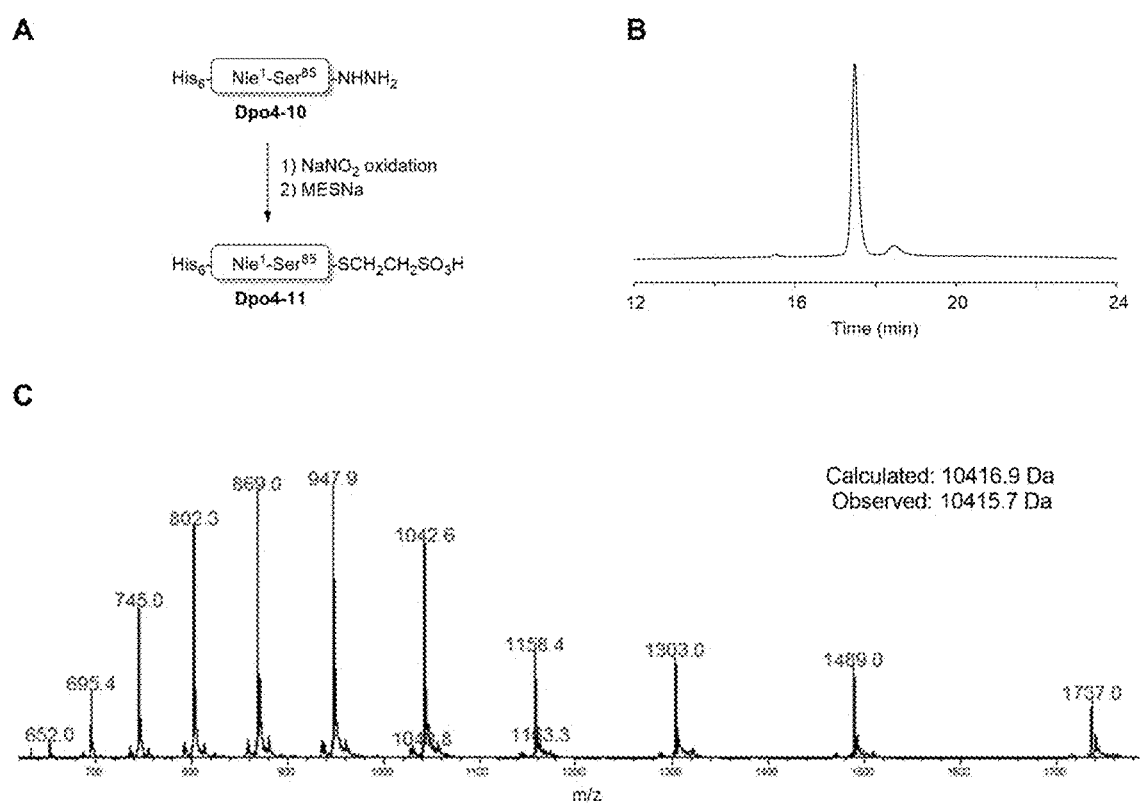

FIG. 20 illustrates the preparation of Dpo4-11. (A) 43 mg of Dpo4-10 was dissolved in 2 ml of an acidified ligation buffer (6 M Gn.HCl and 0.1 M $NaH_2PO_4$ in water, pH 3.0). The mixture was placed in an ice salt bath and cooled, then 160 µl of an acidified ligation buffer containing 0.5 M $NaNO_2$ was added, and the system was stirred in an ice salt bath for 25 minutes, and then 24 mg of sodium sulfonate (MESNa) was added. The pH of the solution was adjusted to 5.1 with sodium hydroxide solution at room temperature. After 1 hour of reaction, the reaction product was purified by HPLC to finally give 25 mg of Dpo 4-11 with a yield of 60%. (B) Analytical high performance liquid chromatogram of Dpo4-11 ($\lambda$=214 nm), column: Welch C4; gradient: mobile phase ratio $CH_3CN$:$H_2O$ from 20% to 100% (both with 0.1% TFA), elution for more than 30 minutes; (C) Electrospray ionization mass spectrum of Dpo4-11.

Figure 21:
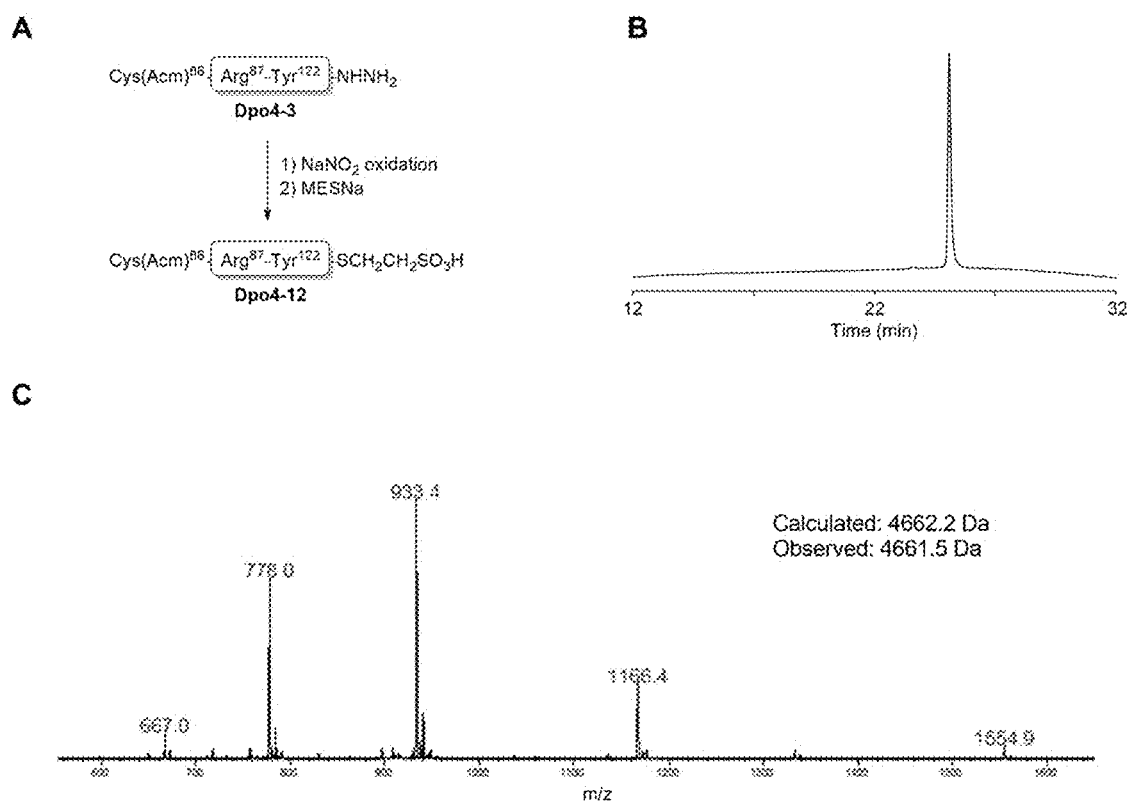

FIG. 21 illustrates the preparation of Dpo4-12. (A) 45 mg of Dpo4-3 was dissolved in 4 ml of an acidified ligation buffer (6 M Gn.HCl and 0.1 M $NaH_2PO_4$ in water, pH 3.0). The mixture was placed in an ice salt bath and cooled, then 200 µl of an acidified ligation buffer containing 0.5 M $NaNO_2$ was added and stirred in an ice salt bath for 25 minutes, then 1 ml of an acidified ligation buffer containing 0.4 M sodium sulfonate (MESNa) was added. The pH of the solution was adjusted to 5.1 with sodium hydroxide solution at room temperature. After 1 hour of reaction, the product was purified by HPLC to finally give 19 mg of Dpo4-12 with a yield of 41%; (B) Analytical high performance liquid chromatogram of Dpo4-12 ($\lambda$=214 nm), column: Welch C4; gradient: mobile phase ratio $CH_3CN$:$H_2O$ from 20% to 70% (both with 0.1% TFA), elution for more than 30 minutes; (C) Electrospray ionization mass spectrum of Dpo4-12.

Figure 22:
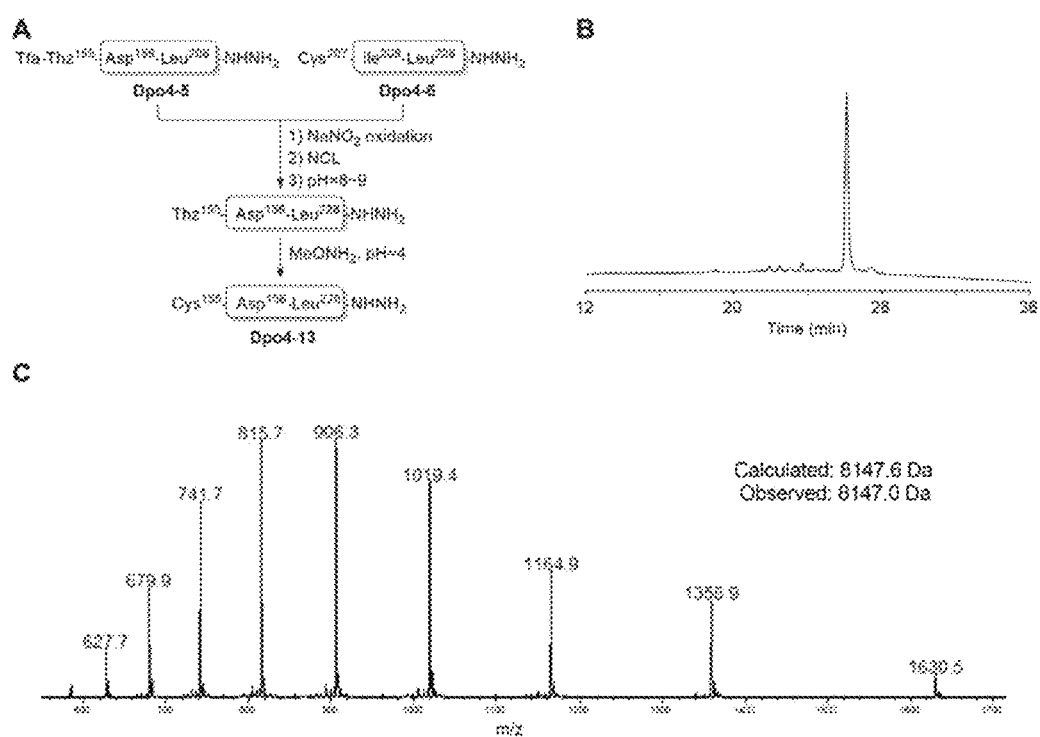

FIG. 22 illustrates the preparation of Dpo4-13. (A) 70 mg of Dpo4-5 was dissolved in 2.4 ml of an acidified ligation buffer (6 M Gn.HCl and 0.1 M $NaH_2PO_4$ in water, pH 2.9). The mixture was placed in an ice salt bath and cooled, then 240 µl of an acidified ligation buffer containing 0.5 M $NaNO_2$ was added and stirred in an ice salt bath for about 30 minutes, then 2.4 ml of 0.2 M MPAA (dissolved in 6 M Gn.HCl and 0.1 M $Na_2HPO_4$, pH 4.9) was added. The pH of the solution was adjusted to 5.4 with sodium hydroxide solution at room temperature, and after addition of 36 mg of Dpo4-6, the pH of the solution was again adjusted to 6.6. After 11 hours of reaction, the product was analyzed and the pH was adjusted to 9.0 to completely remove the Tfa group. The product was analyzed again after about 1 hour, and then 72 mg of $MeONH_2$.HCl was added to achieve conversion of Thz to Cys, and the pH of the reaction system was adjusted to 4.0 by the addition of TCEP.HCl. After about 3 hours, the product was analyzed and purified by HPLC to give 56 mg of Dpo 4-13 with a yield of 57%. (B) Analytical high performance liquid chromatogram of Dpo4-13 ($\lambda$=214 nm), column: Welch C4; gradient: mobile phase ratio $CH_3CN$:$H_2O$ from 20% to 70% (both with 0.1% TFA), elution for more than 30 minutes; (C) Electrospray ionization mass spectrum of Dpo4-13.

Figure 23:
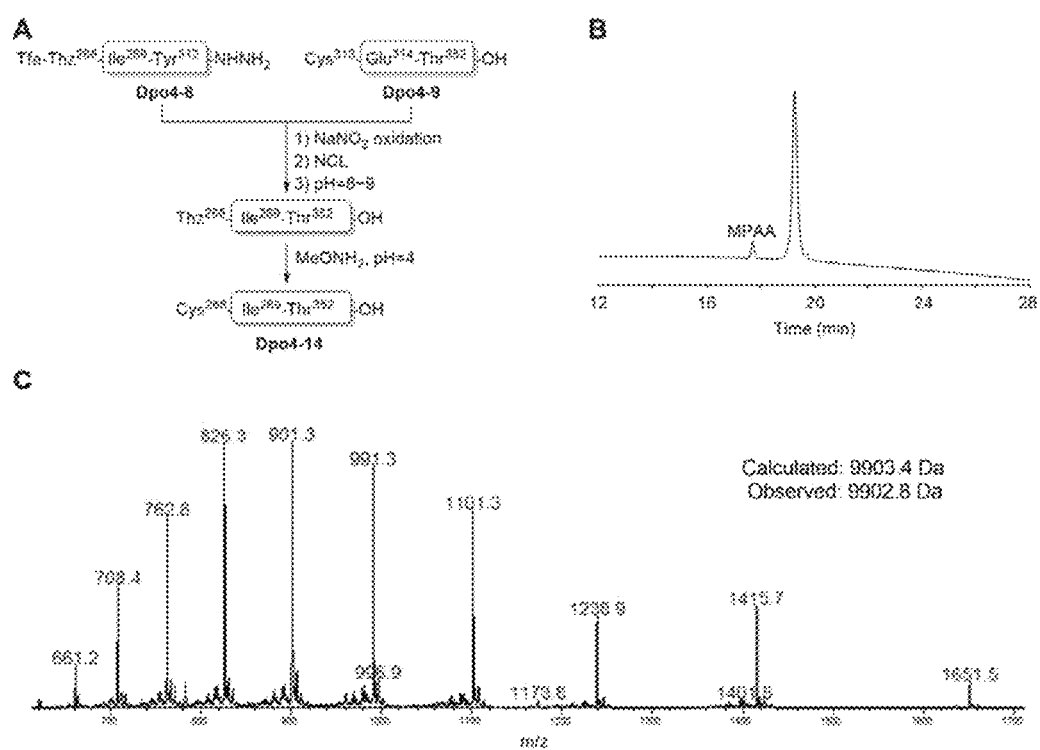

FIG. 23 illustrates the preparation of Dpo4-14. (A) The ligation reaction of Dpo4-8 (53 mg) and Dpo4-9 (48 mg) was similar to that of Dpo4-5 and Dpo4-6, see FIG. 22. Finally, 46 mg of Dpo4-13 was obtained with a yield of 46%; (B) Analytical high performance liquid chromatogram of Dpo4-14 ($\lambda$=214 nm); column: Welch C4; gradient: mobile phase ratio $CH_3CN$:$H_2O$ from 20% to 100% (both with 0.1% TFA), elution for more than 30 minutes; (C) Electrospray ionization mass spectrum of Dpo4-14.

FIG. 24 illustrates the preparation of Dpo4-15. (A) 36 mg of Dpo4-4 was dissolved in 2 ml of an acidified ligation buffer (6 M Gn.HCl and 0.1 M $NaH_2PO_4$ in water, pH 3.0). The mixture was placed in an ice salt bath and cooled, then 400 μl of an acidified ligation buffer containing 0.5 M NaNO$_2$ was added, and stirred in an ice salt bath for 30 minutes, then 2 ml of 0.2 M MPAA (dissolved in 6 M Gn.HCl and 0.1 M Na$_2$HPO$_4$, pH 6.0) was added. After addition of 81 mg of Dpo4-13, the pH of the solution was adjusted to 6.5 with sodium hydroxide solution at room temperature. After 15 hours of reaction, the product was reduced with tris(2-carboxyethyl)phosphine and purified by HPLC to give 54 mg of Dpo4-15 with a yield of 46%; (B) Electrospray ionization mass spectrum of Dpo4-15.

Figure 25:
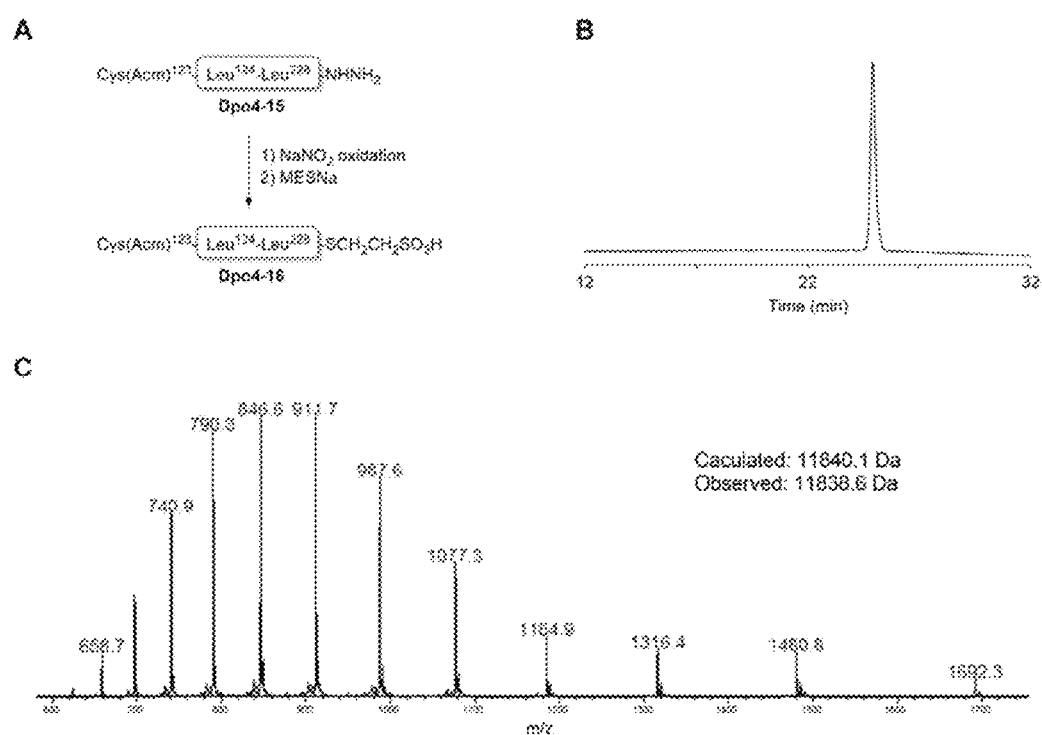

FIG. 25 illustrates the preparation of Dpo4-16. (A) 82 mg of Dpo4-15 was dissolved in 7 ml of an acidified ligation buffer (6 M Gn.HCl and 0.1 M NaH$_2$PO$_4$ in water, pH 3.1). The mixture was placed in an ice salt bath and cooled, then 140 μl of an acidified ligation buffer containing 0.5 M NaNO$_2$ was added and stirred in an ice salt bath for 30 minutes, then 1.75 ml of an acidified ligation buffer containing 0.8 M sodium sulfonate (MESNa) was added. The pH of the solution was adjusted to 5.5 with sodium hydroxide solution at room temperature. After 2 hours of reaction, the product was reduced with tris(2-carboxyethyl)phosphine and purified by HPLC to give 69 mg of Dpo4-16 with a yield of 83%; (B) Analytical high performance liquid chromatogram of Dpo4-16 (λ=214 nm), column: Welch C4; gradient: mobile phase ratio CH$_3$CN:H$_2$O from 20% to 70% (both with 0.1% TFA), elution for more than 30 minutes; (C) Electrospray ionization mass spectrum of Dpo4-16.

Figure 26:
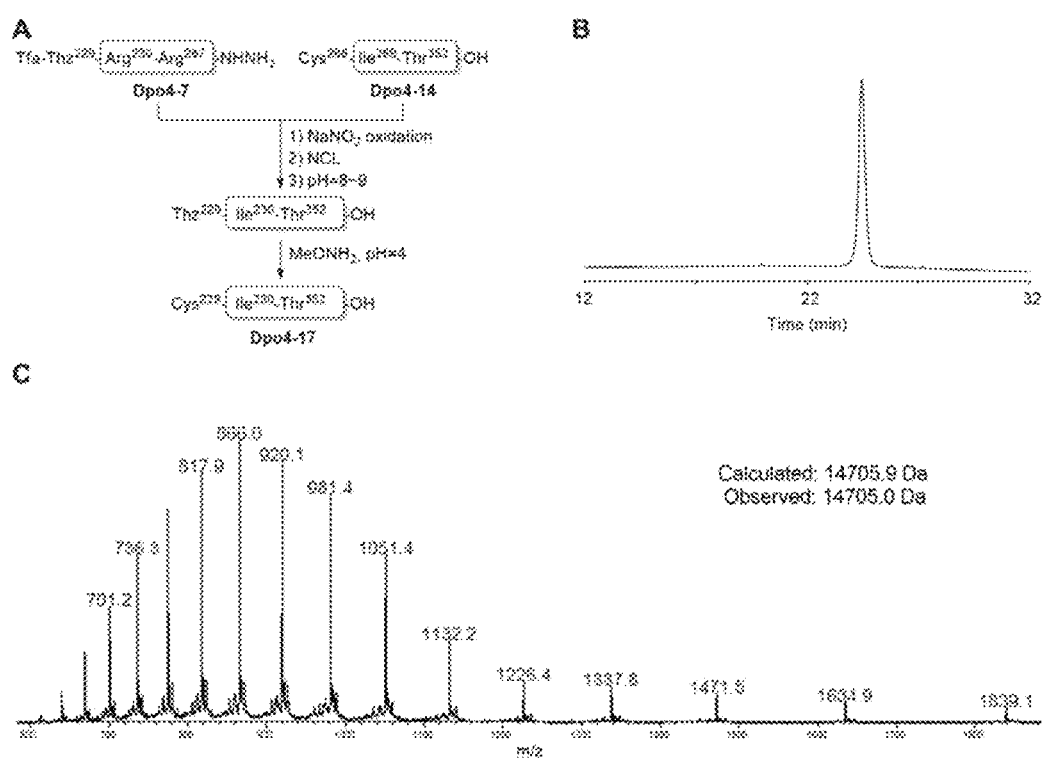

FIG. 26 illustrates the preparation of Dpo4-17. (A) The ligation reaction of Dpo4-7 (25 mg) and Dpo4-14 (47 mg) was similar to that of Dpo4-5 and Dpo4-6, see FIG. 22. Finally, 41 mg of Dpo4-17 was obtained with a yield of 59%; (B) Analytical high performance liquid chromatogram of Dpo4-17 (λ=214 nm), column: Welch C4; gradient: mobile phase ratio CH$_3$CN:H$_2$O from 20% to 70% (both with 0.1% TFA), elution for more than 30 minutes; (C) Electrospray ionization mass spectrum of Dpo4-17.

Figure 27:
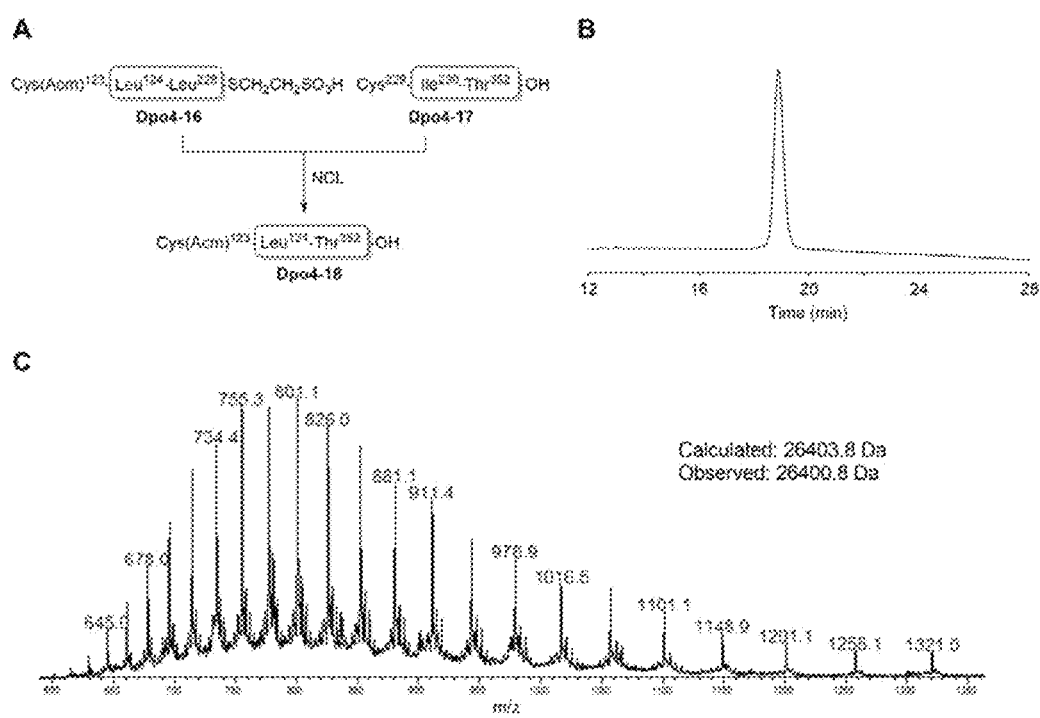

FIG. 27 illustrates the preparation of Dpo4-18. (A) 37 mg of Dpo4-16 and 41 mg of Dpo4-17 were dissolved in 1.1 ml of an aqueous solution (containing 6 M Gn.HCl, 0.1 M Na$_2$HPO$_4$, 40 mM TCEP and 125 mM MPAA, pH 6.8), the pH of the reaction mixture was adjusted to 6.6. After 12 hours of reaction, the product was analyzed by HPLC and then diluted and purified to finally give 55 mg of Dpo4-18 with a yield of 75%; (B) Analytical high performance liquid chromatogram of Dpo4-18 (λ=214 nm), column: Welch C4; gradient: mobile phase ratio CH$_3$CN:H$_2$O from 30% to 80% (both with 0.1% TFA), elution for more than 30 minutes; (C) Electrospray ionization mass spectrum of Dpo4-18.

Figure 28:
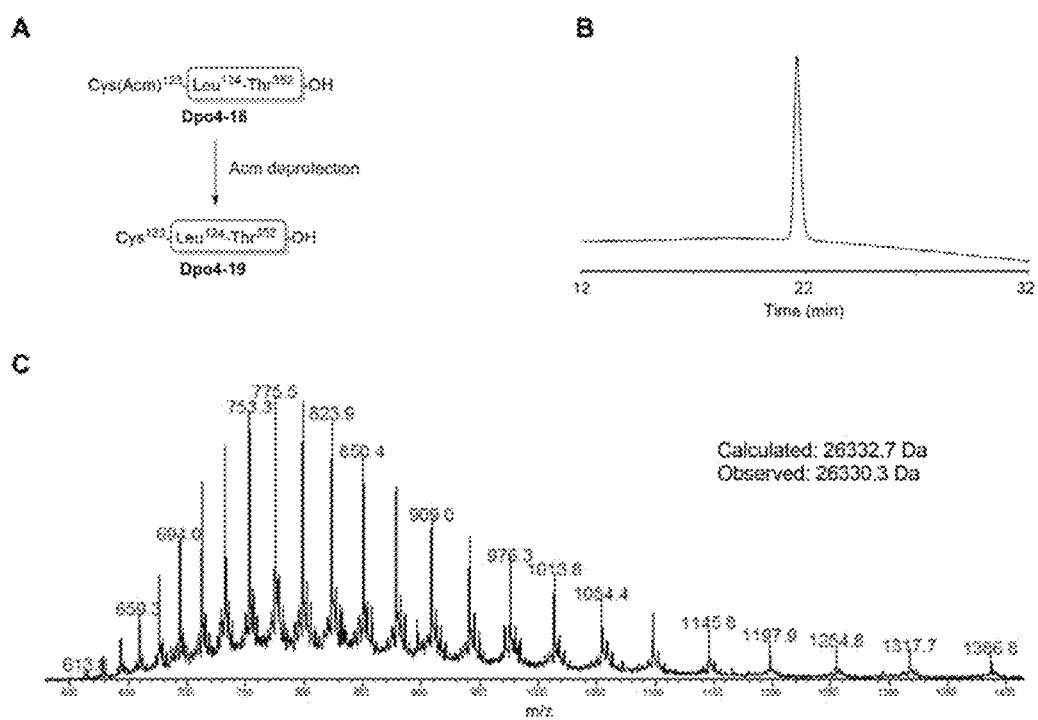

FIG. 28 illustrates the preparation of Dpo4-19. (A) Removal of the Acm group in Dpo4-18 by Pd-assisted deprotection [1], 55 mg of Dpo4-18 was dissolved in 2 ml of aqueous solution (containing 6 M Gn.HCl, 0.1 M Na$_2$HPO$_4$ and 40 mM TCEP, pH 7.1), and then 0.4 ml of an aqueous solution (containing 6 M Gn.HCl and 0.1 M Na$_2$HPO$_4$) in which 10.4 mg of PdCl$_2$ was dissolved was added to the reaction system. After 13 hours of reaction, 4 ml of an aqueous solution of 0.75 M DTT (containing 6 M Gn.HCl and 0.1 M Na$_2$HPO$_4$) was added, and the reaction mixture was stirred for 1 hour, and the product was purified by HPLC. Finally, 47 mg of Dpo4-19 was obtained with a yield of 86%; (B) Analytical high performance liquid chromatogram of Dpo4-19 (λ=214 nm), column: Welch C4; gradient: mobile phase ratio CH$_3$CN:H$_2$O from 30% to 80% (both with 0.1% TFA), elution for more than 30 minutes; (C) Electrospray ionization mass spectrum of Dpo4-19.

Figure 29:
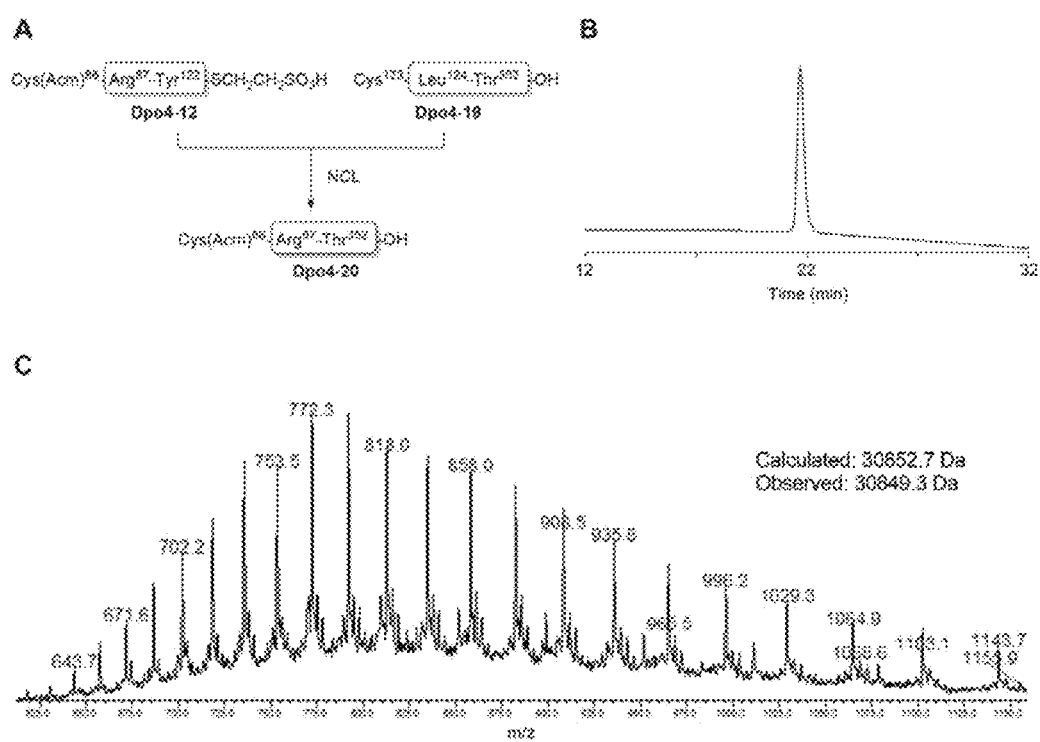

FIG. 29 illustrates the preparation of Dpo4-20. (A) 19 mg of Dpo 4-12 and 47 mg of Dpo4-19 were dissolved in 1.8 ml of an aqueous solution (containing 6 M Gn.HCl, 0.1 M Na$_2$HPO$_4$, 40 mM TCEP and 100 mM MPAA, pH 6.9), and the pH of the reaction mixture was adjusted to 6.6. After 15 hours of reaction, the product was analyzed by HPLC, followed by dilution and purification to finally give 47 mg of Dpo4-20 with a yield of 85%; (B) Analytical high performance liquid chromatogram of Dpo4-20 (λ=214 nm), column: Welch C4; gradient: mobile phase ratio CH$_3$CN:H$_2$O from 30% to 80% (both with 0.1% TFA), elution for more than 30 minutes; (C) Electrospray ionization mass spectrum of Dpo4-20.

Figure 30:
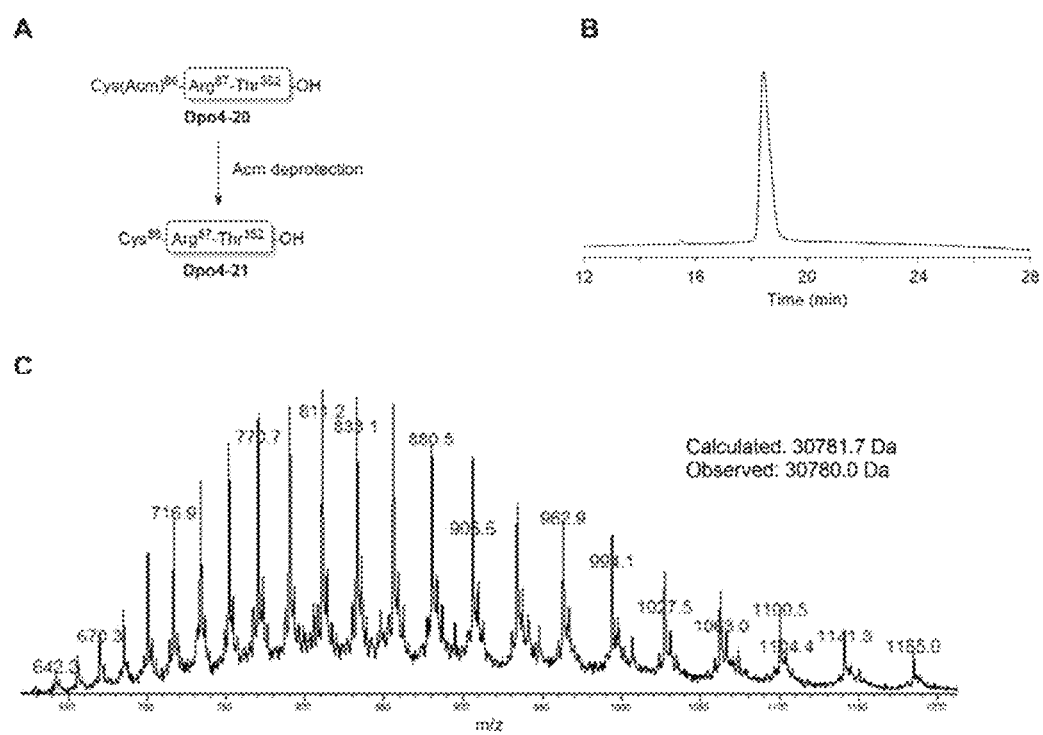

FIG. 30 illustrates the preparation of Dpo4-21. (A) 24 mg of Dpo4-20 was dissolved in 1.6 ml of acetic acid solution, then 10 mg of silver acetate was added to the solution, and after stirring for 14 hours overnight, 0.3 ml of 2-mercaptoethanol was added. The reaction system was diluted to twice with a ligation solution (6 M Gn.HCl, 0.1 M Na$_2$HPO$_4$, pH=7), and the supernatant after centrifugation was purified by semi-preparative HPLC, and the precipitate was thoroughly washed and purified. After lyophilization, 20 mg of Dpo4-21 from which the Acm group had been removed was obtained with a yield of 83%; (B) Analytical high performance liquid chromatogram of Dpo4-21 (λ=214 nm), column: Welch C4; gradient: mobile phase ratio CH$_3$CN:H$_2$O from 20% to 100% (both with 0.1% TFA), elution for more than 30 minutes; (C) Electrospray ionization mass spectrum of Dpo4-21.

Figure 31:
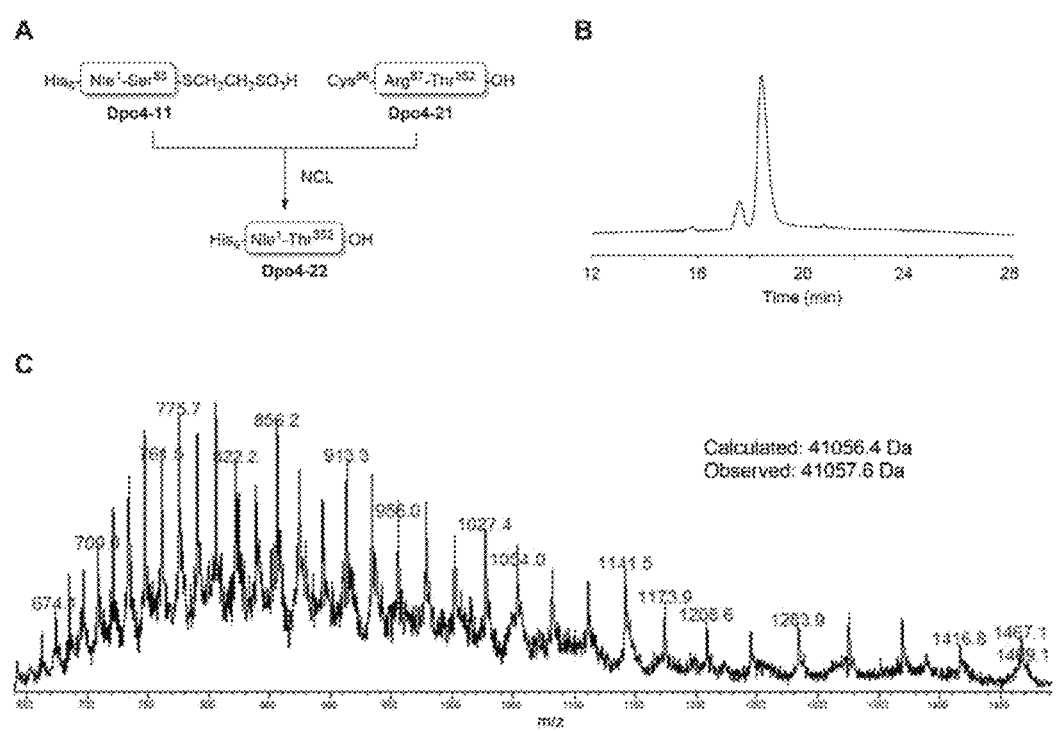

FIG. 31 illustrates the preparation of Dpo4-22. (A) 13 mg (2 eq.) of Dpo4-11 and 20 mg of Dpo4-21 were dissolved in 0.4 ml of an aqueous solution (containing 6 M Gn.HCl, 0.1 M Na$_2$HPO$_4$, 40 mM TCEP and 100 mM MPAA, pH 6.9), and the pH of the reaction mixture was adjusted to 6.6. After 15 hours of reaction, the product was analyzed by HPLC, followed by dilution and purification to finally give 21 mg of Dpo4-22 with a yield of 78%; (B) Analytical high performance liquid chromatogram of Dpo4-22 (λ=214 nm), column: Welch C4; gradient: mobile phase ratio CH$_3$CN:H$_2$O from 20% to 100% (both with 0.1% TFA), elution for more than 30 minutes; (C) Electrospray ionization mass spectrum of Dpo4-22.

Figure 32:
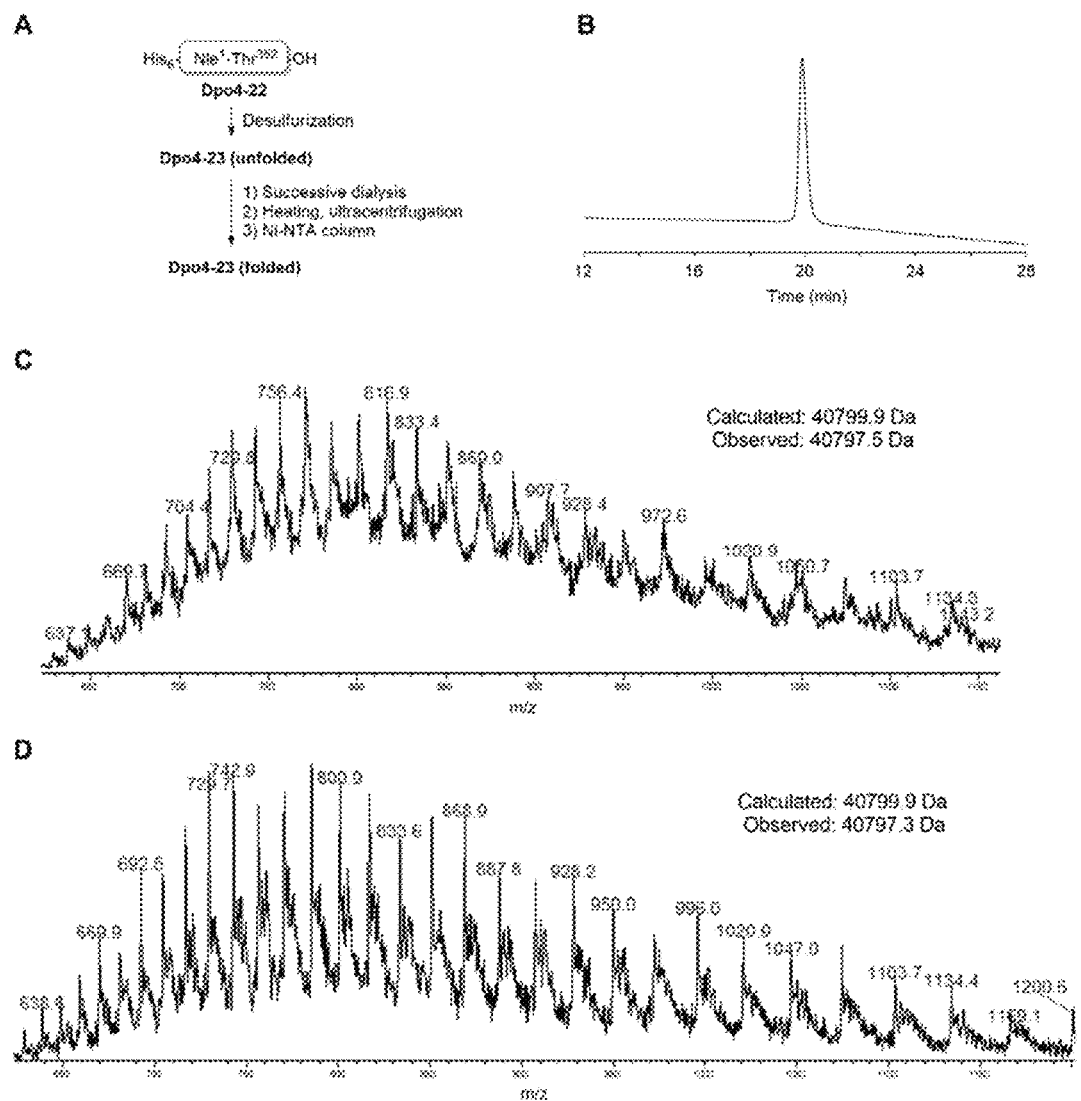

FIG. 32 illustrates the preparation of Dpo4-23 (Dpo4-5m). (A) 20 mg of Dpo4-22 was dissolved in 6 ml of 200 mM TCEP solution (containing 6 M Gn.HCl, 0.2 M Na$_2$HPO$_4$, pH 6.9), followed by addition of 0.1 mmol (32 mg) of VA-044 and 0.2 mmol (62 mg) of reduced L-glutathione. The reaction was stirred at 37° C. overnight. The desulfurized product Dpo4-23 was analyzed by HPLC and ESI-MS and purified by semi-preparative HPLC. Finally, 16 mg of lyophilized Dpo4-23 was obtained with a yield of 80%. (B) Analytical high performance liquid chromatogram of Dpo4-23 (λ=214 nm), column: Welch C4; gradient: mobile phase ratio CH$_3$CN:H$_2$O from 20% to 100% (both with 0.1% TFA), elution for more than 30 minutes; (C) Electrospray ionization mass spectrum of Dpo4-23. (D) Electrospray ionization mass spectrum of Dpo4-23 after further renaturation, heating and purification on a nickel column with a yield of 15% (approximately 2 mg of final product).

Figure 33:
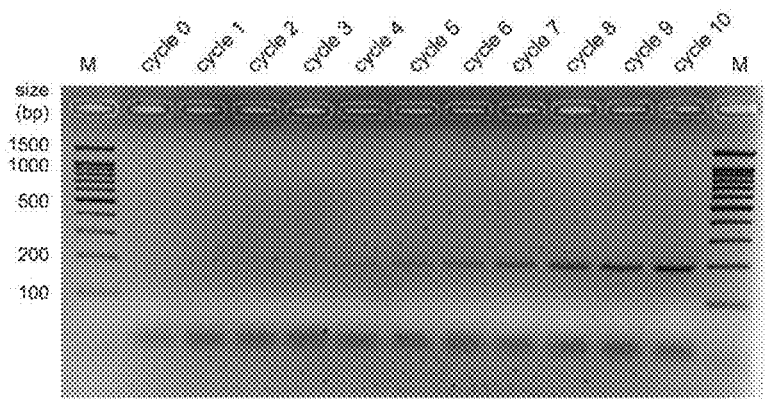

FIG. 33 illustrates a PCR-amplified 200-bp sequence using synthetic Dpo4-5m PCR, and samples were taken sequentially from each of 0 to 10th cycles.

The PCR product was analyzed by 2% agarose gel electrophoresis and stained with GoldView. The number of cycles sampled is labeled above the lane and M was the DNA marker.

Figure 34:
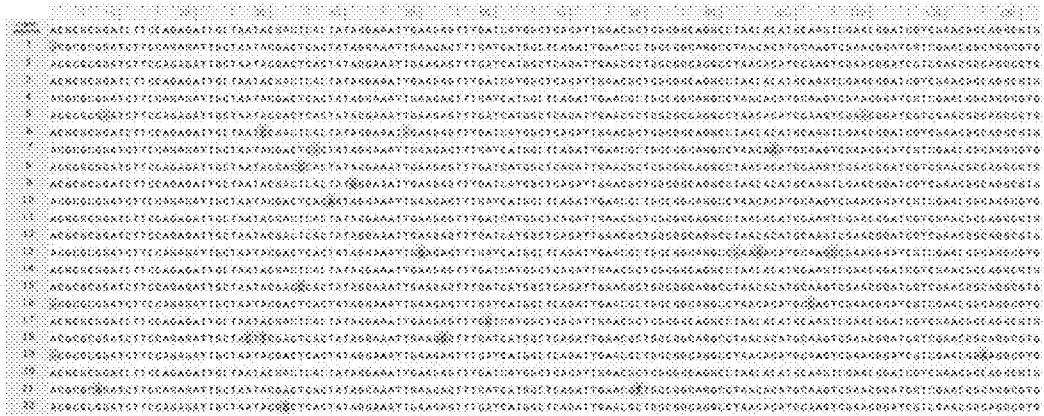

FIG. 34 illustrates the alignment of the Sanger sequencing results of the PCR amplified sequences with the original template sequence. The PCR product was cloned into the T vector, and positive colonies were picked for Sanger sequencing. There were 7 single base deletions and 19 single base mutations, indicating that the cumulative mutation rate after 35 cycles was about 0.9%.

DETAILED DESCRIPTION OF THE INVENTION

The present invention provides a method for replicating a mirror-image nucleic acid comprising: carrying out a reaction in the presence of a mirror-image nucleic acid polymerase, a mirror-image nucleic acid template, a mirror-image nucleic acid primer, and mirror-image dNTPs/rNTPs to obtain the mirror-image nucleic acid.

The term "mirror-image" as used herein, refers to an isomer that is in a mirror-image relationship with the natural material in chirality.

The term "mirror-image nucleic acid" as used herein, refers to an L-form nucleic acid that is in a mirror-image relationship with a natural nucleic acid (ie, a D-form nucleic acid). The mirror-image nucleic acid includes L-form DNA and L-form RNA. The term "mirror-image DNA" is used interchangeably with "L-form DNA" or "L-DNA".

The term "mirror-image nucleic acid polymerase" or "mirror-image polymerase" as used herein refers to a D-form polymerase that is in a mirror-image relationship with a native polymerase (ie, an L-form polymerase). The term "mirror-image polymerase" is used interchangeably with "D-form polymerase" or "D-polymerase." For example, "D-Dpo4" refers to D-form Dpo4 polymerase which is in a mirror-image relationship with the native L-form Dpo4 polymerase.

The polymerase particularly suitable for the present invention includes D-ASFV pol X, D-Dpo4, D-Taq polymerase, and D-Pfu polymerase.

Dpo4 (*Sulfolobus solfataricus* P2 DNA polymerase IV) is a thermostable polymerase which can also synthesize DNA at 37° C. Its mismatch rate is between $8 \times 10^{-3}$ to $3 \times 10^{-4}$. It is a polymerase that can replace Taq for multi-cycle PCR reaction. Its amino acid sequence length is within the reach of current chemical synthesis techniques.

Taq polymerase is a thermostable polymerase discovered by Chien and colleagues in the hot spring microbe *Thermus aquaticus* in 1976. It can remain active at DNA denaturation temperatures, so it is used in PCR instead of *E. coli* polymerase. The optimum temperature for Taq is between 75° C. and 80° C. and the half-life at 92.5° C. is about 2 hours.

Pfu polymerase is found in *Pyrococcus furiosus*, and its function in microorganisms is to replicate DNA during cell division. It is superior to Taq in that it has 3'-5' exonuclease activity and can cleave the mis-added nucleotides on the extended strand during DNA synthesis. The mismatch rate of commercial Pfu is around 1 in 1.3 million.

In some embodiments, the mirror-image nucleic acid, the mirror-image nucleic acid template, the mirror-image nucleic acid primer, and the mirror-image dNTPs/rNTPs are in L-form, and the mirror-image nucleic acid polymerase is in D-form. In some cases, different types of templates, primers, or dNTPs/rNTPs may be mixed in the reaction system (for example, a portion of D-form template primer or dNTPs/rNTPs may be mixed) without causing serious interference with the reaction.

Herein, the nucleic acid replication reaction may be carried out in only one cycle or in multiple cycles. This may be determined by persons skilled in the art according to actual needs.

The term "multiple" as used herein refers to at least two. For example, "multiple cycles" refers to 2 or more cycles, such as 3, 4, or 10 cycles.

The term "replication" as used herein includes obtaining one or more copies of a target DNA in the presence of a DNA template and dNTPs; and also obtaining one or more copies of a target RNA in the presence of a DNA template and rNTPs (this process may also be known as RNA "transcription").

In the process of nucleic acid replication, the template and the primer are usually DNA. If the target nucleic acid is DNA, dNTPs should be added to the reaction system; if the target nucleic acid is RNA, rNTPs should be added to the reaction system.

In some embodiments, the mirror-image nucleic acid is L-DNA, such as L-DNAzyme. In other embodiments, the mirror-image nucleic acid is L-RNA.

In a particularly preferred embodiment, the reaction is a polymerase chain reaction.

The term "PCR" as used herein has a meaning as known in the art and refers to a polymerase chain reaction.

In a particularly preferred embodiment, the reaction is carried out in a buffer of 50 mM Tris-HCl, pH 7.5, 20 mM $MgCl_2$, 1 mM DTT, and 50 mM KCl.

The present invention also provides a method for performing mirror-image PCR, comprising: carrying out a reaction in the presence of a mirror-image nucleic acid polymerase, a mirror-image nucleic acid template, a mirror-image nucleic acid primer, and mirror-image dNTPs/rNTPs to obtain a mirror-image nucleic acid.

The present invention also provides a method for screening a mirror-image nucleic acid molecule, comprising: contacting a library of random mirror-image nucleic acid sequences with a target molecule under a condition that allows binding of the two; obtaining a mirror-image nucleic acid molecule that binds to the target molecule; and amplifying the mirror-image nucleic acid molecule that binds to the target molecule by mirror-image PCR.

Preferably, the target molecule is immobilized on a solid phase medium, which may be more advantageous for separation and purification.

For example, after the library of random mirror-image nucleic acid sequences is contacted with the target molecule, the mirror-image nucleic acid molecule that does not bind to the target molecule may be removed by washing to obtain a mirror-image nucleic acid molecule that binds to the target molecule.

The mirror-image nucleic acid molecule can be L-DNA or L-RNA.

Preferably, the mirror-image nucleic acid polymerase used in the mirror-image PCR may be D-ASFV pol X, D-Dpo4, D-Taq polymerase or D-Pfu polymerase.

In the present invention, the term "nucleic acid polymerase" should be understood broadly and may refer to a wild-type enzyme, and may also refer to a functional variant of the enzyme.

The term "functional variant" as used herein refers to a variant comprising substitution, deletion or addition of one or more (for example, 1-5, 1-10 or 1-15, in particular, such as 1, 2, 3, 4, 5, 6, 7, 8, 9, 10, 11, 12, 15 or even more) amino acids in the amino acid sequence of a wild-type enzyme, and the variant substantially retains the biology of the wild-type enzyme. For example, 50%, 60%, 70%, 80% or 90% or more of the biological activity of the wild type enzyme is retained. The "functional variant" may be a naturally occurring variant, or an artificial variant, such as a variant obtained by site-directed mutagenesis, or a variant produced by a genetic recombination method.

In a preferred embodiment of the present invention, the mirror-image nucleic acid polymerase may comprise an affinity tag to facilitate purification and reuse of the protein, such as a polyhistidine tag (His-Tag or His tag), a polyarginine tag, a glutathione-S-transferase tag, and the like.

For example, a preferred embodiment of the present invention provides a functional variant of Dpo4 protein, Dpo4-5m, which comprises amino acid mutations at 6 positions and a His6 tag.

In a particularly preferred embodiment, the mirror-image PCR is performed in a buffer of 50 mM Tris-HCl, pH 7.5, 20 mM $MgCl_2$, 1 mM DTT, and 50 mM KCl.

The present invention also provides D-ASFV pol X, the sequence of which is set forth in SEQ ID NO: 17, wherein except for glycine which is not chiral, all other amino acids are D-form amino acids.

The present invention is further described with reference to the accompanying drawings and embodiments, which are only for the purpose of illustrating the present invention and should not be construed as limiting the present invention.

EXAMPLES

Example 1

D-Amino Acid in Mammal

D-amino acids are present in mammals. In 1965, Hoeprich and colleagues detected D-Ala in the blood of guinea pig and mouse, which was the first time that researchers had discovered D-amino acid in mammals (Corrigan, 1969). Until now, D-Ala has been found in the brains and pituitaries of various mammals, and D-Ala excretion has been found in the urine. D-Pro and D-Leu were found in seven regions of the mouse brain, indicating that D-amino acids have relatively high concentrations in the pituitary and pineal bodies (Hamase et al., 2001). In addition, D-Ser and D-Ala were also detected in the brains and blood of mammals such as human and mouse (Hashimoto et al., 1993; Hashimoto et al., 1995). D-amino acids were first thought to be synthesized by microorganisms, plants, and invertebrates, and recent studies have shown that D-Ser and D-Asp can be synthesized by mammalian tissues. It was found by isotopic labeling experiments that radioactive L-Ser can be transformed into D-Ser in rat and mouse brains. In 1999, Ser racemase was cloned and purified, which can catalyze the conversion of L-Ser to D-Ser in the rat brain (Wolosker et al., 1999). Another major source of D-amino acids in mammals is exogenous foods and microorganisms.

Chemical Synthesis of Mirror-Image Protein

Although the mirror-image amino acids have been confirmed to exist in living organisms in natural state, the natural state of the mirror-image amino acids are mainly monomeric, and also exist in short peptide segments, such as the tetrapeptide side chain amino acid d-Ala-d-Glu-r-l-Lys-d-Ala of Gram-positive bacteria. A mirror-image protein consisting of functional mirror-image amino acids in nature has not yet been discovered. The translation in the central rule is a process in which ribosomes and tRNAs participate and synthesize proteins according to mRNA genetic information. The mirror-image amino acids are not used as substrates in this process. It is generally believed that the transcription, translation and realization of major biological functions of the genetic information of living organisms depend on the natural chiral L-amino acids.

Due to the chirality of existing organisms, the mirror-image proteins cannot be obtained by a biological method. At present, the research on mirror-image proteins is achieved by chemical synthesis. Polypeptides and small proteins can be achieved by solid phase peptide synthesis (SPSS) (Kent, 1988). This method usually yields a segment of about 60 amino acids, then the deprotected peptide segments in solution are ligated one by one by natural chemical ligation (Dawson and Kent, 2000). The methods of solid phase peptide synthesis and natural chemical ligation extend the range of protein synthesis, and currently can synthesize a protein of more than 300 amino acids. Synthetic studies of mirror-image proteins can also be performed by this technique. In 1992, Kent's group synthesized the first mirror-image protease, HIV-1 protease (Milton et al., 1992). Based on the theory that the L and D enantiomers have mutually mirrored structures, scientists often speculate that mirror-image proteins have functions corresponding to the natural proteins, and this conjecture was first confirmed in the mirror-image HIV-1 protease project. L-form and D-form HIV-1 protease have the same mass spectral molecular weight, the same HPLC retention time, and the opposite circular dichroism spectral curves. In terms of activity, the L-form HIV-1 protease can cleave the L-peptide substrate, while the D-form protease can cleave the D-form substrate. In another study, two chiral baczymes (barnase) showed similar properties. Natural L-form barnase cleaves native RNA, and its activity on mirror-image RNA is about 4000 times weaker. For mirror-image D-form barnase, the activity on cleaving mirror-image RNA was significantly higher than that on native RNA (Vinogradov et al., 2015). In 1995, L-form and D-form 4-Oxalocrotonate tautomerase were chemically synthesized, and the two enantiomers showed the same reaction efficiency in catalyzing the isomerization of an achiral substrate 2-hydroxymuconic acid. Isotopically labeled hydrogen at the carbon atom of the catalytic site indicated that two chiral isomerases act on different sides of the carbon atom (Fitzgerald et al., 1995). The above studies consistently show that the mirror-image protease and the natural chiral protease have the same activity, but act on different isomeric positions.

In 2014, M. S. Kay's group synthesized the longest protein, DapA of 312 amino acids. DapA is a protein that relies on a molecular chaperone GroEL/ES and can be only folded into a functional conformation upon expression with the assistance of the molecular chaperone. GroEL/ES can fold both D- and L-chiral DapAs, but the folding efficiency for native L-DapA is higher than that for mirror-image DapA (Weinstock et al., 2014).

Study on Chemical Synthesis of Mirror-Image Nucleic Acid

Studies on the hypothesis of the early origin of life suggest that non-enzymatically catalyzed, template-directed RNA amplification reactions can be performed in a single chiral system. However, if there are two chiral RNA monomers in the system, the prolonged reaction will be prevented by the addition of its mirror-image monomer (Joyce et al., 1984). This poses a serious challenge to the theory that life originates from naturally occurring RNA. To explain this theoretical problem, Joyce and colleagues obtained an RNA polymerase ribozyme by in vitro screening, which consists of 83 ribonucleosides and can catalyze enantiomeric chiral RNA polymerization (Sczepanski and Joyce, 2014). The mirror-image RNA in this study was obtained by chemical synthesis. It could generate a full-length RNA polymerase ribozyme opposite to its own chirality by ligating 11 oligonucleotide fragments, and amplification of the two RNAs can be performed without interference in the same reaction system. This provided a theoretical possibility for the coexistence of two chiral RNA molecules and amplification of them by RNA polymerase ribozyme in the early stage of life.

In 2013, Barciszewski's group reported for the first time a catalytically active mirror-image nucleotidase designed according to the existing natural nucleotide sequence, which functioned to catalyze the cleavage of the mirror-image L-nucleotide molecule (Wyszko et al., 2013). The mirror-image nucleotidase can achieve a cleavage function in vivo. In the experiment, it was confirmed that the mirror-image nucleotidase was not easily degraded in serum, and also had the characteristics of being non-toxic and not causing an immune reaction, which made it an ideal drug molecule.

Study on Mirror-Image Nucleic Acid Aptamer

DNA/RNA was first thought to be a carrying tool for genetic information and also thought to be much simpler than the structure of a protein. But actually DNA/RNA can also be folded into a tertiary structure, which has a series of potential physiological functions. As early as in 1990, researchers discovered that RNA structure can specifically bind to a small molecule substrate. These RNA structures, like antibodies, bind selectively to the substrate and have a high affinity. These RNA structures that can bind to a particular substrate are referred to as aptamers. Later, DNA aptamers were also discovered by researchers.

In vitro screening technique utilize a library of random DNA/RNA sequences to find the nucleic acid aptamer that binds to a specific target molecule. In vitro screening must first have a library of random sequences, either DNA or RNA. The library typically contains random sequences of 30 to 80 nucleotides with two primer regions on both sides to facilitate PCR amplification. Then, multiple cycles of the screening process are performed, the target small molecule substrate is immobilized on a matrix, and the library of random sequences is added to the substrate. After washing, the unbound DNA or RNA molecule flows through the immobilized substrate, and the sequence with the binding ability that is screened will remain on top. The special sequence is then eluted for PCR amplification, and after multiple cycles of enrichment and screening, one or several nucleotide sequences that specifically bind to the substrate can be obtained.

Like the natural nucleic acid aptamer, the mirror-image nucleic acid sequence has a specific secondary and tertiary structure according to its sequence, and can bind the target molecule in close and high specificity. If a mirror-image target molecule is screened by an in vitro screening strategy and then a mirror-image nucleotide sequence is synthesized, a mirror-image nucleotide molecule capable of binding to a natural target can be obtained. The researchers obtained a mirror-image L-RNA aptamer that binds D-adenosine and L-arginine by in vitro screening (Klusmann et al., 1996; Nolte et al., 1996). D. P. Bartel obtained an L-DNA aptamer that binds vasopressin in 1997 (Williams et al., 1997). The mirror-image nucleotide molecule has the advantages of being stable and not easily degraded in the body, non-toxic, and not causing an immune reaction, has a relatively low production cost, and has a good application prospect as a drug molecule.

Research Purposes

No research can give a clear conclusion whether mirror-image biomolecules can realize the replication and transcription of genetic information, and whether mirror-image molecules have the theoretical possibility of composing life in evolution. Although mirror-image proteins have been synthesized and the activities of mirror-image proteins have been verified and their properties have been compared with native proteins by research groups, these studies usually only explain the properties of mirror-image proteins from the perspective of chemical synthesis.

Our research aimed to design and synthesize a polymerase-based mirror-image replication and transcription system. The significance of this system has the following three aspects:

I. The mirror-image replication and transcription system can realize the amplification of mirror-image DNA and RNA by polymerase, indicating that the mirror-image polymerase can catalyze the synthesis of DNA and RNA like natural chiral polymerase, and proving that the mirror-image biomolecule has effective biological activity;

II. The mirror-image replication and transcription system implements two key steps in the mirror-image center rule, laying a groundbreaking foundation for the synthesis of mirror-image primitive cells;

III. At present, the natural nucleic acid molecule obtained by in vitro screening technique as a drug has a serious defect of being easily hydrolyzed in the body. In order to avoid this problem, a special method is needed for screening of mirror-image nucleic acid. The existing in vitro screening technology screens the mirror-image target by a natural random library to obtain an effective nucleic acid sequence, and then chemically synthesizes the mirror-image nucleic acid molecule, so that the obtained mirror-image nucleic acid molecule can bind to a natural target, that is, a potential mirror-image drug. However, the limitation of this method is that many common drug targets in living organisms are proteins of more than 300 amino acids, and it is impossible to synthesize the mirror-image targets by a chemical method. If the natural target molecule and the mirror-image random library can be directly used for mirror-image in vitro screening, the universality of this technique will be greatly improved, and drug molecules will be screened for a wide range of diseases. There are no technical difficulties for the natural drug target and the mirror-image random library, but the bottleneck of mirror-image drug screening is that mirror-image PCR cannot be realized. Our mirror-image replication and transcription system can achieve mirror-image PCR. Although PCR efficiency needs further optimization and improvement, it still provides a theoretical and practical basis for mirror-image drug screening.

Experimental Materials and Experimental Methods

Experimental Drugs and Reagents

| | |
|---|---|
| Q5 DNA polymerase | NEB |
| NdeI | NEB |
| BamHI | NEB |
| Trans 5α clone competent cells | TransGen Biotech |
| BL21(DE3)pLysS expression competent cells | TransGen Biotech |
| EasyTaq | TransGen Biotech |
| Trans 2K DNA marker | TransGen Biotech |
| T4 DNA ligase | TransGen Biotech |
| Plasmid miniprep kit | Aidlab |

| | |
|---|---|
| IPTG | Aidlab |
| Gel Extraction Kit | QIAgen |
| Agarose | Biowest |
| Pre-stained protein marker | Bio-Rad |
| 40% Acrylamide | Sangon |
| Urea | Sangon |
| SYBRGold stain solution | Invitrogen |
| Coomassie Brilliant Blue Fast Stain solution | Tiangen Biotech (Beijing) |
| Ni-NTA beads | Institute of Process Engineering, CAS |
| Imidazole | Sangon |
| D-amino acids | CSBio (Shanghai) |
| L-amino acids | GL Biochem (Shanghai) |
| 2-(7-azobenzotriazole)-N,N,N',N'-tetramethyluron hexafluorophosphate | GL Biochem (Shanghai) |
| 1-hydroxy-7-azobenzotriazole | GL Biochem (Shanghai) |
| N-hydroxy-7-azobenzotriazole | GL Biochem (Shanghai) |
| 1-hydroxy-benzo-triazole | GL Biochem (Shanghai) |
| N,N'-dicyclohexylcarbimide | Alfa Aesar |
| 1,2-ethanedithiol and 4-mercaptophenylacetic acid | Alfa Aesar |
| Acetonitrile (HPLC grade) | J.T. Baker |
| Tris(hydroxymethyl)methylamine hydrochloride (Tris-HCl) | Sinopharm |
| Potassium chloride | Sinopharm |
| Magnesium acetate tetrahydrate | Sinopharm |
| Ethylenediaminetetraacetic acid | Sinopharm |
| Sodium dihydrogen phosphate | Sinopharm |
| Glycerin | Sinopharm |
| Guanidine hydrochloride | Sinopharm |
| Anhydrous ether | Sinopharm |
| 85% Hydrazine | Sinopharm |
| Reduced glutathione | J&K Scientific |
| Anisole sulfide | J&K Scientific |
| Trifluoroacetate | J&K Scientific |
| Triisopropylsilane | Beijing Ouhe Technology |
| N,N-diisopropylethylamine | Beijing Ouhe Technology |
| Sodium hydroxide | Beijing Chemical Industry Group |
| N,N-dimethylformamide | Beijing Chemical Industry Group |
| Dichloromethane | Beijing Chemical Industry Group |
| Sodium nitrite | Beijing Chemical Industry Group |
| 2-chlorotriphenyl chloride resin | Nankai Hecheng (Tianjin) |
| β-mercaptoethanol | Zhongketuozhan (beijing) |
| L-DNA | Chemgenes |
| L-dNTPs | Chemgenes |
| L-NTPs | Chemgenes |
| D-DNA primer | Tsingke (Beijing) |
| pEASY T3 Kit | TransGen Biotech |
| RNase A | Fermentas |
| PAGE DNA Purification Kit | Tiandz |
| Phenol chloroform | Solarbio |
| Glycogen | Aidlab |
| RNase inhibitor | TaKaRa |

Experimental Equipments

| | |
|---|---|
| Nucleic acid electrophoresis tank | Beijing JUNYI |
| PAGE electrophoresis tank | Beijing JUNYI |
| Benchtop thermostatic oscillators | Huamei Biochemical Instrument |
| SDS-PAGE electrophoresis tank | Bio-Rad |
| Electrophoresis apparatus | Bio-Rad |
| Gel imaging system | Bio-Rad |
| Centrifuge5424 | Eppendorf |
| Spectrophotometer | Eppendorf |
| PCR instrument | AB |
| Milli-Q Pure Water Instrument | MilliPore |
| AKTA Protein Purification System | GE |
| QIAcube | QIAgen |

Nucleic Acid Sequences

| Name | Sequence |
|---|---|
| D-/L-primer12 | 5'-ACTACGAACGCG (SEQ ID NO: 1) |
| D-/L-FAM-primer12 | 5'-FAM-ACTACGAACGCG (SEQ ID NO: 2) |
| D-/L-template18 | 5'-CTCAGTCGCGTTCGTAGT (SEQ ID NO: 3) |
| D-/L-DNAzymeTemplate | 5'-TGTACAGCCACTTCAACTAATTGCTCAACTATGGCTGTAGCACC CGCGTTCGTAGTATGCAATGCA (SEQ ID NO: 4) |
| Cy5-primer20 | 5'-Cy5-AGTGCGATACTACGAACGCG (SEQ ID NO: 5) |

| Name | Sequence |
|---|---|
| template26 | 5'-CTCAGTCGCGTTCGTAGTATCGCACT (SEQ ID NO: 6) |
| template18A | 5-CTCAGACGCGTTCGTAGT (SEQ ID NO: 7) |
| template18C | 5' -CTCAGCCGCGTTCGTAGT (SEQ ID NO: 8) |
| template18G | 5'-CTCATGCGCGTTCGTAGT (SEQ ID NO: 9) |
| L-primer15 | 5'-GATCACAGTGAGTAC (SEQ ID NO: 10) |
| L-template21 | 5'-CTATTGTACTCACTGTGATC (SEQ ID NO: 11) |
| DNAzyme marker | 5'-FAM-ACTACGAACGCGGGTGCTACAGCCATAGTTGAGCAATTAG TTGAAGTGGCTGTACA (SEQ ID NO: 12) |
| L-template27 | 5'-CGCGCTGTTATAGGGATACGGCAAAAA (SEQ ID NO: 13) |
| L-primer 11 | 5'-CGCGCTGTTAT (SEQ ID NO: 14) |
| L-FAM-primer11 | 5'-FAM-CGCGCTGTTAT (SEQ ID NO: 15) |
| L-reverse11 | 5'-GCCGTATCCCT (SEQ ID NO: 16) |

The above sequences without D-/L-tags refer to D-DNA.

ASFV Pol X Protein and DNA Sequence

Protein Sequence

```
                                               (SEQ ID NO: 17)
  1 mltliqgkki vnhlrsrlaf eyngqlikil sknivavgsl rreekmlndv dlliivpekk 61 llkhvlpnir ikglsfsvkv cgerkcvlfi ewekktyqld lftalaeekp yaifhftgpv 121 syliriraal kkknyklnqy glfknqtlvp lkittekeli kelgftyrip kkrl
```

DNA Sequence

```
                                               (SEQ ID NO: 18)
ATGTTAACGCTTATTCAAGGAAAAAAAATTGTAAATCACTTACGTTCCCG

ACTTGCGTTTGAATATAATGGACAACTTATAAAAATTTTATCAAAAAACA

TCGTTGCTGTTGGTAGTTTAAGACGCGAAGAGAAAATGCTTAATGACGTG

GATCTTCTTATTATTGTTCCAGAAAAAAAACTTTTAAAACACGTCCTGCC

CAACATTCGCATAAAGGGTCTTTCTTTTTCTGTAAAAGTCTGCGGAGAAC

GAAAGTGTGTACTTTTTATTGAATGGGAAAAAAAGACGTATCAACTTGAT

CTTTTTACGGCTTTAGCCGAGGAAAAACCATACGCAATATTTCATTTTAC

GGGTCCCGTTTCTTATCTAATAAGAATTCGAGCCGCGTTAAAAAAAAGA

ATTATAAGCTAAATCAGTATGGATTATTTAAAAATCAAACTTTAGTACCT

CTAAAAATCACTACTGAAAAGAACTTATTAAAGAATTAGGATTTACGTA

TCGCATACCTAAGAAACGTTTATAA
```

Experimental Methods

Chemical Synthesis of ASFV Pol X

The amino acid sequence of D-ASFV pol X was divided into three segments, and a natural ligation method from the C-terminus to the N-terminus was adopted. The synthesis of each polypeptide segment used a solid phase peptide synthesis method (Fmoc-SPPS) based on a strategy of using 9-fluorenylmethoxycarbonyl (Fmoc) as a protecting group. 2-C1-trityl-C1 resin (2CTC, degree of substitution 0.5 mmol/g) was used to synthesize segment 1, while hydrazine-substituted 2CTC resin was used to synthesize segment 2 and segment 6. In the synthesis of the polypeptide segment, the resin was first swollen in a mixture of dichloromethane (DCM) and N,N-dimethylformamide (DMF) for half an hour, and then the solvent was removed. Subsequently, for the segment 1, a solution of 4 eq. amino acids and 8 eq. N,N-diisopropylethylamine in 5 ml of DMF was added to the reaction tube, and the reaction was carried out for 12 hours in a thermostat shaker at 30° C., after which 200 µL of methanol was added to block unreacted active chlorine. For the segment 2 and segment 6, a solution of 4 eq. amino acids, 3.8 eq. 2-(7-azobenzotriazole)-N,N,N',N'-tetramethylurea hexafluoride phosphate (HATU), 3.8 eq. benzotriazole (HOAT) and 8 eq. N,N-diisopropylethylamine in 5 ml of DMF was added to the reaction tube, and the reaction was carried out for 1 hour in a thermostat shaker at 30° C. During the synthesis of the polypeptide segment, the method of removing the Fmoc protecting group comprised the use of a DMF solution containing 20% piperidine for soaking twice, one for 5 minutes, and the other for 10 minutes. From the second amino acid to the end, the condensation system used HATU/HOAT/DIEA. After the peptide segment was synthesized, it was immersed for 3 hours with the cleavage reagent K (Trifluoroacetic acid/phenol/water/thioanisole/ethanedithiol=82.5/5/5/5/2.5), then the system was concentrated by removing the trifluoroacetic acid with high-purity nitrogen gas, then diethyl ether was added to precipitate the polypeptide, and finally, the solid precipitate was collected by centrifugation, and the target polypeptide segment was separated and purified using a semi-preparative grade reversed-phase high performance liquid chromatography (RP-HPLC).

The natural chemical ligation of the polypeptide segments was carried out as follows. The hydrazide group-containing polypeptide segment was first dissolved in a buffer (6 M guanidine hydrochloride, 200 mM disodium hydrogen phosphate, pH 3.0). In an ice salt bath, a 15 eq. $NaNO_2$ solution was added to the reaction solution, and the reaction was carried out for 20 minutes. Subsequently, a buffer solution mixed with 40 eq. 4-mercaptophenylacetic acid (MPAA), an equivalent of N-terminal cysteine, pH 7.0 was added. After stirring uniformly, the pH of the system was adjusted to 7.0 and the reaction was carried out for 12 hours. After the reaction was completed, the system concentration was diluted by 2-fold with addition of 80 mM of trichloroethyl phosphate (TCEP) buffer. The target product was finally isolated using semi-preparative grade RP-HPLC.

The desulfurization reaction of the polypeptide was carried out as follows. First, 1 μmol of the polypeptide segment 3 was dissolved in 2.5 ml of 200 mM TCEP buffer solution (6 M guanidine hydrochloride, 0.2 M disodium hydrogen phosphate, pH=6.9), then 50 μmol VA-044 and 100 μmol reduced glutathione were added, and the solution was reacted at 37° C. for 12 hours. Finally, the desulfurization product 4 was isolated and purified by semi-preparative grade RP-HPLC.

The acetamidomethyl (Acm) protecting group of the Cys86 side chain was removed as follows. 0.5 μmol of the polypeptide segment 4 was dissolved in 1 ml of 50% aqueous acetic acid. Then 5 mg of silver acetate was added and stirred at 30° C. overnight. Then 2.5 mmol of mercaptoethanol was added and the system was diluted by 2-fold with 6 M aqueous guanidine hydrochloride solution. The precipitate was removed by centrifugation, and the supernatant was separated by RP-HPLC to obtain the target product 5.

Folding Renaturation of ASFV Pol X

The folding renaturation of D-ASFV pol X was carried out as follows. 5 mg of D-ASFV pol X was dissolved in 10 ml of 6 M guanidine hydrochloride solution, and the solution was placed in a 3K Da dialysis bag. The dialysis bag was then immersed in a buffer system containing 4 M guanidine hydrochloride (50 mM Tris-HCl, 40 mM KCl, 6 mM magnesium acetate, 0.01 M EDTA and 16% glycerol) for 10 hours, then the guanidine hydrochloride concentration was gradually reduced to 2 M, 1 M and 0 M. The dialysis bag was immersed in each concentration of guanidine hydrochloride solution for 10 hours. Using circular dichroism and mass spectrometry, it was confirmed that D-ASFV pol X was correctly folded and a disulfide bond was formed by air oxidation between D-Cys81 and D-Cys86.

Natural and Mirror-Image DNA, RNA Polymerase Reaction Method

DNA polymerization method: a polymerase reaction buffer of 50 mM Tris-HCl, pH 7.5, 20 mM $MgCl_2$, 1 mM DTT, and 50 mM KCl was formulated. 0.7 μg of ASFV pol X, 2.5 μM primer, 2.5 μM template and four kinds of 0.4 mM dNTPs were added to a 10 μl reaction system. The reaction system was placed at 37° C. for 4 hours, and the reaction was terminated by adding 1 μl of 0.5 M EDTA. The reaction yielded a DNA fragment complementary to the template.

RNA polymerization method: a polymerase reaction buffer of 50 mM Tris-HCl, pH 7.5, 20 mM $MgCl_2$, 1 mM DTT, and 50 mM KCl was formulated. 0.7 μg of ASFV pol X, 2.5 μM primer, 2.5 μM template and four kinds of 0.4 mM rNTPs were added to a 10 μl reaction system. The reaction system was placed at 37° C. for 60 hours, and the reaction was terminated by adding 1 μl of 0.5 M EDTA. The reaction yielded a complex of primer DNA and RNA.

Method for Recovering DNA/RNA Fragment by PAGE Gel

The amplified product was isolated and purified by a PAGE gel recovery method. First, a loading buffer containing xylene cyanide and bromophenol blue was added to the system in which the reaction had been terminated, and electrophoresis was carried out on a modified polyacrylamide gel of a suitable concentration, and the gel was removed after the electrophoresis was completed. DNA/RNA staining was performed with ethidium bromide. The target fragment of the DNA/RNA with desired size was cut under UV light, and the impurity band and the blank area were discarded. The cut gel piece should be as small as possible. The gel was then placed in TE buffer and mixed upside down overnight. The supernatant was carefully aspirated, and 1/10 volume of sodium acetate (3 mol/L, pH=5.2) was added to the DNA solution and mixed well to a final concentration of 0.3 mol/L. After adding 2 times volumes of pre-cooled ethanol with ice for mixing, it was thoroughly mixed again and placed at −20° C. for 30 minutes. The mixture was centrifuged at 12,000 g for 10 minutes, then the supernatant was carefully removed and all droplets on the tube wall were aspirate. The open lid EP tube was placed on the bench at room temperature to allow the residual liquid to evaporate to dryness. By adding an appropriate amount of $ddH_2O$ to dissolve the DNA/RNA, high purity enzymatically amplified L-DNA/RNA fragment can be obtained.

Mirror-Image DNAzyme Reaction Method

A DNAzyme sequence was amplified using a 100 μl reaction system, which is a single-stranded DNA short strand with self-splicing activity. The reaction system was: 50 mM Tris-HCl, pH 7.5, 20 mM $MgCl_2$, 1 mM DTT, and 50 mM KCl, 28.9 μg of D-ASFV pol X, 5 μM primer12 primer, 5 μM DNAzymeTemplate and 1.6 mM dNTPs. The reaction was carried out at 37° C. for 36 hours. Next, the reaction product was added to the loading buffer, and the band was separated on a 12% PAGE gel using 300 V for 3 hours. In order to facilitate the separation by the gel and the recovery of the full-length reaction product, the single-stranded DNAzyme, the DNAzymeTemplate was designed to be 10 nucleotides longer than the full-length product. After the gel plate was removed, the full-length product sequence was developed and excised. The gel piece was treated as described above, diffused overnight and precipitated by ethanol to recover the DNA. The precipitated product was dissolved in a buffer of 1:50 mM HEPES, pH 7.0 and 100 mM NaCl, and heated at 90° C. for 2 minutes, and then cooled on ice for 5 minutes. An equal volume of a buffer of 2:50 mM HEPES, pH 7.0, 100 mM NaCl, 4 mM $ZnCl_2$ or 40 mM $MgCl_2$ was then added to initiate the reaction. The reaction was carried out at 37° C. for 36 hours. Finally, the reaction was terminated with EDTA. The sample was separated and developed on a 12% PAGE gel.

Mirror-Image Multi-Cycle Polymerase Reaction Method

A polymerase reaction buffer of 50 mM Tris-HCl, pH 7.5, 20 mM MgCl2, 1 mM DTT, and 50 mM KCl was formulated. 2.672 μg of D-ASFV pol X, 2.5 μM L-FAM-primer, 2.5 μM L-template and four kinds of 0.4 mM L-dNTPs were added to the reaction system. The reaction system was placed at 37° C. for 4 hours, and the reaction was terminated by adding 1 μl of 0.5 M EDTA. Since ASFV pol X has a strong ability to bind DNA and it cannot be dissociated even under the condition of heat denaturation at 95° C., the polymerase in the previous cycle of reaction was removed by phenol chloroform extraction. In the second cycle of reaction, the reaction system was heated to 95° C. for 30 seconds and then cooled to room temperature. Further, 0.334 μg of D-ASFV pol X was added to the reaction system, and the reaction system was allowed to stand at 37° C. for 20 hours. The third cycle was carried out in the same way. The reaction product was separated on 8 M urea denatured 20% PAGE gel and imaged using the Typhoon Trio+ system. Quantification of the electrophoresis band was performed using ImageQuant software.

Digestion of Natural RNA Polymer Product by RNase A

The L-ASFV pol X RNA reaction system (see 2.2.3) was reacted at 37° C. for 36 hours, and then was heated to 75° C. for 10 minutes to inactivate ASFV pol X and RNase inhibitor.

1 µg/µl, 0.1 µg/µl, and 0.01 µg/µl of RNase A were respectively added to each of the three experiments and incubated at 23° C. for 10 minutes. The reaction was terminated by the addition of 20 units of RNase inhibitor and a loading buffer was added. The reaction product was separated on 8 M urea denatured 20% PAGE gel and imaged using the Typhoon Trio+ system.

Design of Genetic Information Replication and Transcription System for Mirror-Image Chirality Overview In the organism of the earth, the amino acids constituting the proteins are almost L-form except for glycine which has no charility, and the riboses in the nucleic acids are all D type. Proteins and nucleic acids are characterized by chiral unitarity. The erroneous addition of one or several mirror-image amino acids to a natural protein may alter the secondary structure of the protein or even lose its biological activity (Krause et al., 2000). The organism has a strict chiral unitarity. Although researchers have not been able to find clear evidence of why the mirror-image chirality is lost in evolution, we can still study the properties of mirror-image proteins and nucleic acids by chemical synthesis, and try to construct the biological primitives required for the mirror-image organism of the cells. As the core of the mirror-image organism, the research focuses on trying to construct key steps in the mirror-image center rule, DNA replication and RNA transcription.

Design of Mirror-Image DNA Replication System

In natural living organisms, DNA replication requires a long DNA strand as a template, a short DNA strand as a primer, a DNA polymerase, four kinds molecules of dATP, dCTP, dTTP, and dGTP, and suitable solution conditions such as suitable pH and Mg$^{2+}$ ion. With reference to the natural life system, the components of a mirror-image DNA replication system were designed, comprising 50 mM Tris-HCl, pH 7.5, 20 mM MgCl$_2$, 1 mM DTT, and 50 mM KCl, with addition of mirror-image protein and nucleic acid molecule, D-polymerase, L-DNA template, L-DNA primer and four L-dNTPs. The mirror-image protein and nucleic acid molecule do not exist in natural living organisms. For chemical synthesis processes, there is no difference in the chemical processes required to synthesize a chiral molecule and an enantio chiral molecule. So, it was determined to obtain a mirror-image D-polymerase and L-DNA by Chemical Means.

The chemical synthesis of protein is mainly through the solid phase synthesis of peptides of about 60 amino acids, and the deprotected peptides are ligated one by one through natural chemical ligation in solution. The upper limit of the protein that can currently be synthesized is approximately 350 amino acids depending on the sequence. The size of *E. coli* polymerase I is 928 amino acids, the commonly used taq polymerase has 832 amino acids, and the T4 DNA ligase, which is generally considered to have a simpler function of the polymerase, also has 487 amino acids. These enzymes are beyond our synthesis range. Polymerase ASFV pol X, African swine fever virus polymerase X, of 174 amino acids was selected through literature search.

ASFV encodes two DNA polymerases, one is an eukaryotic type DNA polymerase of family B for replication of the viral genome; and the other is a DNA polymerase of family X, named ASFV pol X (Oliveros et al., 1997). ASFV Pol X is the smallest DNA polymerase found today (Showalter and Tsai, 2001), consisting of 174 amino acids and having a size of 20 kDa. ASFV Pol X is a template-dependent polymerase with very low fidelity, lacks 3'-5' exonuclease activity, and has poor recognition ability for dideoxynucleotides (Oliveros et al., 1997).

By aligning the gene sequence of ASFV Pol X with other representative polymerases of family X, it can be seen that ASFV Pol X and human bovine, murine TdT, human, murine pol β, etc. have a certain relationship in structure and function. The three-dimensional structure of ASFV Pol X has been solved by NMR. Unlike other polymerases, Pol X has only one palm structure and one C-terminal domain (Maciejewski et al., 2001). In eukaryotic Polβ, there is generally an N-terminal domain responsible for DNA binding. Pol X does not have this key domain, but its ability to bind DNA is stronger than that of Polβ.

In addition, ASFV Pol X can bind to the intermediate of a single nucleotide excision repair (BER) and efficiently repair individual nucleotide gap (Showalter et al., 2001). In the BER step, Pol X repairs the gap and is easy to introduce mutation. In the final step, a new synthetic strand with a mismatch is ligated into the genome by a fault-tolerant ligase encoded by ASFV. Pol X introduces new mutation when repairing the genome, which helps the virus to mutate in order to survive in an environment with stress.

Chemical Synthesis of ASFV Pol X Polymerase

The chemical total synthesis method of D-ASFV PolX uses the solid phase peptide synthesis technology (SPPS) proposed by Merrifield in 1963, which is currently the most effective method for peptide synthesis. Depending on the protection strategy, there are mainly two methods of adopting tert-butoxycarbonyl (Boc) and fluorenylmethoxycarbonyl (Fmoc). In this project, it was proposed to use a Fmoc-solid phase synthesis technique to ligate D-form amino acids into a polypeptide.

Although in theory the yield of each step of the SPPS condensation reaction can reach 99%, in practice Fmoc-solid phase synthesis technology can usually only synthesize peptide chains of less than 50 amino acids. For this reason, synthesis of protein often needs to ligate the polypeptide segments, in other words, a target protein molecule is divided into several segments such that each segment has less than 50 amino acids, and then each segment is ligated by a highly efficient chemical reaction to obtain the target protein molecule. Therefore, in this project, it was proposed to divide the polypeptide chain of the target D-ASFV protein molecule into 4 segments, and using a convergence method of two-two combination, the full-length amino acid sequence of the target protein was obtained by a modified one-pot natural chemical ligation (NCl), protein hydrazide ligation method.

Figure 1:
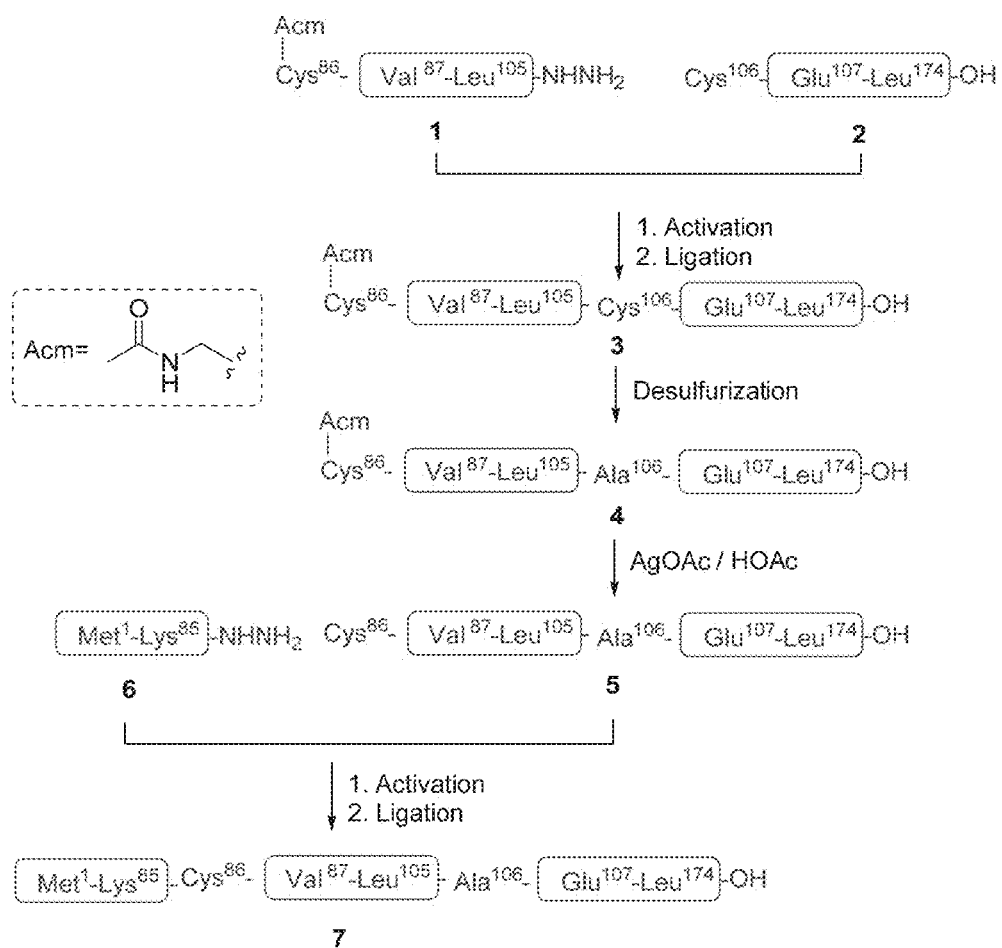
FIG. 1 illustrates the chemical synthesis route of D-ASFV Pol X. The ASFV pol X of 174 amino acids was synthesized and ligated by three segments: peptide segment 1: Met1-Lys85, peptide segment 2: Cys86-Leu105 and peptide segment 3: Ala106-Leu174. Cys86 was first protected with Acm, Cys86-Leu105 was synthesized, and then peptide segment 3: Cys106-Glu107-Leu174 was synthesized. After activation and ligation, the ligation product of peptide segment 2 and peptide segment 3 was obtained, and then Cys106 was desulfurized to form Ala106. Then peptide segment 1 was synthesized, the Acm protecting group of peptide segment 2 was catalytically removed, and activation and ligation were performed to obtain full-length ASFV pol X polymerase.

Since the site of the hydrazide ligation must utilize cysteine, it was intended to mutate the alanine at position 36 and position 129 to cysteine. After completion of the ligation reaction, a desulfurization reaction was carried out to reduce cysteine to alanine (Qian and Danishefsky, 2007). At the same time, in order to avoid the occurrence of side reaction during the ligation reaction, it was necessary to carry out side chain sulfhydryl protection for the cysteine at positions 81 and 86, and then to carry out the removal after the completion of the ligation reaction. It was intended to use acetamidomethyl (Acm) as a thiol protecting group during the reaction (Liu et al., 2012). The specific synthetic route and steps for synthesizing D-ASFV pol X are shown in FIG. 1.

Since D-ASFV pol X cannot be degraded by common proteases (such as trypsin and pepsin, the experimental results are not listed) and cannot be sequenced, the sequence of L-ASFV pol X was analyzed by mass spectrometry only, and 100% of the pol X sequence was covered in the test results (Table 3.1).

TABLE 3.1

Chemically synthesized L-ASFV pol X mass spectrometry sequencing peptide segment sequences

| Segment sequence | XCorr | Charge | MH+ [Da] | ΔM [ppm] | RT [min] |
| --- | --- | --- | --- | --- | --- |
| EEKmLNDVDLLIIVPEK | 4.86360168 | 2 | 2014.09123 | 6.67686844 | 43.7154 |
| HVLPNIRIKGLSFSVKVcGER | 2.49292898 | 3 | 2409.36637 | 4.78211214 | 44.34 |
| KcVLFIEWEK | 3.71132851 | 2 | 1351.71477 | 5.0557844 | 38.6446 |
| KKTYQLDLFTALAE | 3.88172317 | 2 | 1640.89983 | 6.31761428 | 43.7574 |
| KLLKHVLPNIR | 3.55191755 | 2 | 1330.87224 | 3.02709865 | 31.6344 |
| KTYQLDLFTALAEEKPYAIFHFTGPVSYLIR | 6.0060935 | 3 | 3631.95664 | 10.0763472 | 54.9092 |
| LNQYGLFKNQTLVPLKITTEKELIKELGFTYRIPKKRL | 2.74559188 | 5 | 4533.6656 | 7.29527526 | 54.3708 |
| mLTLIQGKKIVNHLRSRLAFEYNGQLIK | 2.66363716 | 3 | 3299.90256 | 7.61680303 | 49.6173 |
| NYKLNQYGLFK | 3.87206316 | 2 | 1387.74187 | 3.58682542 | 33.5826 |
| SRLAFEYNGQLIKILSKNIVAVGSLRREEK | 2.5462563 | 5 | 3431.98255 | 9.8659898 | 54.0116 |

For verifying the feasibility of the synthetic route, and also a cost-saving consideration, the synthesis of L-ASFV pol X was first carried out. Thereafter, D-ASFV pol X was synthesized in the same manner.

Renaturalation and Analytical Detection of Chemical ASFV Pol X Polymerase

Figure 2:
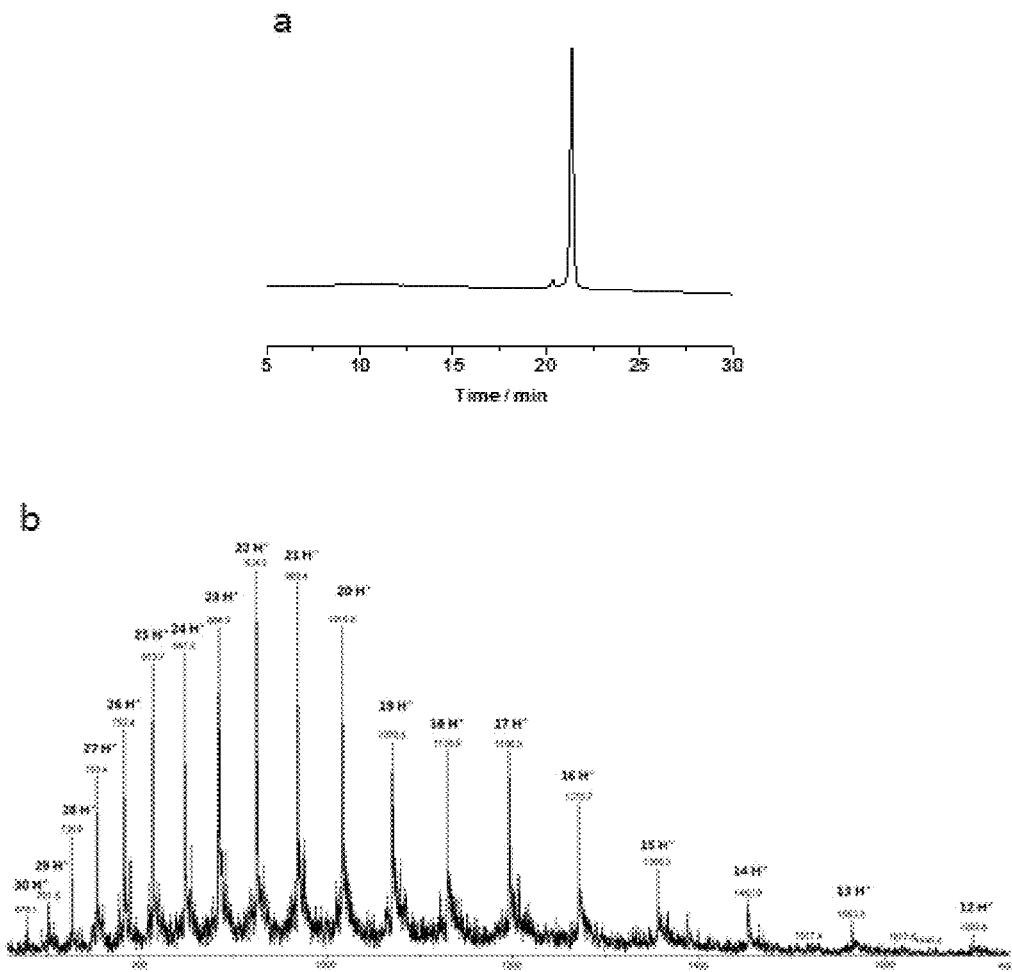
FIG. 2 illustrates the detection of the full-length product of D-ASFV pol X synthesis. a. HPLC spectrum of D-ASFV pol X after folding. HPLC analysis used a absorption wavelength of 214 nm, and a Vydac C18 (4.6×250 mm) LC column. b. ESI-MS spectrum, by analyzing and calculating the ion peak map, the size of the main synthetic product was observed to be 20317.0 Da, while the theoretical value of ASFV pol X was 20316.0 Da.

After obtaining the full-length L- and D-ASFV pol X, they were subjected to reverse-phase chromatography (RP-HPLC) purification using a Vydac C18 (4.6×250 mm) liquid chromatography column with TFA and separated with a 20% to 70% acetonitrile gradient (FIG. 2). A strong absorption of the main peak and a weak impurity peak were obtained. The molecular weight of the synthetic full-length product of D-ASFV pol X determined by electrospray ionization mass spectrometry (ESI-MS) was 20317.0 Da, and the theoretical value was 20316.0 Da.

Figure 3:
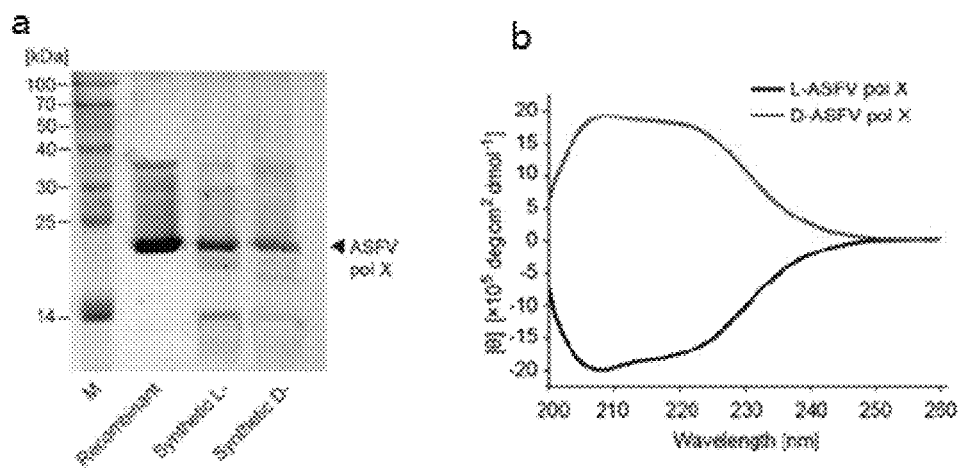
FIG. 3 illustrates L- and D-ASFV pol X detection. a. SDS-PAGE detection, E. coli-expressed, chemically synthesized L-ASFV pol X polymerase and chemically synthesized D-ASFV pol X polymerase were separated on 15% SDS-PAGE gel and detected by silver staining. M, protein molecular weight marker. b. CD detection, L-form and D-form chemically synthesized ASFV pol X were tested on an Applied Photophysics Pistar-180 CD spectrometer, and the absorption curve was the average of three independent tests subtracting the background.
Figure 4:
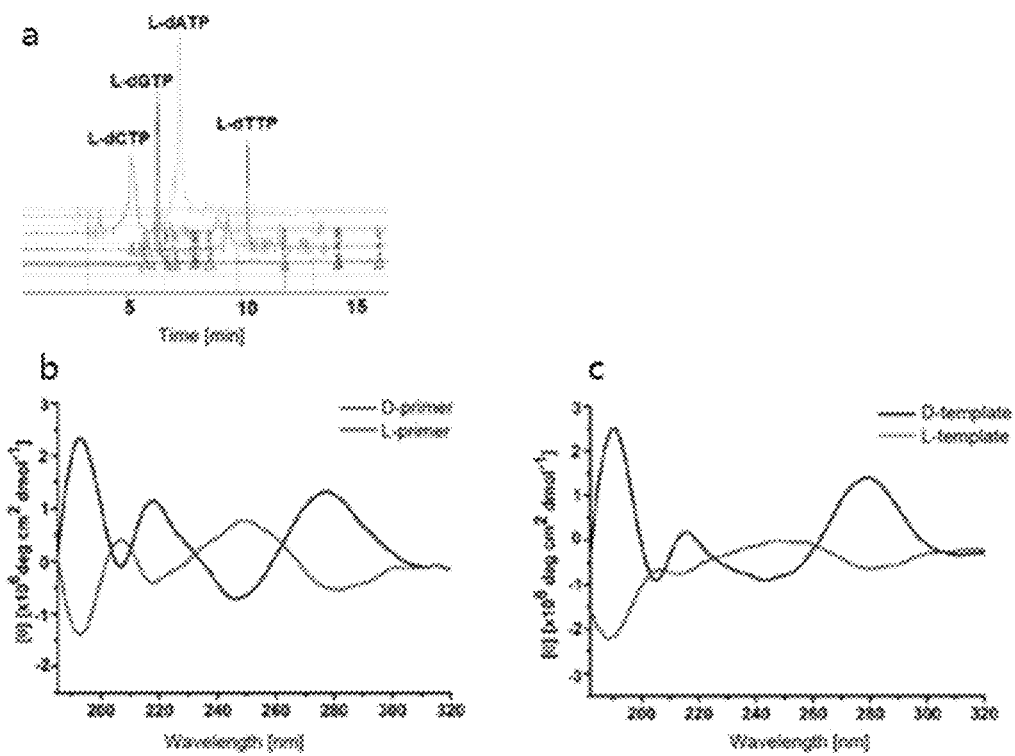
FIG. 4 illustrates a mirror-image DNA assay. a. HPLC detection (provided by Chemgenes), the purification and analysis of four L-dNTPs were carried out by HPLC, the results of L-dATP and L-dGTP showed almost no impurity peaks, while L-dTTP and L-dCTP had obvious impurity peaks. b. Primer12 CD detection, for the commercially available HPLC purified L-form and PAGE purified D-form primer12, the absorption curves had a symmetrical relationship (the actual concentration of L-primer12 was less than that of D-primer). c. Template18 CD detection, for the commercially available L-form and D-form template18, the absorption curves in the CD detection had a symmetric relationship (the loading concentration of the sample of L-template18 was actually less than that of D-primer).

The synthesized D-ASFV pol X was renatured by denaturation-dialysis method. The lyophilized polymerase dry powder was first added to 10 ml of a dialysate containing 6 M guanidine hydrochloride, and the dialysate contained 50 mM Tris-HCl, pH 7.4, 40 mM KCl, 6 mM (AcO)$_2$Mg, 0.01 M EDTA and 16% glycerol. During the dialysis process, the concentration of guanidine hydrochloride in the dialysate was continuously lowered from 4 M, 2 M to 0, and the dialysis was stirred at 4° C. for 10 hours each time. A disulfide bond was formed between D-Cys81 and D-Cys86 by air oxidation. The E. coli expressed, the synthesized L- and the synthetic D-ASFV pol X were also compared by SDS-PAGE, and their band positions were consistent (FIG. 3). We also observed a small number of peptide segments that were not completely ligated. We compared the L- and D-ASFV pol X by circular dichroism spectroscopy (CD).

Detection of Mirror-Image DNA

After the successful synthesis of D-ASFV pol X polymerase, the mirror-image nucleic acid was still missing in the mirror-image genetic information replication system. The mirror-image DNA fragments such as L-primer12 and L-template18 (see 2.1.3 for the sequence) and four L-dNTPs were purchased from Chemgenes, USA.

BRIEF SUMMARY

A system for mirror-image DNA replication was designed, including a mirror-image polymerase, a mirror-image DNA, four mirror-image dNTPs, and appropriate buffer conditions. The mirror-image DNA and four dNTPs were obtained from Chemegenes. Since the mirror-image protein could not be obtained by a biological method, ASFV pol X polymerase of 174 amino acids was found, and a synthetic route was designed and L- and D-ASFV pol X polymerase were synthesized. The protein was folded into the correct conformation by guanidine hydrochloride denaturation-dialysis renaturation. After detection by mass spectrometry and SDS-PAGE, it was verified that the size of the chemically synthesized protein was consistent with the native protein. Further, by CD detection, the absorption spectra of the native and mirror-image polymerases were observed to be symmetric. The correctness of the chemically synthesized protein sequence was verified by sequencing the synthetic L-ASFV pol X. Thus, various components of the mirror-image DNA replication system had been obtained, and conditions for subsequent studies on the mirror-image polymerase reaction had been complete.

Functional Study of Mirror-Image Chiral Genetic Information Replication and Transcription System Overview So far, there is no research on the replication and transcription of mirror-image DNA. For the synthetic mirror-image polymerase, first it needs to verify the possibility of interaction between the mirror-image protein and DNA, the chiral specificity of the mirror-image polymerase, and whether the replicated DNA is biologically active. Meanwhile, attempts have been made to achieve multi-cycle amplification of the mirror-image DNA, which can be used in research to obtain more mirror-image nucleic acid molecules in the future. Since some enzymes in the X polymerase family to which ASFV pol X belongs can utilize NTP and template complementary amplification to obtain RNA molecule, it was also attempted to try template-based transcription based on the mirror-image DNA replication system.

DNA Extension Catalyzed by Mirror-Image Polymerase

Figure 5:
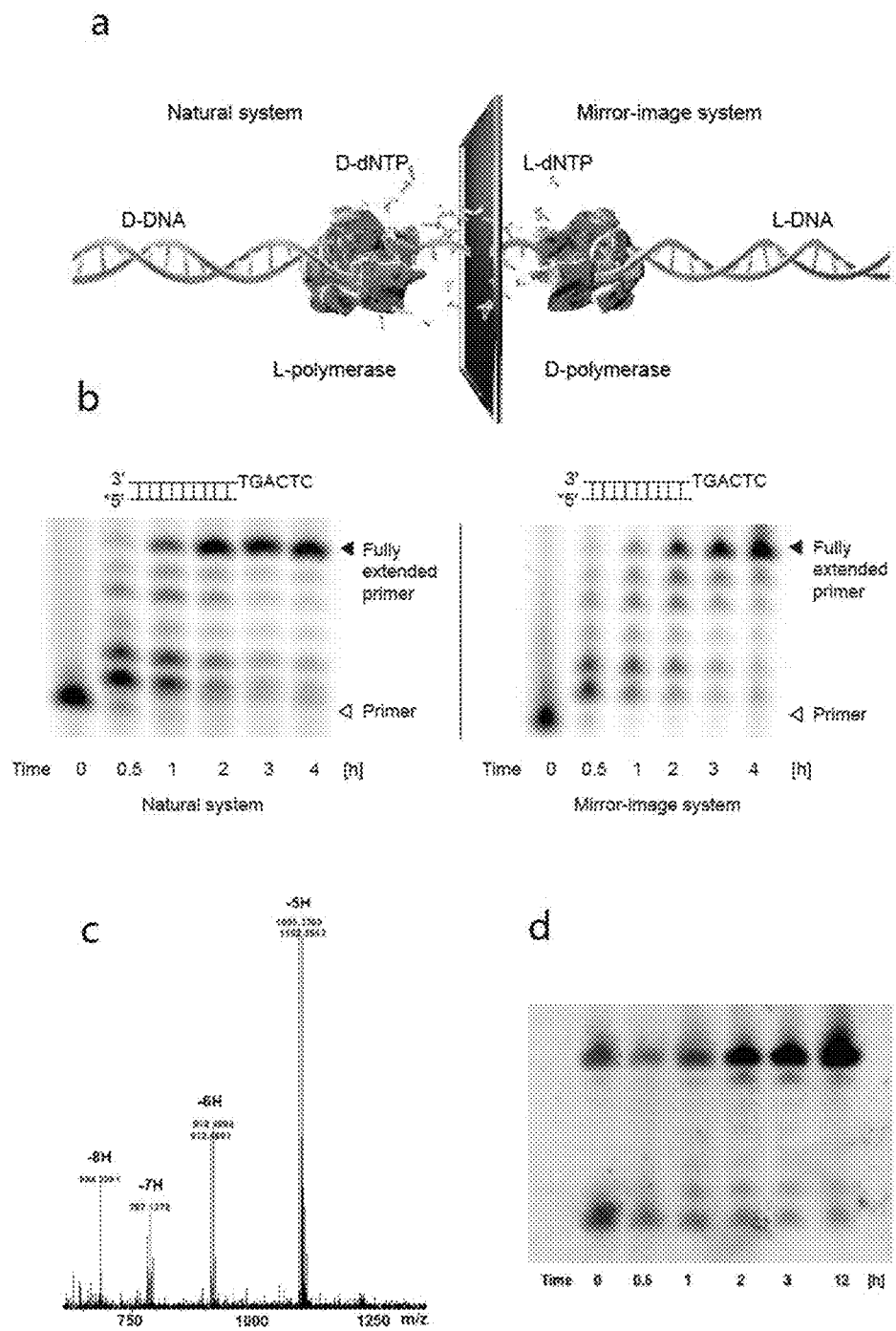
FIG. 5 illustrates the DNA extension catalyzed by a mirror-image polymerase. a. Schematic diagram of natural and mirror-image DNA replication systems, the natural DNA replication system comprised L-polymerase, D-DNA and D-dNTPs; mirror-image DNA replication system comprised D-polymerase, L-DNA and L-dNTPs. b. DNA extension catalyzed by natural and mirror-image polymerase (12 nt primer, 18 nt template), the buffer conditions were 50 mM Tris-HCl, pH 7.5, 20 mM MgCl$_2$, 1 mM DTT, and 50 mM KCl, and to a 10 μl natural or mirror-image reaction system, a corresponding chiral 0.7 μg of ASFV pol X, 2.5 μM primer 12, 2.5 μM template 18 and four kinds of 0.4 mM dNTPs were added. The reaction system was placed at 37° C. for 4 hours. "*" indicates a 5'FAM mark. c. ESI-MS detection of L-DNA full-length product, the expected molecular weight of the full-length product was 5516.9 (theoretical value of 5517.6) and the molecular weight of the template was 5481.9 (theoretical value of 5481.6) by analytical calculation. d. DNA extension catalyzed by natural and mirror-image polymerase (15 nt primer, 18 nt template), the reaction system was carried out in 50 mM Tris-HCl pH 7.5, 20 mM MgCl$_2$, 1 mM DTT, and 50 mM KCl. And 2.5 μM 15-nt L-primer15 (without FAM modification), 2.5 μM 21-nt L-template21, 0.2 mM L-dNTPs (the concentration for each kind), and 1.4 μg of D-ASFV pol X were added. After 12 hours of reaction at 37° C., separation was performed by 20% PAGE gel and detection was performed by Sybr Gold staining.

A mirror-image DNA replication system has been designed and the major components of the system have been obtained by chemical synthesis (FIG. 5a). In an achiral pH 7.5 Tris-HCl buffer, 20 mM $Mg^{2+}$ was added, 0.7 μg of L-ASFV pol X polymerase, 2.5 μM D-template18, 2.5 μM D-primer12 and 0.2 mM D-dNTPs were added to the native system; the same concentration of D-ASFV pol X polymerase as well as D-primer, template and dNTPs were added to the mirror-image system. The reaction systems were allowed to stand at 37° C. for 4 hours. A fluorescein phosphoramidate (FAM) label was added to 5' ends of the both L-form and D-form primers, while the template was not modified. Thus, the primer band could be seen by excitation with 488 nm light without dyeing. In both systems, both native and mirror-image 12 nt primers extended to 18 nt (FIG. 5b). On the 8M urea denatured 20% PAGE gel, the position of each base from 12-18 nt can be clearly distinguished. 0 h was used as a control group, the primer length was 12 nt, and 4 h was a fully extended end product with a length of 18 nt. According to the template sequence, it was speculated that the extended 6 bases were ACTGAG, indicating that four kinds of dNTPs can be used as substrates to synthesize DNA strands in the mirror-image system. This conclusion still required subsequent complementary pairing verification. It was further desirable to verify that the mirror-image extension product has the correct mirror-image nucleoside added. Since the current generation of sequencing methods still relies on polymerases and natural dNTP derivatives, this system cannot be used for L-DNA sequencing. An attempt was made to verify the mass of the 18 nt extension product by mass spectrometry. The molecular weight of the full-length mirror-image extension product was 5516.9 Da (theoretical value of 5517.6 Da) by ESI-MS. The full-length product of 18 nt was considered to have the correct mass within the error range. In addition, it was desirable to understand whether the mirror-image amplification system has limitations and whether it can be applied to different primers and template sequences. In another set of experiments, a 15 nt primer and a 21 nt template (15 nt primer without FAM labeling, PAGE gel stained with Sybr Gold) were used, and the phenomenons of primer reduction, appearance of intermediate band, and an increase in the amount of full-length DNA could still be observed, indicating that the mirror-image DNA extension can be used for different DNA sequences (FIG. 5d).

Mirror-Image DNA Replication System

Figure 6:
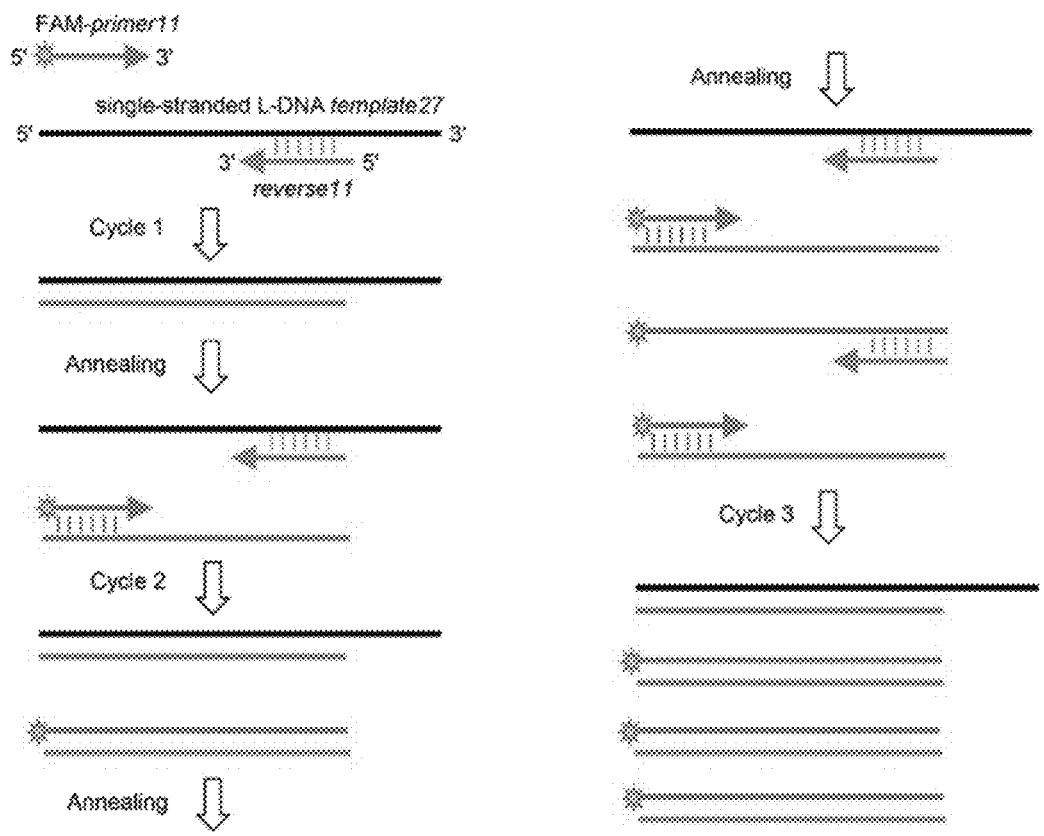
FIG. 6 illustrates a schematic diagram of multi-cycle amplification of mirror-image DNA. In the first cycle, the reverse 11 primer without FAM is amplified to obtain a double-stranded template. In the second cycle, the FAM-labeled primer11 can only complement to the template amplified by the first cycle (orange-red) to obtain the full-length product. In the third cycle, the fluorescent full-length product is produced in an amount three times that of the second cycle.
Figure 7:
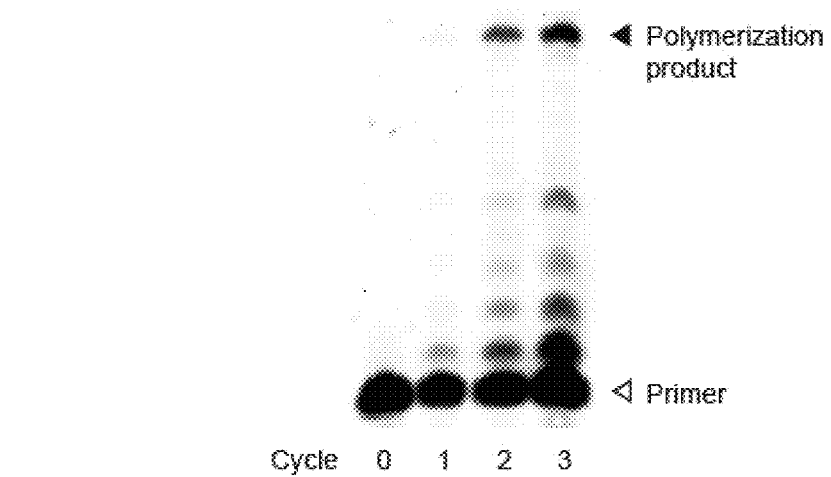
FIG. 7 illustrates multi-cycle amplification of a mirror-image DNA replication system. D-ASFV pol X amplifies L-DNA in multiple cycles, cycle 0 was the control group and was sampled before cycle 1 was performed. Cycle 1 amplification yielded the full-length product of reverse11, which could be used as a template by subsequent cycles. Samples were separated on 8 M urea denatured 20% PAGE gel and scanned for fluorescence with Typhoon Trio+. All products detected were FAM-labeled DNA.

An attempt was made to perform a multi-cycle PCR amplification of the mirror-image DNA replication system. Although ASFV pol X is not a thermostable enzyme, multiple cycles of amplification can be performed by adding enzyme per cycle. The binding of ASFV pol X to DNA blocked the amplification of the next cycle, so phenol chloroform extraction was performed at the end of each cycle to remove the protein, followed by the addition of fresh ASFV pol X. Extraction per cycle resulted in a large DNA loss (recovery efficiency of approximately 40%) and only 3 cycles of amplification were preformed. Since the number of cycles was small and it was difficult to detect an increase in DNA product, a FAM-labeled primer was used, and it can only use the full-length extension product produced in the first cycle for the second round of amplification (FIG. 6). FAM-labeled primer11, unlabeled reverse11, and template27 were used in the reaction, and the full-length product was 22 nt (see 2.1.3 for the sequence). By quantification of the FAM-labeled full-length product, a 2.3-fold amplification was detected from the second to the third cycle, and the theoretical amplification value was 3 (FIG. 7). The results theoretically confirmed the feasibility of multi-cycle amplification of DNA in the mirror-image DNA replication system.

Base Complementary Pairing Specificity of Mirror-Image DNA Replication System

Figure 8:
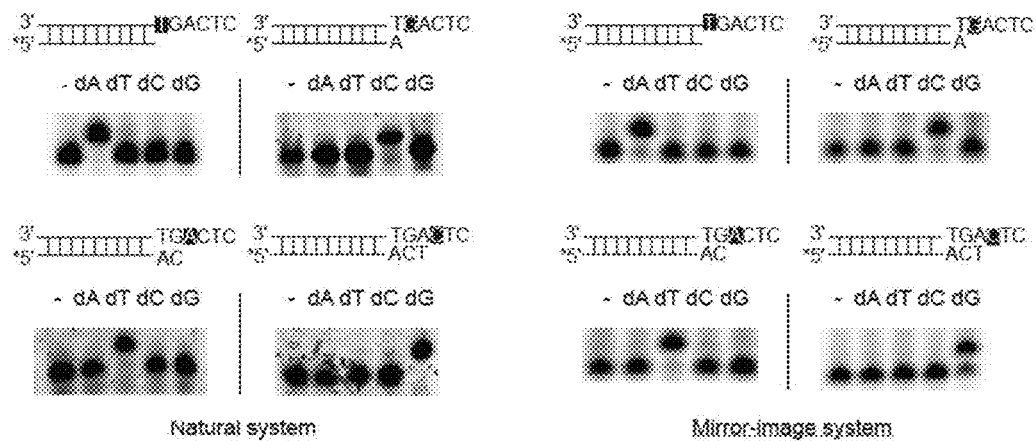
FIG. 8 illustrates the base complementary pairing specificity of the mirror-image DNA extension. One of the corresponding chiral 0.2 mM dATP, dTTP, dCTP, and dGTP was added to the natural or mirror-image system. The next base of the template was A, T, C, G (white box mark on black background), buffer conditions were 50 mM Tris-HCl pH 7.5, 20 mM MgCl$_2$, 1 mM DTT, and 50 mM KCl. And a corresponding chiral 0.7 μg of ASFV pol X, 2.5 μM primer, 2.5 μM template18 were added. The reaction was carried out at 37° C. for 30 minutes, electrophoresis was performed on a 20% PAGE gel and the fluorescent signal was scanned with a Typhoon Trio+ scanner. "*" indicates a 5'FAM mark. "-" indicates a control group to which D or L-dNTPs were not added.

It was further desirable to detect whether the mirror-image polymerase catalyzed DNA amplification complied with the rule of base complementary pairing. Four kinds of dNTPs were separately added to the reaction system, and the extension was detected when the next base of the template was A, T, C, and G (FIG. 8). For the natural system, we used primer12 and four different templates, of which the $13^{th}$ base at the 3' end was A, T, C, and G, respectively. For the mirror-image system, in order to reduce the cost of purchasing the mirror-image DNA, the extension of 1, 2, 3 nt was performed with primer12, and primer13, primer14, and primer15 were obtained by recovering from PAGE gel, which were complementary to template18, and the next base in the template was T, G, A, and C, respectively. It was observed that only under the four correct pairing conditions of A:T, T:A, C:G, G:C, dNTP can be efficiently added to the 3' end of the primer sequence without obvious mismatch, consistent in both natural and mirror-image systems. Therefore, the mirror-image DNA replication system also followed the complementary pairing rules and has a certain degree of fidelity.

Chiral Specificity of Mirror-Image DNA Replication System

Regarding the chiral specificity of polymerase when adding dNTPs, some studies have been conducted on natural polymerases. Previous studies have shown that DNA extensions catalyzed by mammalian polymerase γ, E. coli polymerase I, and HIV-1 reverse transcriptase-catalyzed are inhibited by L-dTTP, whereas for mammalian polymerase α, L-dTTP does not inhibit the DNA polymerization catalyzed by it, and for mammalian β, the inhibition effect is weak (Yamaguchi et al., 1994). L-dTTP inhibits human DNA polymerase γ, δ, bovine thymus terminal transferase, but does not inhibit human DNA polymerase β, however DNA polymerases β, γ, δ cannot use L-dTTP as substrate. The addition of L-nucleoside at the 3' end renders DNA difficult to be degraded by 3'-5' exonuclease (Focher et al., 1995). Therefore, some polymerases are inhibited by mirror-image dNTPs when adding two substrates, and some may not. Our study hopes to demonstrate whether there is chiral specificity for mirror-image ASFV pol X and whether its polymerase activity is inhibited by natural chiral dNTPs. In our study, we first tried to add a combination of different chiral polymerases, primer-templates, and dNTPs separately, and then tried to react both the natural and mirror-image systems in the same solution.

Figure 9:
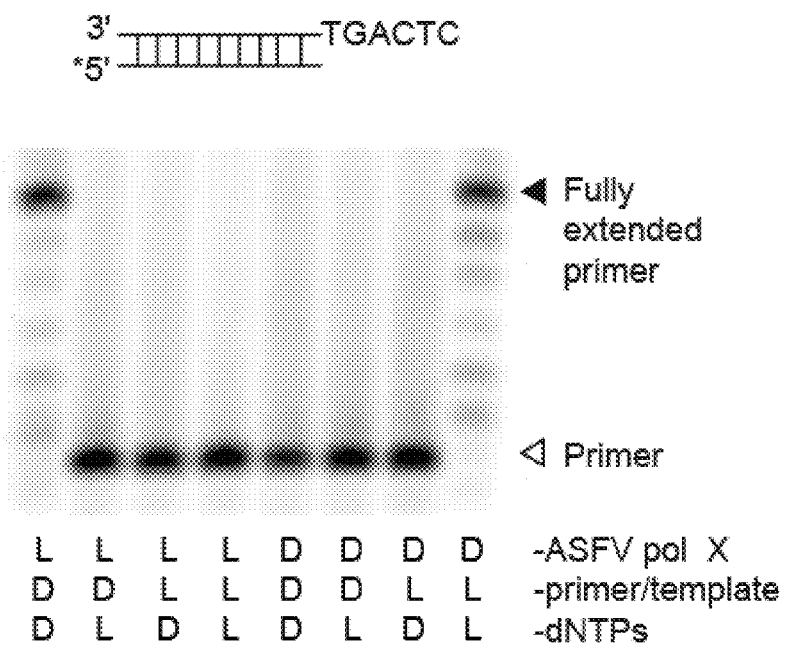
FIG. 9 illustrates the chiral specificity of mirror-image DNA extension. In buffer conditions of 50 mM Tris-HCl pH 7.5, 20 mM MgCl$_2$, 1 mM DTT, and 50 mM KCl, 0.7 μg of ASFV pol X, 2.5 μM primer, and 2.5 μM template 18 were added. The chirality of the protein, primer-template, and dNTPs are listed below the figure, and there is a total of 8 combinations. The reaction was carried out at 37° C. for 12 hours, electrophoresis was performed on a 20% PAGE gel and the fluorescent signal was scanned with a Typhoon Trio+ scanner. "*" indicates a 5'FAM mark.

The chirality of ASFV pol X, primer-template and dNTPs was changed under the same buffer conditions as before. There are two types of chirality, L-form and D-form, for each component and there were totally 8 combinations in the system (FIG. 9). The system was incubated at 37° C. for 12 hours and the results were observed on a 20% PAGE gel. It was found that the natural system of L-ASFV pol X, D-primer-template, and D-dNTPs could extend from 6 bases to full-length, and the mirror-image system of D-ASFV pol X, L-primer template and L-dNTPs could extend to the full-length, but no other combination could extend. For example, L-ASFV pol X, D-primer-template, L-dNTPs, and natural polymerase could not add mirror-image dNTPs to the 3' end of the natural primer; L-ASFV pol X, L-primer-template, D-dNTPs, and natural polymerase could not add native dNTPs to the 3' end of the mirror-image primer; D-ASFV pol X, L-primer-template, D-dNTPs, and mirror-image polymerase could not add native dNTPs to the 3' end of the mirror-image primer; D-ASFV pol X, D-primer-template, L-dNTPs, and mirror-image polymerase could not add mirror-image dNTPs to the 3' end of the native primer. Therefore, in the mirror-image and natural systems, the primer-template and dNTPs with wrong chirality could not be used as substrate to participate in the extension reaction, and the natural and mirror-image DNA replication systems had good chiral specificity.

Figure 10:
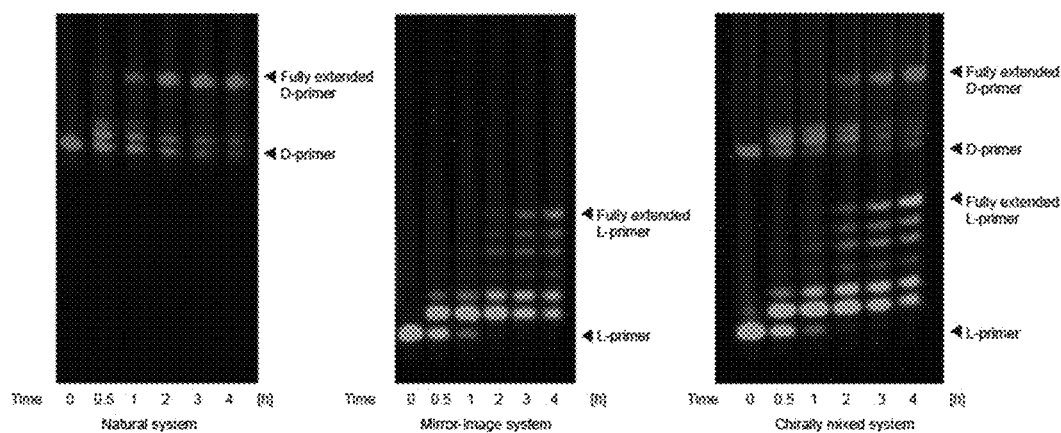
FIG. 10 illustrates the reactions of the natural and mirror-image systems in the same solution. In buffer conditions of 50 mM Tris-HCl pH 7.5, 20 mM MgCl$_2$, 1 mM DTT, and 50 mM KCl, 0.7 μg of each of the two chiral ASFV pol X, 2.5 μM natural 5'-end Cy5 labeled primer20, 2.5 μM natural template26, 2.5 μM mirror-image 5'-end FAM-labeled primer12, 2.5 µM mirror-image template18, and four kinds of dNTPs for each kind of charility, each with a final concentration of 0.2 mM, were added. The reaction system was reacted at 37° C. for 4 hours, and the reaction products were separated on 8 M urea denatured 20% PAGE gel and scanned with Typhoon Trio+ in Cy5 and FAM fluorescence modes, and the pictures were combined together.
Figure 11:
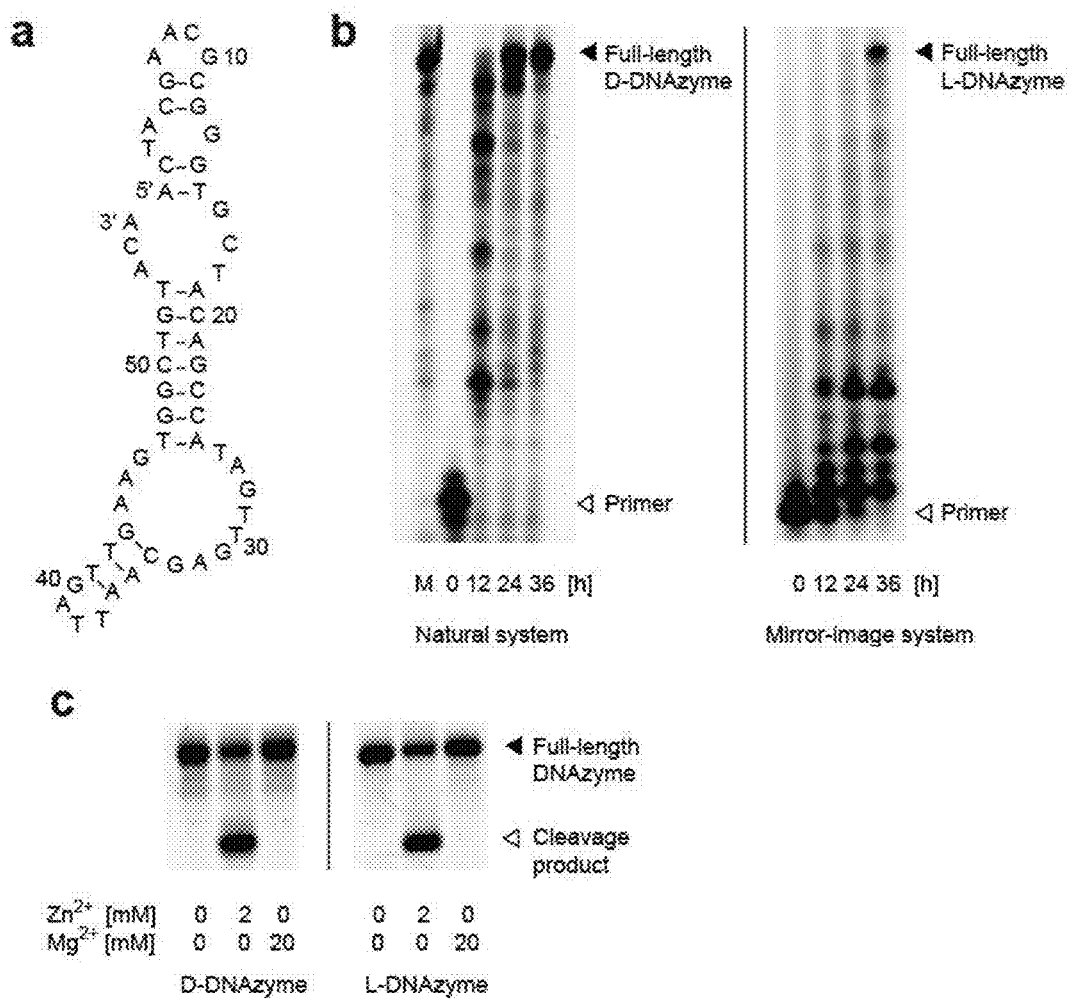
FIG. 11 illustrates the enzyme synthesis and activity assay of native and mirror-image DNAzymes. a. Zn2+-dependent DNAzyme secondary structure. A 12 nt primer sequence was added to the 5' end of the 44 nt DNAzyme to a full-length of 56 nt. The secondary structure was generated by the mfold server (Zuker, 2003). b. Enzymatic synthesis of DNAzyme. Both native and mirror-image DNAzymes were reacted in a buffer of 50 mM Tris-HCl, pH 7.5, 20 mM $MgCl_2$, 1 mM DTT, and 50 mM KCl, and 66 nt DNAzyme template and 12 nt primers were added and reacted at 37° C. for 36 hours to obtain a full-length product. M, the marker was a chemically synthesized 56 nt sequence as a molecular weight standard. c. The extended full-length DNAzyme was excised from the PAGE gel, spread in a buffer overnight, and precipitated by a Tiandz PAGE gel recovery kit. The precipitated DNA was dissolved in a buffer of 1:50 mM HEPES, pH 7.0 and 100 mM NaCl, and heated at 90° C. for 2 min, and then cooled on ice for 5 min. An equal volume of a buffer of 2:50 mM HEPES, pH 7.0, 100 mM NaCl, and 4 mM $ZnCl_2$ or 40 mM $MgCl_2$ was then added to initiate the reaction (final concentrations of $Zn^{2+}$ and $Mg^{2+}$ were 2 mM and 20 mM). The reaction was carried out at 37° C. for 36 hours. Finally, the reaction was terminated with EDTA. The samples were separated and developed on a 12% PAGE gel.

Furthermore, it was desirable to explore whether natural and mirror-image systems were interfering with each other in the same solution system. The previously described literature indicated that for some polymerases, mirror-image dNTPs prevented the DNA extension reaction from proceeding. Our experiments used the same buffer system as before, with the addition of identical concentrations of ASFV pol X and dNTPs of both kinds of charilty. In order to separately observe the extension of the primers, we designed primers and template sequences of different lengths, and used different fluorescent modifications. The natural reaction used Cy5-labeled primer20 and template26, and the mirror-image reaction used FAM-labeled primer12 and template18. Both chiral primers and templates of the same concentration were added to the same solution system, and the reaction product was separated and detected on a 20% PAGE gel after reacting at 37° C. for 4 hours (FIG. 10). The red band was the natural reaction between 21 nt and 26 nt, while the green band was the mirror-image reaction between 12 nt and 18 nt. The sample on the left was the control group with only the natural system, the middle was the control group with only the mirror-image system, and the right was the experimental group with the same concentration of the natural system and mirror-image system in the same solution system. It can be seen that in the experimental group, both systems could extend to the full-length of 18 nt and 26 nt respectively, and the reaction rate of the mixed system was similar to that of the single reaction, indicating that the natural system and mirror-image system did not have serious mutual interference in the same solution.

Enzymatic Synthesis and Functional Detection of Mirror-Image DNAzyme

It had been verified that a mirror-image DNA replication system could rely on a template to synthesize DNA and had a certain base complementary pairing specificity. It was further desirable to verify that the mirror-image DNA sequence synthesized by the mirror-image polymerase was biologically active.

In the 1990s, in vitro selection was created and applied. This technology can be used to design and screen with a complex library of random DNA or RNA sequences to obtain functional DNA or RNA molecules, mainly aptamers that bind to a particular target, and catalytically active ribozymes and deoxyribozymes (DNAzymes). Taking nucleic acid aptamer as an example, in vitro screening firstly synthesizes a single-stranded nucleic acid sequence library containing 20-80 random sequences with a library complexity of $10^{14}$. The primary sequences of the different nucleic acids in the library are different and they form different spatial configurations in solution. The random library is interacted with the target molecule under suitable conditions to capture DNA or RNA molecules capable of binding to the target, and these molecules are subjected to PCR amplification. The affinity of these amplified molecules for the target is enhanced relative to the original random library, then they are used as a secondary library, followed by a second round of screening of the target molecule. Thus, a high affinity nucleic acid aptamer sequence can be screened by repeated amplification.

D-ASFV pol X was selected to synthesize an L-DNAzyme sequence and its deoxyribozyme activity was verified. R. Breaker and colleagues found and validated the activity of multiple DNAzyme sequences in the study of year 2013 (Gu et al., 2013). We selected a 44 nt $Zn^{2+}$-dependent DNAzyme as a synthetic target. The designed full-length DNAzyme comprised a 12 nt primer sequence at the 5' end and a complete 44 nt DNAzyme sequence (FIG. 11*a*):

```
                                          (SEQ ID NO: 12)
5' ACTACGAACGCGGGTGCTACAGCCATAGTTGAGCAATTAGTTGAAGT
GGCTGTACA
```

Its reverse complement sequence was used as a template (10 nt was added to the 3' end of the template for easy recovery of the single double strand), and the full-length DNAzyme sequence was obtained after 36 hours of extension with primer 12 (FIG. 11*b*). It was found from the alignment with the marker that the size of the DNAzyme synthesized by the polymerase was correct. The natural polymerase catalyzed the synthesis of full-length sequence of DNAzyme at a higher rate than the mirror-image system, which may be due to impurities in the mirror-image primer, template, and dNTPs. This experiment further demonstrated that the extended length of the mirror-image DNA replication system was above 44 nt and had no apparent sequence selectivity. The full-length DNAzyme gel was further stained and excised, carefully separated from the 66 nt template, spread overnight in buffer, and the DNAzyme sequence was precipitated using a kit. After dissolving the DNAzyme, the 56 nt DNAzyme sequence was folded into the correct structure by heating at 90° C. and then cooled to room temperature. Then, buffer 2 was added to the reaction system to initiate the reaction. The control buffer 2 contained 20 mM $Mg^{2+}$, and the experimental group contained 2 mM $Zn^{2+}$, which were reacted at 37° C. for 36 hours. DNAzymes synthesized by both natural and mirror-image enzymes were able to achieve high efficiency self-splicing in the presence of 2 mM $Zn^{2+}$ ions, and were not self-splicing in control experiment lacking $Zn^{2+}$ or adding $Mg^{2+}$ (FIG. 11*c*). Therefore, it was demonstrated that the DNAzyme sequence synthesized by mirror-image ASFV pol X had self-splicing activity.

DNA Template Dependent Mirror-Image Transcription It has been verified that the mirror-image DNA polymerase could perform primer extension according to the DNA template, and it was desirable to investigate whether the mirror-image DNA can be transcribed into a mirror-image RNA. The known X-family DNA polymerase has poor selectivity for dNTPs and rNTPs, pol μ can add dNTPs or rNTPs to the DNA strand according to the template. Quantitatively, its selective specificity for rNTP is 1000 times lower than that of pol β (Sa and Ramsden, 2003). It has not been verified whether ASFV pol X could utilize rNTP. First, rNTP was added to the system of primer12 and template18 using the natural chiral ASFV pol X. It was found that although the efficiency of the extension was much reduced, a full-length extension product was still obtained after 36 hours (FIG. 12a).

RNase A specifically catalyzes the cleavage of the next nucleotide 5' phosphodiester bond of the ribose of RNA at the C and U residues, which recognizes the 3',5' phosphodiester bond but does not cleave the 2',5' bond, forming a 3'C or 3'U oligonucleotide having a 2',3'-cyclic phosphate derivative. The extension product after 36 hours of reaction was heated to 75° C. for 10 minutes, RNase inhibitor and ASFV pol X were inactivated, and then different concentrations of RNase A were added for digestion (FIG. 12b). It can be seen that the heating reaction in the first step did not degrade the RNA, but the addition of RNase A caused the full-length 18 nt product to degrade to 13 nt, and the higher the concentration of RNase A was, the more obvious the degradation was. This experiment demonstrated that the digestion of RNA synthesis product by RNase A verified that it was rNTP that was added, and in a manner of 3',5' linkage.

Figure 12:
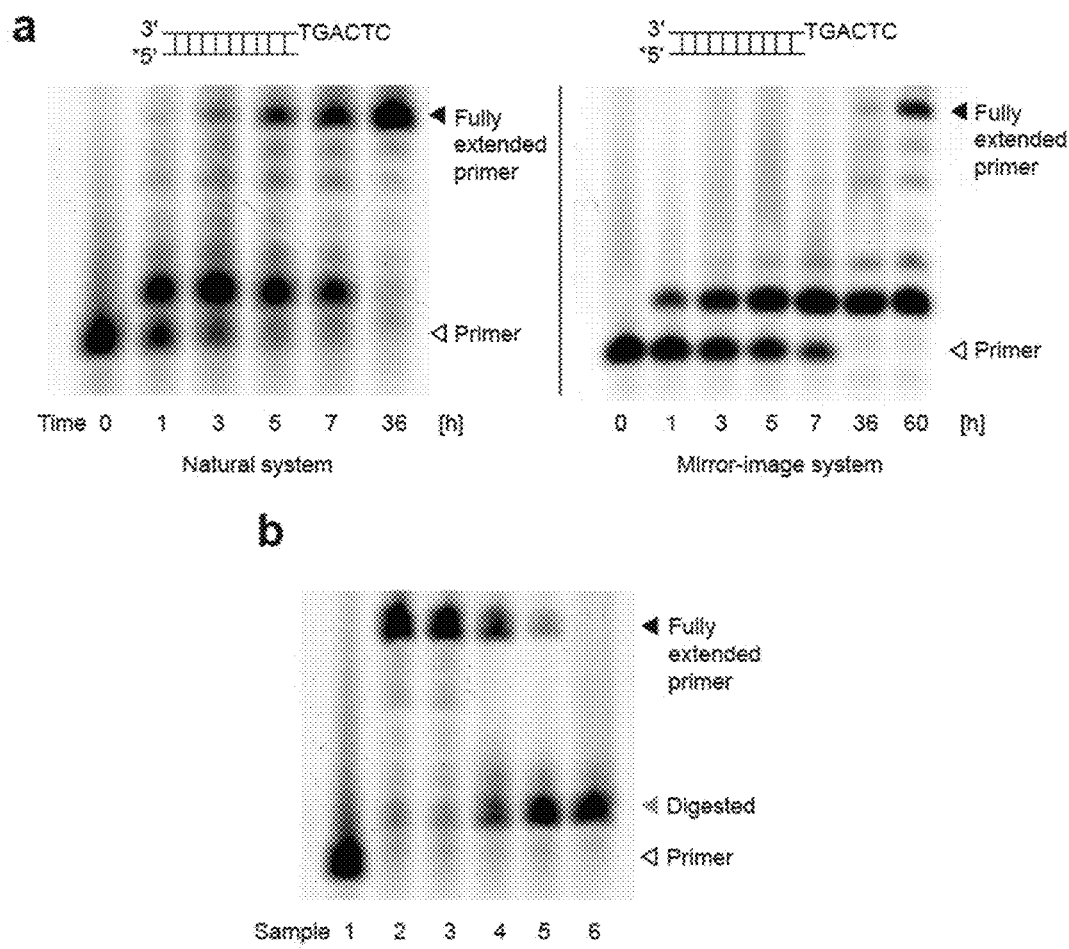
FIG. 12 illustrates DNA template-dependent RNA transcription of the native and mirror-image systems. a. Native and mirror-image ASFV pol X catalyzed RNA transcription. Buffer conditions were 50 mM Tris-HCl, pH 7.5, 20 mM $MgCl_2$, 1 mM DTT, and 50 mM KCl. To a 10 µl reaction system, 0.7 µg of ASFV pol X, 2.5 µM primer, 2.5 µM template and four kinds of 0.4 mM rNTPs were added. 2 units of RNase inhibitor was added to the natural system. The reaction was terminated after reacting at 37° C. for 60 hours. b. The full-length product was obtained after 36 hours of reaction at 37° C. in the natural system with rNTP added. ASFV pol X and RNase inhibitors were inactivated by heating to 75° C. for 10 min. 1 µg/µl, 0.1 µg/µl, and 0.01 µg/µl of RNase A were added to each of the three experiments, followed by incubation at 23° C. for 10 min. The degradation reaction was terminated by addition of 20 units of RNase inhibitor and a loading buffer was added. Reaction products were separated on 8 M urea denatured 20% PAGE gel and imaged using the Typhoon Trio+ system. Sample 1: Control group, extended for 0 hours; Sample 2: The full-length product of D-primer12 extended over 36 hours; Sample 3: The full-length product heated at 75° C. for 10 minutes to inactivate RNase inhibitor and ASFV pol X; Sample 4-6: The full-length extension products were heated at 75° C. for 10 minutes, 0.01 µg/µl, 0.1 µg/µl, or 1 µg/µl of RNase A was added, respectively, and the mixtures were allowed to stand at 23° C. for 10 minutes, and the reaction were terminated by adding 20 units of RNase inhibitor. Electrophoresis was performed on a 20% PAGE gel and the fluorescent signal was scanned with a Typhoon Trio+ scanner. "*" indicates a 5'FAM mark.

In mirror-image ASFV pol X and DNA system, L-rNTPs could also be added to the primer strand, albeit at a slower rate than the native system (FIG. 12a). It was also believed that this might be caused by insufficient purity of the mirror-image template, primer, and rNTPs (impurity peaks could be observed in HPLC, and the amounts of template and primer found in CD were less than the nominal values).

Base Complementary Pairing Specificity of Mirror-Image RNA Transcription System

Figure 13:
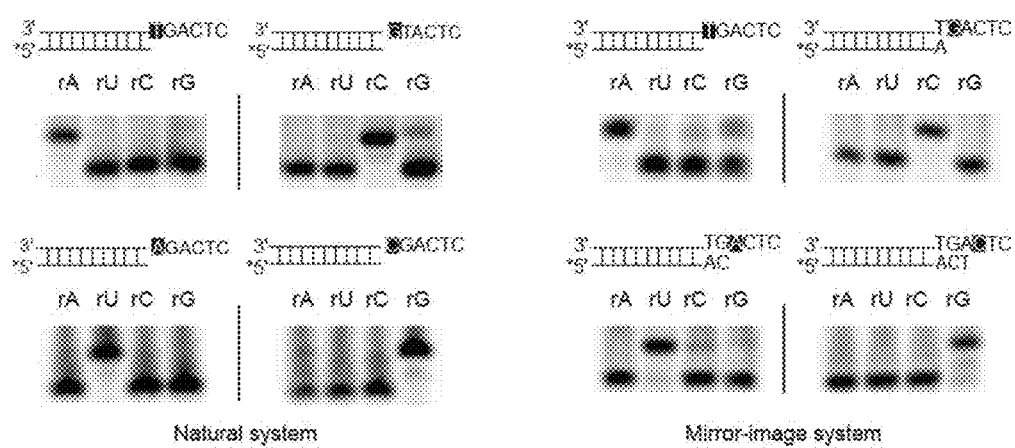
FIG. 13 illustrates the base complementary pairing specificity of native and mirror-image system RNA transcription. In the natural or mirror-image system, one of the corresponding chiral 0.2 mM rATP, rUTP, rCTP, and rGTP was respectively added, and the next base of the template was A, T, C, and G (white box mark on black). Buffer conditions were 50 mM Tris-HCl, pH 7.5, 20 mM $MgCl_2$, 1 mM DTT, and 50 mM KCl. 0.7 µg of corresponding chiral ASFV pol X, 2.5 µM primer, 2.5 µM template18 were added. The reaction was carried out at 37° C. for 12 hours, electrophoresis was performed on a 20% PAGE gel and the fluorescent signal was scanned with a Typhoon Trio+ scanner. "*" indicates a 5'FAM mark. "-" indicates a control group to which D or L-dNTPs were not added.
Figure 15:
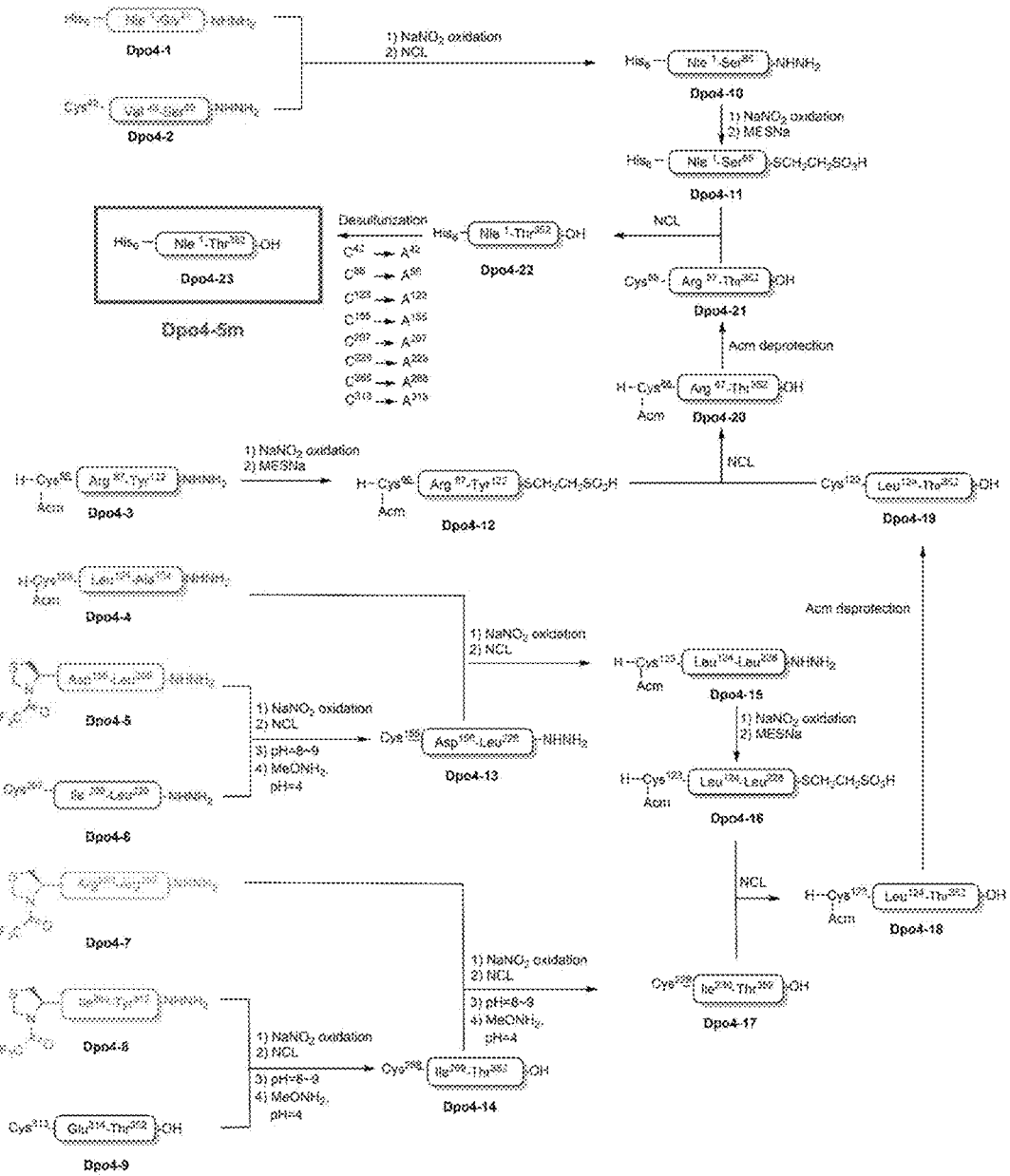
FIG. 15 illustrates the synthetic route of Dpo4-5m. The hydrazide was used instead of the thioester to mediate the assembly of the nine peptide segments in the direction from the C to the N-terminal to finally achieve the total chemical synthesis of Dpo4-5m.

Finally, it was desirable to verify whether the RNA transcription system followed the base complementary pairing rules according to the template. Four kinds of rNTPs were separately added to the reaction system, and the 5'-end FAM-labeled primer12 was used as a primer. It was observed whether it could be extended to 13 nt when the next base of the template was A, T, C, and G, respectively. For the natural system, primer12 and four different templates were used, with the 13$^{th}$ base at the 3' end being A, T, C, and G, respectively. For the mirror-image system, the extension reaction was carried out by adding A, AC and ACT to primer12, and the PAGE gel was recovered to obtain primer13, primer14 and primer15. When they were complementary to template18, the next base on the template was T, G, A, and C, respectively. It was observed that RNTP could be efficiently added to the 3' end of the primer sequence under the four correct pairing conditions of A:U, U:A, C:G, and G:C. Some obvious mismatches occurred in the mirror-image system, such as T:rG, A:rC, and the like, but the efficiency of false nucleoside addition was significantly lower than the correct pairing (FIG. 13). Therefore, the mirror-image RNA transcription system followed the principle of complementary pairing and had a certain degree of fidelity.

BRIEF SUMMARY

The designed and constructed mirror-image chiral genetic information replication and transcription system comprised core components D-ASFV pol X, L-primer, L-template, L-dNTPs/rNTPs, which could be used to amplify DNA and transcribe into RNA according to the template, indicating that the mirror-image chiral polymerase interacts with DNA. Using ASFV pol X polymerase, theoretical multi-cycle amplification of DNA was achieved, and 2.3-fold DNA amplification was achieved from the second cycle to the third cycle. In addition, it was verified that the addition of dNTP or rNTP in the natural and mirror-image system to extend the primer strand follows the base complementary pairing rules and has good fidelity. The polymerase, primer template and dNTPs had chiral specificity in the reaction system. Only when three of them were all natural or all mirror-image molecules, the primer strand could be extended, and other combinations could not achieve amplification. Two chiral DNA replication systems of the same concentration were added to the same solution system, and the two systems were allowed to carry out extension reactions separately without serious mutual hindrance. The 44 nt $Zn^{2+}$-dependent DNAzyme sequence was extended with mirror-image ASFV pol X, and the purified single-stranded L-DNAzyme had self-splicing biological activity in a buffer environment containing 2 mM $Zn^{2+}$.

SUMMARY AND PROSPECTS

Summary

Originating from the exploration of the existence and biological activity of mirror-image biomolecules, our work constructed a mirror-image genetic information replication and transcription system based on D-ASFV pol X. The main conclusions were as follows:

I. A system for mirror-image DNA replication was designed, comprising a mirror-image polymerase, a mirror-image DNA, four mirror-image dNTPs, and appropriate buffer conditions (50 mM Tris-HCl, pH 7.5, 20 mM $MgCl_2$, 1 mM DTT, and 50 mM KCl). The full-length sequence of D-ASFV pol X was obtained by a total chemical synthesis method, and the folding renaturation was successfully carried out by a guanidine hydrochloride denaturation-dialysis method. It was analyzed by HPLC, SDS-PAGE, ESI-MS, CD and the like.

II. In the mirror-image DNA replication system, 0.7 μg of D-ASFV pol X polymerase, 2.5 μM L-template, 2.5 μM L-primer and 0.2 mM L-dNTPs (the concentration for each kind) were added under the above buffer conditions. It was confirmed that replication extension of the mirror-image DNA in multiple template primer combinations (primer12-template18, primer15-template21, primer12-DNAzyme-Template) was possible. And in the DNA replication process, the newly synthesized DNA was complementary to the template strand, and the mirror-image replication process followed the base complementary pairing rules and had good fidelity.

III. Multi-cycle amplification of DNA template could be achieved by adding appropriate template and double-stranded primer to the reaction system, using a PCR cycle of denaturation at 95° C.—annealing at room temperature—extension at 37° C., with additional D-ASFV pol X after each annealing.

IV. In the experiment, the chiral combination of ASFV pol X, primer-template and dNTPs was changed. There were 8 combinations in total, and the extension reaction was tried in a suitable reaction system. Only the all natural combination of L-ASFV pol X, D-primer-template, and D-dNTPs, as well as the all mirror-image combination of D-ASFV pol X, L-primer-template, and L-dNTPs were able to react, and no extension was detected during the reaction time for the remaining six combinations. It was indicated that the natural and mirror-image DNA replication system based on ASFV pol X can recognize the substrate of the wrong chirality and has good chiral specificity in the extension reaction.

V. In the experiment of mixing two chiralities, ASFV pol X, a primer, a template and dNTPs of two chiralities were added to the same reaction system. Each of the two systems can correctly identify the protein or nucleic acid molecule of its own system and complete the extension of the DNA strand respectively, without serious mutual interference.

VI. A 44 nt $Zn^{2+}$-dependent DNAzyme sequence was amplified using a mirror-image DNA replication system and a full-length DNA strand was obtained after 36 hours of extension. The single-stranded DNAzyme was recovered and isolated from PAGE gel. In a buffer environment containing 2 mM $Zn^{2+}$, the L-DNAzyme had self-splicing biological activity, while the control group could not slice under the condition of 20 mM $Mg^{2+}$. The mirror-image DNA replication system can amplify long-chain, active L-DNA sequences.

VII. The mirror-image transcription system comprised D-ASFV pol X, an L-template, an L-primer and L-rNTPs. L-rNTPs can be added to the 3' end of the template under the conditions of 50 mM Tris-HCl, pH 7.5, 20 mM $MgCl_2$, 1 mM DTT, and 50 mM KCl to synthesize an RNA sequence. The reaction rate of D-ASFV pol X template-dependent RNA transcription was lower than that of replicating DNA. The transcription also followed the base-complementary pairing rules, and some mismatches were produced.

Our work enabled the construction of a mirror-image DNA replication and transcription system and demonstrated that the mirror-image polymerase can replicate a mirror-image DNA strand or generate a RNA strand according to the template. Although the evolutionary evidence of the early origins of life has not been found and it is still unknown why the mirror-image molecules have been abandoned in the evolution of higher cell life, it is experimentally confirmed that the mirror-image life molecules can achieve the corresponding biological function, providing the possibility of the existence of the mirror-image molecules. The realization of two important aspects in the mirror-image center rule lays the foundation for building a complete mirror-image life in the laboratory environment in the future.

Applications and Prospects

Our work continued the study of mirror-image chiral biomolecules, not only confirming that the mirror-image molecule has the activity and chiral specificity corresponding to the natural molecule as the researchers expected, but also as the beginning of theoretical and practical applications, completing the two steps in the mirror-image center rule: DNA replication and RNA transcription. The present invention has two main fields of application: one is to use a mirror-image DNA replication system for screening nucleic acid drugs in vitro, and the other is to attempt to construct a complete mirror-image primitive cell.

I. The in vitro mirror-image screening of a nucleic acid drug has a promising future. Both natural and mirror-image nucleic acid sequences can be folded into complex and diverse structures due to their diverse sequences, and some DNA or RNA can bind to specific target molecules and are called an aptamer. Generally, the method for obtaining aptamer is an in vitro screening technique, which uses DNA or RNA containing usually 30-80 random sequences, to generally achieve a complexity of $10^{14}$ or more, with a fixed primer complementary region at both ends to facilitate PCR amplification. In the screening process, the target molecule is usually fixed by different methods, and the random sequence library is placed together with the target molecule for binding, and then the nucleic acid sequence not bound to the target molecule is separated by the washing liquid, and then the nucleic acid with strong affinity is obtained, and the sequence with high affinity intensity is enriched by PCR amplification. After multiple cycles of screening, one or several nucleic acid sequences that bind strongly to the target molecule can be obtained.

If in vitro screening is performed for a disease-related protein or small molecule, such as CDK, GPCR, Bcl-2, etc., it is possible to obtain a nucleic acid aptamer molecule with high affinity for it. However, the effects of clinical application of these molecules are not ideal, and they will be rapidly degraded in the body. Further, researchers hope to use a more stable mirror-image nucleic acid molecule as a drug in the body. At present, existing studies have carried out in vitro screening by synthesizing a mirror-image target molecule and using a natural random sequence library to obtain a natural nucleic acid sequence that can be combined with a mirror-image target. Due to the chiral mirror-image relationship, the same sequence can be used to synthesize the mirror-image genomic aptamer to bind to the natural target (Williams et al., 1997). This screening method can effectively obtain the mirror-image nucleic acid aptamer that can bind a natural molecule, but the problem is that the technology of protein chemical synthesis is very difficult, and few academic or commercial organizations can synthesize complex proteins, and most of the targets in living organisms are beyond the current technical range of protein synthesis, for example, PD-L1 protein has a size of 40 kDa.

The difficulty of mirror-image in vitro screening is that there is currently no way to perform mirror-image PCR amplification in each round of screening. This will be realized by our mirror-image PCR technology. A library of mirror-image random sequences is synthesized by a DNA synthesizer and used directly for the binding of natural drug target. By rinsing, eluting, and amplifying the high affinity sequence, the mirror-image nucleic acid aptamer sequence can be directly obtained through multiple cycles, and can be optimized and clinically tested as potential drug molecule. For mirror-image PCR technology, mirror-image PCR is implemented herein by adding ASFV pol X in each cycle. ASFV pol X has a very low reaction rate (mainly used for repair of genomic gap in virus), and it is not a thermostable polymerase and loses activity at 50° C. for 1 minute under 3.5 M proline-protected condition. In the future, a highly efficient, thermostable polymerase that has been discovered, such as Dpo4 of 352 amino acids (*Sulfolobus solfataricus* P2 DNA polymerase IV), may be used. It is reported in the literature that Dpo4 may be used for PCR amplification, and PCR and mirror-image in vitro screening may be performed using the mirror-image Dpo4 protein.

II. An important step in building a mirror-image life is to implement another important step in the mirror-image center rule, the translation process, in the lab. The mirror-image ribosome and tRNA are the primary biological primitives for translation, and current state of the art still tends to construct using chemical synthesis method. The ribosomes of bacteria contain rRNA, usually with 50-80 ribosomal proteins (Wilson et al., 2009), most of which are shorter than 240 amino acids and can be achieved by current protein synthesis technology. There is also a rpsA protein of 557 amino acids that needs to be achieved by future improved protein synthesis techniques. After each component is synthesized, they are renatured and assembled in vitro to become a functional mirror-image ribosome. By chemically synthesizing DNA and PCR amplification of a longer L-DNA template, a long L-mRNA is transcribed, and the mirror-image ribosome and tRNA can be used to obtain a protein molecule that realizes the functions of a mirror-image cell, such as DNA ligase, helicase, pyruvate dehydrogenase and the like. If the protein and nucleic acid components required for a mirror-image cell are synthesized as much as possible, further technological advances will make it possible to construct simple mirror-image cells, or to use the mirror-image cells to produce mirror-image drugs or mirror-image biomaterials.

| Main symbol comparison table | |
|---|---|
| ASFV pol X | African Swine Fever Virus Polymerase X |
| DNAzyme | Deoxyribozyme |
| SDS-PAGE | Sodium dodecyl sulfate polyacrylamide gel electropheresis |
| Tris | Trishydroxymethylaminomethane |
| NMDA | N-methyl-D-aspartic acid |
| HPLC | High performance liquid chromatography |
| ESI-MS | Electrospray ionization mass spectrometry |
| EDTA | Ethylene diamine tetraacetic acid |
| FAM | Fluorescein amidite |

REFERENCES

Breslow, R., and Levine, M. (2006). Amplification of enantiomeric concentrations under credible prebiotic conditions. Proceedings of the National Academy of Sciences of the United States of America 103, 12979-12980.

Corrigan, J. (1969). D-Amino Acids in Animals. Science 164, 142-149.

Dawson, P. E., and Kent, S. B. H. (2000). Synthesis of Native Proteins by Chemical Ligation. Annual Review of Biochemistry 69, 923-960.

Dawson, P. E., Muir, T. W., Clark-Lewis, I., and Kent, S. B. (1994). Synthesis of proteins by native chemical ligation. Science 266, 776-779.

Engel, M., and Macko, S. (2001). The stereochemistry of amino acids in the Murchison meteorite. Precambrian Research 106, 35-45.

Fields, G. (2002). Introduction to Peptide Synthesis, Vol Chapter 11.

Fitzgerald, M. C., Chernushevich, I., Standing, K. G., Kent, S. B. H., and Whitman, C. P. (1995). Total Chemical Synthesis and Catalytic Properties of the Enzyme Enantiomers L- and D-4-Oxalocrotonate Tautomerase. Journal of the American Chemical Society 117, 11075-11080.

Focher, F., Maga, G., Bendiscioli, A., Capobianco, M., Colonna, F., Garbesi, A., and Spadari, S. (1995). Stereospecificity of human DNA polymerases alpha, beta, gamma, delta and epsilon, HIV-reverse transcriptase, HSV-1 DNA polymerase, calf thymus terminal transferase and *Escherichia coli* DNA polymerase I in recognizing D- and L-thymidine 5'-triphosphate as substrate. Nucleic Acids Research 23, 2840-2847.

Gu, H., Furukawa, K., Weinberg, Z., Berenson, D. F., and Breaker, R. R. (2013). Small, Highly Active DNAs That Hydrolyze DNA. Journal of the American Chemical Society 135, 9121-9129.

Hamase, K., Inoue, T., Morikawa, A., Konno, R., and Zaitsu, K. (2001). Determination of Free [formula omitted]-Proline and [formula omitted]-Leucine in the Brains of Mutant Mice Lacking [formula omitted]-Amino Acid Oxidase Activity. Analytical Biochemistry 298, 253-258.

Hashimoto, A., Kumashiro, S., Nishikawa, T., Oka, T., Takahashi, K., Mito, T., Takashima, S., Doi, N., Mizutani, Y., Yamazaki, T., et al. (1993). Embryonic Development and Postnatal Changes in Free d-Aspartate and d-Serine in the Human Prefrontal Cortex. Journal of Neurochemistry 61, 348-351.

Hashimoto, A., Oka, T., and Nishikawa, T. (1995). Anatomical Distribution and Postnatal Changes in Endogenous Free D-Aspartate and D-Serine in Rat Brain and Periphery. European Journal of Neuroscience 7, 1657-1663.

Joyce, G., Visser, G., Van Boeckel, C., Van Boom, J., Orgel, L., and Van Westrenen, J. (1984). Chiral selection in poly(C)-directed synthesis of oligo (G). Nature 310, 602.

Kent, S. B. (1988). Chemical synthesis of peptides and proteins. Annual Review of Biochemistry 57, 957-989.

Klusmann, S., Nolte, A., Bald, R., Erdmann, V., and Furste, J. (1996). Mirror-image RNA that binds D-adenosine. Nature Biotechnology 14, 1112.

Krause, E., Bienert, M., Schmieder, P., and Wenschuh, H. (2000). The Helix-Destabilizing Propensity Scale of d-Amino Acids: The Influence of Side Chain Steric Effects.

Liu, S., Pentelute, B. L., and Kent, P. S. B. H. (2012). Convergent Chemical Synthesis of [Lysine 24,  38,  83] Human Erythropoietin †. Angewandte Chemie International Edition 51, 993– 999.

Maciejewski, M., Shin, R., Pan, B., Marintchev, A., Denninger, A., Mullen, M., Chen, K., Gryk, M., and Mullen, G. (2001). Solution structure of a viral DNA repair polymerase. Nature Structural & Molecular Biology 8, 936.

Milton, R., Milton, S., and Kent, S. (1992). Total chemical synthesis of a D-enzyme: the enantiomers of HIV-1 protease show reciprocal chiral substrate specificity [corrected]. Science 256, 1445-1448.

Mothet, J., Parent, A., Wolosker, H., Brady, R., Linden, D., Ferris, C., Rogawski, M., and Snyder, S. (2000). d-Serine is an endogenous ligand for the glycine site of the N-methyl-d-aspartate receptor. Proceedings of the National Academy of Sciences of the United States of America 97, 4926.

Nagata, Y., Homma, H., Lee, J., and Imai, K. (1999). d-Aspartate stimulation of testosterone synthesis in rat Leydig cells. FEBS Letters 444, 160-164.

Nolte, A., Klusmann, S., Bald, R., Erdmann, V., and Furste, J. (1996). Mirror-design of L-oligonucleotide ligands binding to L-arginine. Nature Biotechnology 14, 1116.

Ohide, H., Miyoshi, Y., Maruyama, R., Hamase, K., and Konno, R. (2011). d-Amino acid metabolism in mammals: Biosynthesis, degradation and analytical aspects of the metabolic study. Journal of Chromatography B 879, 3162-3168.

Oliveros, M., Yanez, R., Salas, M., Salas, J., Vinuela, E., and Blanco, L. (1997). Characterization of an African Swine Fever Virus 20-kDa DNA Polymerase Involved in DNA Repair. Journal of Biological Chemistry 272, 30899-30910.

Qian, W., and Danishefsky, S. J. (2007). Free-radical-based, specific desulfurization of cysteine: a powerful advance in the synthesis of polypeptides and glycopolypeptides. Angewandte Chemie International Edition 46, 9248-9252.

Sa, N., and Ramsden, D. (2003). Polymerase mu is a DNA-directed DNA/RNA polymerase. Molecular and Cellular Biology 23, 2309-2315.

Schell, M., Molliver, M., and Snyder, S. (1995). D-serine, an endogenous synaptic modulator: localization to astrocytes and glutamate-stimulated release. Proceedings of the National Academy of Sciences of the United States of America 92, 3948-3952.

Sczepanski, J., and Joyce, G. (2014). A cross-chiral RNA polymerase ribozyme. Nature 515, 440.

Showalter, A., Byeon, I., Su, M., and Tsai, M. (2001). Solution structure of a viral DNA polymerase X and evidence for a mutagenic function. Nature Structural & Molecular Biology 8, 942.

Showalter, A., and Tsai, M. (2001). A DNA Polymerase with Specificity for Five Base Pairs.

Vinogradov, A., Evans, E., and Pentelute, B. (2015). Total synthesis and biochemical characterization of mirror image barnase. Chemical Science 6, 2997-3002.

Weinstock, M., Jacobsen, M., and Kay, M. (2014). Synthesis and folding of a mirror-image enzyme reveals ambidextrous chaperone activity. Proceedings of the National Academy of Sciences of the United States of America 111, 11679-11684.

Williams, K., Liu, X., Schumacher, T., Lin, H., Ausiello, D., Kim, P., and Bartel, D. (1997). Bioactive and nuclease-resistant 1-DNA ligand of vasopressin. Proceedings of the National Academy of Sciences of the United States of America 94, 11285-11290.

Wilson, D., Gupta, R., Mikolajka, A., and Nierhaus, K. (2009). Ribosomal Proteins: Role in Ribosomal Functions, Vol 2009.

Wolosker, H., Blackshaw, S., and Snyder, S. (1999). Serine racemase: A glial enzyme synthesizing d-serine to regulate glutamate-N-methyl-d-aspartate neurotransmission. Proceedings of the National Academy of Sciences of the United States of America 96, 13409-13414.

Wyszko, E., Szymanski, M., Zeichhardt, H., Muller, F., Barciszewski, J., and Erdmann, V. (2013). Spiegelzymes: Sequence Specific Hydrolysis of L-RNA with Mirror Image Hammerhead Ribozymes and DNAzymes. PloS one 8, e54741.

Yamaguchi, T., Iwanami, N., Shudo, K., and Saneyoshi, M. (1994). Chiral Discrimination of Enantiomeric 2'-Deoxythymidine 5'-Triphosphate by HIV-1 Reverse Transcriptase and Eukaryotic DNA Polymerases. Biochemical and Biophysical Research Communications 200, 1023-1027.

Zuker, M. (2003). Mfold web server for nucleic acid folding and hybridization prediction. Nucleic Acids Research 31, 3406-3415.

Example 2

Total Chemical Synthesis of a Thermostable DNA Polymerase

Polymerase chain reaction (PCR) is an important tool for modern biological research. To achieve a polymerase chain reaction of the mirror-image life system, a thermostable DNA polymerase is designed and chemically synthesized. The enzyme is DNA polymerase IV (Dpo4) from *Sulfolobus solfataricus* P2 strain consisting of 352 amino acid residues. This chemically synthesized L-DNA polymerase is the synthetic protein with the largest molecular weight reported to date. After optimization of the PCR reaction system, the artificially synthesized L-Dpo4 enzyme was used to amplify a DNA sequence of up to 1.5 Kb. The establishment of the chemical synthesis route of L-Dpo4 enzyme has laid a solid foundation for the later synthesis of D-DNA polymerase suitable for mirror-image PCR, which may open up a new path for discovering more mirror-image molecular tools.

In previous study, mirror-image African Swine Fever Virus Polymerase X (D-ASFV pol X) containing 174 D-amino acid residues was chemically synthesized, and replication and transcription of mirror-image DNA were successfully achieved by the enzyme [1]. However, due to the poor processivity of the ASFV pol X enzyme, only a 44 nt $Zn^{2+}$-dependent self-cleaving L-form deoxyribozyme (DNAzyme) could be obtained by a primer extension experiment [1]. In addition, since ASFV pol X is not thermostable, it was only applied to a conceptual mirror-image gene replication chain reaction experiment, that is, by supplying fresh enzyme in each cycle [1], which made the enzyme unable to efficiently amplify L-DNA, thereby limiting its use in the mirror-image life system.

In order to achieve efficient amplification of the mirror-image DNA, a more efficient and thermostable mirror-image polymerase may be obtained by directional engineering of the current L-ASFV pol or by searching for and developing a new synthetic route. The most commonly used Taq DNA polymerase in PCR reactions has 832 amino acid residues, but the largest protein synthesized by a chemical method to date contains only 312 amino acid residues, so it is difficult to synthesize Taq DNA polymerase by total chemical synthesis. However, the thermostable DNA polymerase IV (Dpo4) from *Sulfolobus solfataricus* P2 strain not only can PCR-amplify a DNA sequence of up to 1.3 kb [3], but also contains only 352 amino acid residues, so we began to explore the chemical synthesis route of Dpo4 enzyme.

Result:

Design of Total Chemical Synthesis of Mutant Dpo4 Enzyme

Since the peptide chain directly synthesized by solid phase peptide synthesis (SPPS) generally does not exceed 50 amino acid residues, the natural chemical ligation (NCL) method [4, 5] was used to ligate short polypeptide segments into a long polypeptide segment through natural peptide bonds. This method requires a cysteine (Cys) residue at the N-terminus of the ligation site, whereas only one cysteine (Cys31) is present in the wild-type (WT) Dpo4 amino acid sequence (FIG. 14*a*). In the absence of a cysteine ligation site, several alanine (Ala) sites were searched for in the sequence, replaced by cysteine during chemical synthesis, and then cysteine was reconverted to alanine by a non-metal free radical desulfurization method after the ligation was complete. In the original sequence, A42, A155, A229 and A268 can be used as the ligation sites for this method. However, even if these four alanine residues were used as the ligation site, most of the polypeptide segments were greater than 50 amino acid residues, so in order to introduce more available ligation sites in the amino acid sequence of this enzyme, four point-mutations (S86A, N123A, S207A and S313A) were introduced in the original amino acid sequence (FIG. 14*b*). In addition, in order to avoid the formation of a dimer of the protein molecule through a disulfide bond during the folding process, a C31S mutation was additionally introduced. The recombinant polymerase containing these five mutations was expressed and purified in *E. coli* and tested for activity. The experiment showed that the five-point mutations (C31S, S86A, N123A, S207A and S313A) did not affect PCR activity of the enzyme (FIG. 16*b*).

With these five point-mutations, a cyanoguanidine-based natural chemical ligation method (FIG. 15) was used to assemble 9 polypeptide segments (Dpo4-1 to Dpo4-9) in the direction from the C to the N-terminal, thereby achieving the total chemical synthesis of Dpo4-5m polymerase [5, 7, 8]. To avoid oxidation of the amino acid side chain during SPPS and protein ligation, the methionine residues (Met1, Met76, Met89, Met157, Met216 and Met251) originally-presented in the protein were replaced with norleucine (Nle). Since norleucine is isosteric with methionine, the replacement of methionine by norleucine has little effect on protein structure and function [9]. In addition, a histidine tag (His6) was added to the N-terminus of the synthetic enzyme to further purify the protein in subsequent experiments. This resulted in a total length of 358 amino acids (352 amino acids of the polymerase plus 6 amino acids of the His6 tag; see FIG. 14b) in the final synthesized polypeptide (Dp4-5m).

Chemical Synthesis of Dpo4-5m

All peptide segments ranging in length from 22 to 52 amino acids were synthesized by Fmoc-based solid phase peptide synthesis and purified by reverse phase high performance liquid chromatography (RP-HPLC). During the synthesis of peptides by solid phase peptide synthesis, the unmodified peptides Dpo4-1 and Dpo4-3 were found to be highly hydrophobic and their solubility in aqueous acetonitrile was very low. It has been reported in the literature that the incorporation of an isoacyl dipeptide into a peptide segment can increase the water solubility of the peptide [10, 11], and a traceless modification can be achieved due to rapid O-to-N acyl shift under natural chemical ligation conditions at pH ~7 [10, 11]. Thus, an isoacyl dipeptide was inserted between Val30-Ser31 (in peptide Dpo4-1) and Ala102-Ser103 (in peptide Dpo4-3). The experimental results showed that the incorporation of the isoacyl dipeptide improved not only the solubility of the peptide segment, but also improved the purity of the polypeptide. In addition, acetamidomethyl (Acm) was also used to protect the N-terminal Cys of the peptide segments Dpo4-3 and Dpo4-4, thus preventing cyclization of the peptide segments during ligation and Cys desulfurization [12]. At the same time, trifluoroacetylthiazolidine-4-carboxylic acid (Tfa-Thz) was introduced as a protective group for N-terminal Cys in the peptide segments Dpo4-5, Dpo4-7 and Dpo4-8. Tfa-Thz is compatible with hydrazide oxidation and can be rapidly converted back to Thz under alkaline conditions. Therefore, the N-terminal Cys unprotected peptide segments Dpo4-13, Dpo4-14 and Dpo4-17 could be conveniently obtained by a one-pot strategy of natural chemical ligation and Tfa-Thz deprotection (see Appendix).

Figure 16:
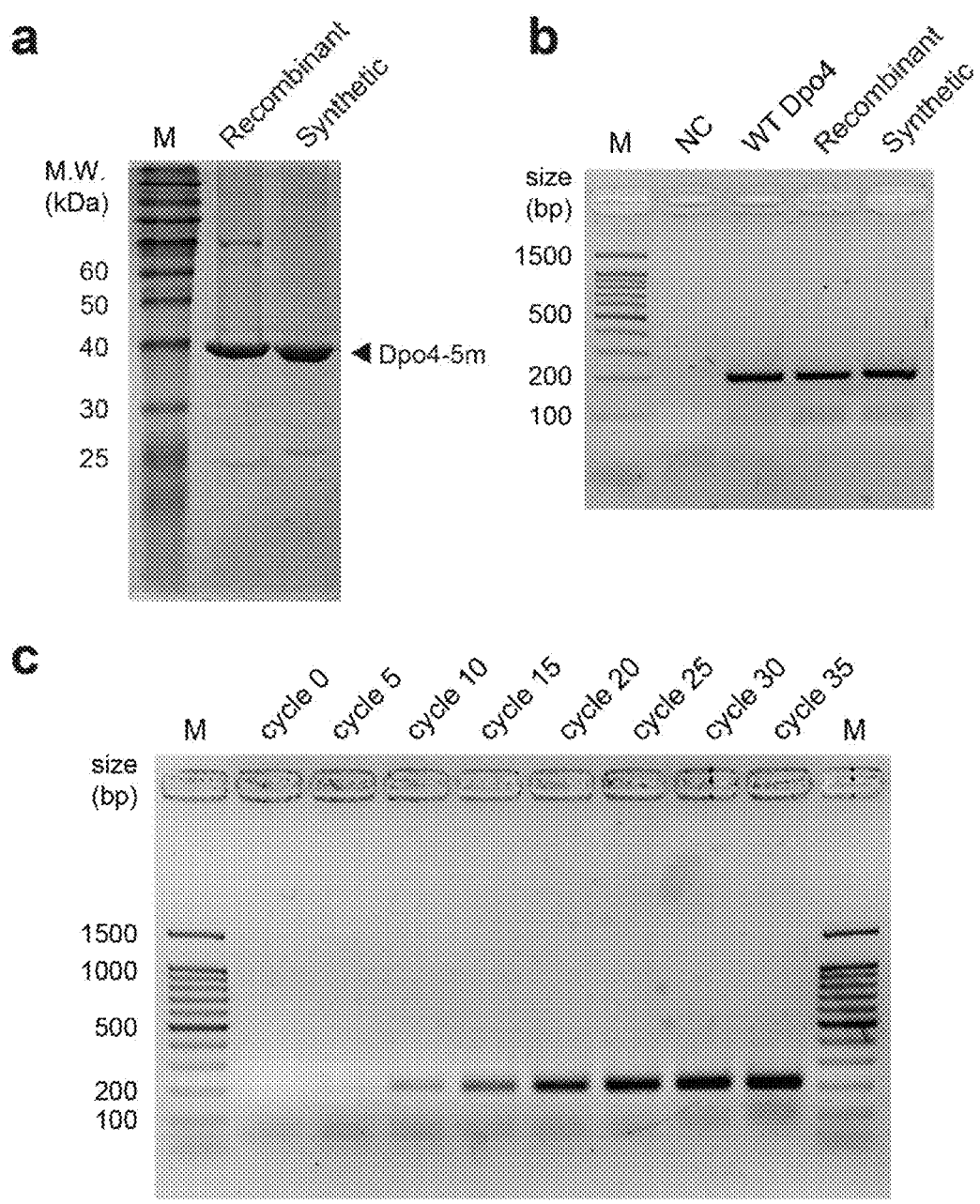
FIG. 16 illustrates the biochemical properties of Dpo4-5m polymerase. (a) The molecular weight and purity of the chemically synthesized Dpo4-5m polymerase and purified recombinant Dpo4-5m polymerase expressed from E. coli strain BL21 (DE3) were analyzed using 12% SDS-PAGE, and stained with Coomassie blue. A small amount of unligated peptide was observed in the synthesized Dpo4-5m. M was a standard molecular weight protein marker. (b) A 200 bp DNA sequence was PCR amplified using recombinant wild-type Dpo4 (labeled as "WT Dpo4" in the figure), recombinant mutant Dpo4-5m ("Recombinant") and synthetic mutant Dpo4-5m ("Synthetic") polymerase. The PCR reaction system contained 50 mM HEPES (pH 7.5), 5 mM $MgCl_2$, 50 mM NaCl, 0.1 mM EDTA, 5 mM DTT, 10% glycerol, 3% DMSO, 0.1 mg/ml BSA, 200 µM ultrapure dNTPs, 0.5 µM bidirectional primer, 2 nM linear double stranded DNA template and approximately 300 nM Dpo4-5m enzyme. After 35 cycles of reaction, the PCR product was analyzed by 2% agarose gel electrophoresis and stained with GoldView (Solarbio). NC was a negative control experiment in which only template and primer were present in the reaction system, and no polymerase. (c) The 200 bp DNA products were obtained from different cycles of amplification using synthetic Dpo4-5m. The PCR products were analyzed by 2% agarose gel electrophoresis and stained with GoldView (Solarbio), and the numbers above the lane represent the numbers of cycles of amplification. M was a standard molecular weight DNA marker.

By assembling 9 peptide segments in the direction from C-terminal to N-terminal using natural chemical ligation [5, 7, 8], a synthetic peptide segment containing 358 amino acids was obtained with a final yield of 16 mg (FIG. 19-32). The molecular weight of the obtained full-length peptide was analyzed by analytical reversed-phase high performance liquid chromatography (HPLC) and electrospray ionization mass spectrometry (ESI-MS) to be 40797.5 Da, and the theoretical value was 40799.9 Da (FIG. 32B, C). The lyophilized peptide segment powder was dissolved in a denaturing buffer containing 6 M guanidine hydrochloride, and then correct folding of the peptide segment was achieved with the aid of successive dialysis against a series of renaturation buffers containing 4 M, 2 M, 1 M and 0 M guanidine hydrochloride. The folded polymerase was then heated to 78° C., and the thermally labile peptide segments and the incorrectly folded full-length peptide segments were aggregated at this temperature and could be removed by ultracentrifugation. The fully-folded synthetic Dpo4-5m polymerase was present in the supernatant due to its thermal stability, purified by a Ni-NTA column and concentrated by a centrifugal filter. The concentrated Dpo4-5m polymerase was analyzed for molecular weight and purity by SDS-PAGE (FIG. 16a). At the same time, the amino acid sequence was determined by LC-MS/MS mass spectrometry, and two independent mass spectrometry sequencing experiments were carried out by treated with trypsin and pepsin. The results of the two experiments covered 100% of the sequences (see Table S2).

PCR Reaction Using Chemically Synthesized Dpo4-5m Polymerase

The PCR activity of Dpo4-5m polymerase prepared by the above method was first detected using a 200 bp template. As shown in FIG. 33, by comparing the relative amounts of PCR products of different cycle times, it was found that the PCR amplification efficiency was about 1.5, which was substantially comparable to that of the wild-type and mutant polymerases obtained by recombinant expression. Subsequently, the PCR product amplified for 35 cycles was cloned into the T vector for Sanger sequencing, and the alignment with the original sequence showed that there were 7 single base deletions and 19 single base mutations in the 22 clones tested (FIG. 34). The result indicated that the cumulative mutation rate after 35 cycles was about 0.9%, which was basically consistent with the replication error rate of wild-type Dpo4 polymerase reported in the literature [3, 14].

Figure 17:
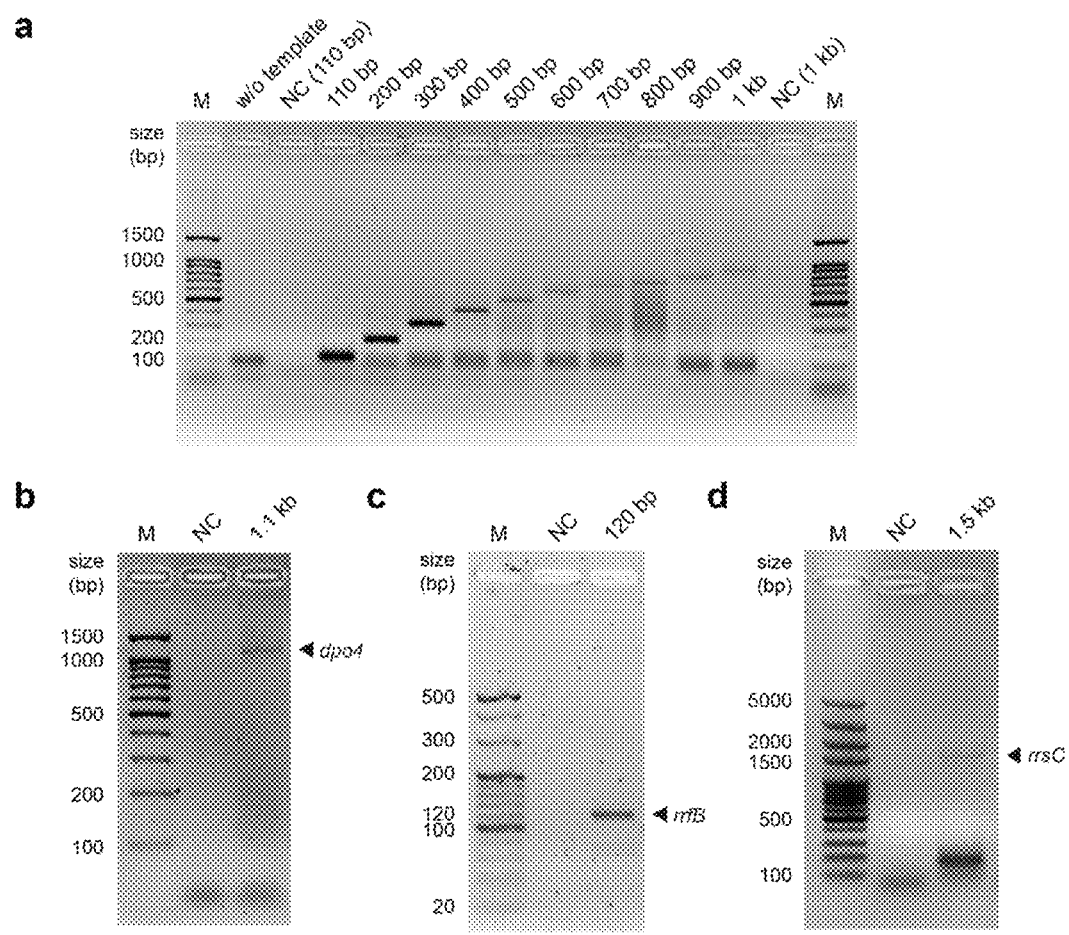
FIG. 17 illustrates the PCR amplification of DNA sequences of different lengths using chemically synthesized Dpo4-5m polymerase. (a) The synthesized Dpo4-5m polymerase was used to PCR amplify sequences with lengths from 110 bp to 1 kb, with 35 cycles per reaction. The extension time for each cycle of amplification of the 110-300 bp sequence was set to 2 minutes, the sequence of 400-600 bp was extended for 5 minutes, and the sequence of 700-

Subsequently, Dpo4-5m polymerase was used to amplify DNA sequences of different lengths. As shown in FIG. 17a, PCR products of different lengths from 110 bp to 1.0 kb can be amplified in 35 cycles, and the PCR amplification efficiency gradually decreases as the template length increases. In this experiment, the PCR reaction conditions were basically the same, and the extension time varied with the length of the template. For 110 to 300 bp segments, the extension time was set to 2 minutes per cycle, 5 minutes for 400 to 600 bp, and 10 minutes for 700 to 1000 bp.

Based on the ability of Dpo4-5m to amplify a 1.0 kb DNA fragment, PCR amplification of a 1.1 kb dpo4 gene fragment was attempted and successfully performed (FIG. 17b), which was the coding gene for Dpo4 polymerase itself. In addition, the 120 bp E. coli 5s rRNA gene rrfB and the 1.5 kb E. coli 16S rRNA gene rrfC were also successfully amplified. These genes can be used to transcribe the corresponding ribosomal RNA (rRNA) and are therefore important for the assembly of mirror-image ribosomes [15]. The 1.5 kb amplified fragment obtained by this method exceeded the longest fragment (1.3 kb) amplified by the wild type Dpo4 polymerase reported in the prior literature.

Assembly PCR Reaction Using Chemically Synthesized Dpo4-5m Polymerase

Assembled PCR is a method by which long DNA oligonucleotide strands that cannot be efficiently synthesized by chemical synthesis (usually less than 150 nt) can be obtained. This method can be used to obtain long mirror-image gene sequences, considering the lack of available L-DNA template sequences in nature. The 198 bp tC19Z gene was successfully assembled using Dpo4-5m polymerase, which encodes an in vitro evolved ribozyme with RNA polymerase activity using RNA as a template [17]. Two PCR primers (tC19Z-F115 and tC19Z-R113) with an overlapping sequence of 30 bp were used for PCR amplification reaction. After 20 cycles, both the experimental group and the negative control group (no enzyme) were digested with exonuclease I (Exo I), which can only digest single-stranded DNA but not double-stranded DNA, so only the assembled full-length double-stranded DNA remained in the final reaction system. The result of agarose electrophoresis in FIG. 18a showed that the full-length 198b double-stranded DNA was successfully assembled in this experiment, and its product sequence was also verified by sanger sequencing.

Meanwhile, an attempt was made to use six short primers between 47 nt and 59 nt in length to perform a three-step assembly PCR for amplification to obtain the 198 bp tC19Z gene sequence. (FIG. 18c). Such an amplification strategy can be applied in the future in a mirror-image PCR system, and a full-length L-form gene sequence can be finally assembled starting from a short oligonucleotide primer strand. In this experiment, the first step was to perform five cycles of assembly PCR with tC19Z-F1 and tC19Z-R1 primers; the second step was to use the assembled PCR product of the first step as a template to amplify 10 cycles with primers tC19Z-F2 and tC19Z-R2; and the last step was to use the product of the second step as a template to amplify 20 cycles with the primers tC19Z-F3 and tC19Z-R3 to obtain the final full-length product. Agarose gel electrophoresis analysis showed that the amplification products of lengths of 88 bp, 162 bp and 198 bp were respectively obtained by each step of the three-step PCR reaction (FIG. 18d), and the final full-length product was also verified by sanger sequencing. A one-step PCR reaction was also attempted using six primers simultaneously, but this method produced multiple by-product bands.

Discuss:

The previously reported ASFV pol X-based mirror-image genetic replication system lacked processivity and thermostability, making it impossible to perform efficient PCR amplification experiments to obtain longer L-DNA sequences [1]. Therefore, in order to realize the PCR of the mirror-image system, a mutant Dpo4 polymerase capable of performing PCR reaction was designed and chemically synthesized, which also laid a solid foundation for the synthesis of D-DNA polymerase suitable for mirror-image system PCR. The efficient mirror-image PCR system thus created can generate many mirror-image molecular tools. For example, a chirally inverted PCR system can be used for in vitro screening of mirror-image nucleic acid aptamers (mirror-image Systematic Evolution of Ligands by Exponential Enrichment, miSELEX) to screen for L-form nucleic acid aptamer that specifically bind to a biological target, and is expected to be a tool for research and treatment.

A major challenge in the development of mirror-image PCR tools is to obtain long DNA template sequences. The synthetic Dpo4-5m solves this problem by using short chemically synthesized oligonucleotides for assembly PCR. However, since the synthetic Dpo4-5m polymerase has a low amplification efficiency for longer templates, it is still difficult to obtain a mirror-image gene larger than 1 kb such as 16S and 23S rRNA. In the future, it may be necessary to develop efficient mirror-image DNA or RNA ligase to solve this problem, for example, through either total chemical synthesis of a nucleic acid ligase consisting of D-form amino acids, or utility of a ribozyme having a cross-mirror-image ligase activity [20].

Although the final yield of Dpo4-5m polymerase based on the developed chemical synthesis route can reach 16 mg, it is still not a practical method for industrial large-scale production of D-form enzymes. In the future, the synthetic route can be further optimized with the use of other ligation methods [21-23], or a truncated Dpo4 polymerase can be designed for total chemical synthesis.

In addition, another strategy for achieving efficient mirror-image PCR is to look for other polymerase systems other than Dpo4 polymerase. Besides its low efficiency of amplification with long DNA sequences, Dpo4 polymerase has another disadvantage of low fidelity with a replication error rate between $4\times10^4$ and $8\times10^{-3}$ [3, 14]. mirror-image A more efficient mirror-image PCR system can be achieved by continuing to search for other thermostable DNA polymerases with low molecular weight, or by directed modification of a DNA polymerase with low molecular weight to achieve thermal stability and high amplification efficiency [24,25].

Materials and Methods:

9-Fluorenylmethoxycarbonyl (Fmoc)-Based Solid Phase Peptide Synthesis (Fmoc-SPPS)

All peptide segments were artificially synthesized. Amino acid coupling was carried out using either 4 eq. Fmoc-amino acid, 4 eq. ethyl cyanoglyoxylate-2-oxime (Oxyma) and 4 eq. N,N'-diisopropylcarbodiimide (DIC) in DMF, or 4 eq. Fmoc-amino acid, 3.8 eq. O-(6-chloro-benzotriazol-1-yl)-N,N,N',N'-tetramethyluronium hexafluorophosphate (HCTU) and 8 eq. N,N-diisopropylethylamine (DIEA) in DMF. Air-bath heating was used to accelerate the reaction when needed [26]. Peptide segment Dpo4-9 was synthesized on Fmoc-Thr(tBu)-Wang resin (GL Biochem). Other peptide segments were synthesized on Fmoc-hydrazine 2-chlorotrityl chloride resin to prepare peptide hydrazides [27]. Val30-Ser31 (in segment Dpo4-1) and Ala102-Ser103 (in segment Dpo4-3) were coupled as isoacyl dipeptides. Tfa-Thz-OH was coupled using Oxyma/DIC activation at room temperature. After the completion of peptide chain assembly, the peptide segment was cleaved from the resin using a cleavage reagent (water/benzyl sulfide/triisopropylsilane/1,2-ethanedithiol/trifluoroacetic acid in a ratio of 0.5/0.5/0.5/0.25/8.25). After bubbling with nitrogen, the polypeptide was precipitated by adding ice diethyl ether, and finally centrifuged to collect a solid precipitate to obtain a crude polypeptide.

Natural Chemical Ligation (NCL)

The polypeptide segment containing a hydrazide group at C-terminus was dissolved in an acidified ligation buffer (6 M guanidine hydrochloride and 0.1 M sodium dihydrogen phosphate, pH 3.0). The mixture was placed in an ice salt bath (−15° C.), 10 to 20 eq. $NaNO_2$ solution was added thereto, and then stirred and reacted for 30 minutes. Subsequently, 40 eq. 4-mercaptophenylacetic acid (MPAA) and 1 eq. polypeptide segment with N-terminal cysteine were then added and the pH of the system was adjusted to 6.5 at room temperature. After overnight reaction, the system concentration was diluted by a factor of two by adding 100 mM trichloroethyl phosphate (TCEP) buffer, and then reacted at room temperature for 1 hour under stirring. The target product was finally isolated using semi-preparative grade RP-HPLC. The ligation product was analyzed by HPLC and ESI-MS and purified by semi-preparative HPLC.

Protein Renaturation and Purification

The lyophilized Dpo4-5m polymerase powder was dissolved in a denaturing buffer containing 6 M guanidine hydrochloride, followed by dialysis against a series of renaturation buffers containing 4 M, 2 M, 1 M and 0 M guanidine hydrochloride, respectively, and each step of dialysis was carried out at 4° C. for 10 hours under gently stirring. The denaturation and renaturation buffer also contained 50 mM Tris-HCl (pH 7.5), 50 mM NaAc, 1 mM DTT, 0.5 mM EDTA and 16% glycerol. After renaturation, the enzyme was dialyzed against a buffer containing 10 mM potassium phosphate (pH 7.0), 50 mM sodium chloride, 10 mM magnesium acetate, 10% glycerol and 0.1% 2-mercaptoethanol. The folded polymerase was heated to 78° C. to precipitate the thermolabile peptide segment, which was then removed by ultracentrifugation (19,000 rpm) for 40 minutes at 4° C. The supernatant was added to Ni-NTA resin (Qiagen) and incubated overnight at 4° C., followed by purification as previously described, but not further purified using a Mono S column [28]. After purification, the absorbance of the protein at a wavelength of 280 nm was measured using a spectrophotometer, and the extinction coefficient was set to 24,058 $M^{-1}$ $cm^{-1}$, and the molecular weight was set to 40.8 kDa. The purity and yield of the synthesized polymerase (about 100 µg) and recombinant enzyme were finally analyzed using 12% SDS-PAGE.

PCR Reaction Using Chemically Synthesized Dpo4-5m Polymerase

The PCR reactions described herein were carried out in a 20 µl system containing 50 mM HEPES (pH 7.5), 5 mM $MgCl_2$, 50 mM NaCl, 0.1 mM EDTA, 5 mM DTT, 10% glycerol, 3% DMSO, 0.1 mg/ml BSA, 200 µM ultrapure dNTPs, 0.5 µM bidirectional primers, 2 nM linear double stranded DNA template and approximately 300 nM Dpo4-5m polymerase. The PCR program was set to denaturation at 86° C. for 3 minutes; followed by 35 cycles of denaturation at 86° C. for 30 seconds, annealing at 58-65° C. for 1 minute (annealing temperature depending on primer Tm value), extension at 65° C. for 2 to 15 minutes (extension time is determined by the length of the amplicon), and last extension at 65° C. for 5 minutes. In experiments in which DNA sequences of different lengths were amplified, the same primers (M13-long-F and M13-long-R, see Table S1) were used for PCR, and the extension time for the templates of 110-300 bp was 2 minutes, 5 minutes for the templates of 400-600 bp and 10 minutes for the templates of 700-1000 bp. After the completion of PCR, the PCR products were analyzed by 2% agarose gel electrophoresis and stained with GoldView (Solarbio). In an experiment to test the amplification efficiency and fidelity of Dpo4-5m, a linear double-stranded DNA with a length of 200 bp prepared by Q5 DNA polymerase (New England Biolabs) was used as a template and the product bands of the first 10 cycles were analyzed using Image Lab software (Bio-Rad) to analyze their amplification efficiency. The PCR product after 35 cycles was purified using the DNA Clean & Concentrator kit (Zymo Research) and then cloned into the T vector for sanger sequencing to analyze its fidelity.

Assembly PCR Using Synthetic Dpo4-5m

The assembly PCR reaction was carried out using two primers sharing a 30 bp overlapping region, with a length of 115 nt and 113 nt (tC19Z-F115 and tC19Z-R113), respectively (Supplementary Table S1). No other template was added to the reaction, the target product was the 198 bp tC19Z gene, and no enzyme was added to the negative control group. After 20 cycles of reaction, the products of the experimental group and the control group were treated with exonuclease I at 37° C. for 10 minutes (10 U per 5 µl of PCR product). In an experiment wherein a three-step method was used to assemble the 198 bp tC19Z gene using six short primers, the first step used primers tC19Z-F1 and tC19Z-R1, the second step used primers tC19Z-F2 and tC19Z-R2, and the third step used primers tC19Z-F3 and tC19Z-R3. The PCR product of the previous step served as a template for the next reaction, accounting for about 5% of the next reaction system. The numbers of cycles of the first, second, and third steps of the PCR reaction were 5, 10, and 20, respectively. After the completion of the PCR reaction, the product was analyzed using 3% high resolution agarose gel electrophoresis and stained with GoldView (Solarbio). The resulting full-length product was purified and recovered using the DNA Clean & Concentrator kit (Zymo Research) and then cloned into the T vector for sanger sequencing.

APPENDIX

Total Chemical Synthesis of Thermostable DNA Polymerase Material:
Chemicals and Reagents

| | |
|---|---|
| 9-fluorenylmethoxycarbonyl-amino acid | GL Biochem (Shanghai) and CSbio (Shanghai) |
| Boc-Cys(Acm)-OH, Boc-Cys(Trt)-OH | GL Biochem (Shanghai) |
| 6-chlorobenzotriazole-N,N,N',N'-tetramethyluron hexafluorophosphate | GL Biochem (Shanghai) |
| Anhydrous 1-hydroxybenzotriazole (HOBt) | GL Biochem (Shanghai) |
| N,N'-diisopropylcarbodiimide (DIC) | Adamas |
| Ethyl cyanoacetaldehyde-2-oxime (Oxyma) | Adamas |
| DL-1,4-dithiothreitol (DTT) | Adamas |
| N,N-dimethylformamide (DMF) | J&K Scientific |
| Trifluoroacetic acid (TFA) | J&K Scientific |
| Triisopropylsilane (TIPS) | J&K Scientific |
| 1,2-ethanedithiol (EDT) | J&K Scientific |
| Benzaldehyde | J&K Scientific |
| Sodium 2-mercaptoethanesulfonate (MESNa) | J&K Scientific |
| Palladium chloride | J&K Scientific |
| 2,2'-azobis[2-(2-imidazolin-2-yl)propane] dihydrochloride (VA-044) | J&K Scientific |
| N,N-diisopropylethylamine (DIEA) | Beijing Ouhe Technology |
| Dichloromethane (DCM) | Beijing Chemical Industry Group |
| Sodium nitrite | Sinopharm |
| Sodium monohydrogen phosphate dodecahydrate | Sinopharm |
| Piperidine | Sinopharm |
| Ether | Sinopharm |
| Acetic acid | Sinopharm |
| Silver acetate | Sinopharm |
| Sodium dihydrogen phosphate dihydrate | Sinopharm |
| Sodium hydroxide | Sinopharm |
| Guanidine hydrochloride | Sinopharm |
| Hydrochloric acid | Sinopharm |
| Sodium chloride | Sinopharm |
| 4-mercaptophenylacetic acid (MPAA) | Alfa Aesar (Heysham, England) |
| Tris(2-carboxyethyl)phosphine hydrochloride (TCEP•HCl) | Tianjin Liankuan Fine Chemical |
| Reduced glutathione (GSH) | Acros Organics (Belgium) |
| Acetonitrile (HPLC grade) | J. T. Baker (New Jersey, U.S.) |

Experimental Method:

Reversed-phase high performance liquid chromatography (HPLC) and electrospray ionization mass spectrometry (ESI-MS)

The product was analyzed and purified by reverse-phase high performance liquid chromatography using a Shimadzu Prominence HPLC system (solvent delivery unit: LC-20AT), in combination with C4 and C18 columns produced by Welch, and the mobile phase was water and acetonitrile (both contain 0.1% TFA). Electrospray ionization mass spectrometry was obtained using a Shimadzu LCMS-2020 liquid chromatography mass spectrometer.

Liquid Chromatography-Secondary Mass Spectrometry (LC-MS/MS) for Peptide Segment Sequencing The artificially synthesized Dpo4-5m was purified by 12% SDS-PAGE, and trypsin or pepsin was added for overnight digestion at 37° C. in the gel, and the extracted peptide segment was analyzed by LC-MS. The sample was separated by a Thermo-Dionex Ultimate 3000 HPLC system directly coupled to a Thermo Scientific Q Exactive mass spectrometer and eluted at a flow rate of 0.3 µl/min. The analytical column was a self-made fused silica capillary column (75 µm ID, a length of 150 mm; Upchurch, Oak Harbor) filled with C-18 resin (300 Å, 5 µm, Varian, Lexington, Mass., U.S.). The Q Exactive mass spectrometer operated under data-dependent acquisition mode by the Xcalibur 2.1.2 software with a single full-scan mass spectrum in the Orbitrap (300-1800 m/z, 70,000 resolution) followed by 20 data-dependent MS/MS scans at 27% normalized collision energy.

| Annexed table S1 | Primer Sequence |
|---|---|
| Primer | Sequence |
| M13-long-F | 5'-GTAAAACGACGGCCAGTGAATTAGAACTCGGT-3' |
| M13-long-R | 5'-CAGGAAACAGCTATGACCATGATTACGCCAAGTTT-3' |
| 5s rRNA(rrfB)-F | 5'-TGCCTGGCGGCAGTAGCGC-3' |
| 5s rRNA(rrfB)-R | 5'-ATGCCTGGCAGTTCCCTACTCTCGC-3' |
| 16s rRNA(rrsC)-F | 5'-AAATTGAAGAGTTTGATCATGGCTCAGATTGAACGCTGG-3' |
| 16s rRNA(rrsC)-R | 5'-TAAGGAGGTGATCCAACCGCAGGTTCC-3' |
| dpo4-F | 5'-ATGATTGTTCTTTTCGTTGATTTTGACTACTTT-3' |
| dpo4-R | 5'-AGTATCGAAGAACTTGTCTAATCCTATTGCT-3' |
| tC19Z-F115 | 5'-GTCATTGAAAAAAAAAGACAAATCTGCCCTCAGAGCTTGAGAACATCTTCGGATGCAGAGGAGGCAGCCTTCGGTGGCGCGATAGCGCCAACGTTCTCAACAGACACCCAATACT-3' |
| tC19Z-R113 | 5'-GGAGCCGAAGCTCCGGGGATTATGACCTGGGCGTGTCTAACATCGCCTTTTCGTCAGGTGTTATCCCCACCCGCCGAAGCGGGAGTATTGGGTGTCTGTTGAGAACGTTGGCG-3' |
| tC19Z-F1 | 5'-AGAGGAGGCAGCCTTCGGTGGCGCGATAGCGCCAACGTTCTCAACAGACACCCAATACT-3' |
| tC19Z-R1 | 5'-CAGGTGTTATCCCCACCCGCCGAAGCGGGAGTATTGGGTGTCTGTTGAGAACGTTGGCG-3' |
| tC19Z-F2 | 5'-CAAATCTGCCCTCAGAGCTTGAGAACATCTTCGGATGCAGAGGAGGCAGCCTTCGGTGG-3' |
| tC19Z-R2 | 5'-ATTATGACCTGGGCGTGTCTAACATCGCCTTTTCGTCAGGTGTTATCCCCACCCGCCGA-3' |
| tC19Z-F3 | 5'-GTCATTGAAAAAAAAAGACAAATCTGCCCTCAGAGCTTGAGAACATCTTCG-3' |
| tC19Z-R3 | 5'-GGAGCCGAAGCTCCGGGGATTATGACCTGGGCGTGTCTAACATCGCC-3' |

REFERENCES

1. Wang, Z., et al., *A synthetic molecular system capable of mirror-image genetic replication and transcription.* Nat Chem, 2016. 8(7): p. 698-704.
2. Weinstock, M. T., M. T. Jacobsen, and M. S. Kay, *Synthesis and folding of a mirror-image enzyme reveals ambidextrous chaperone activity.* Proceedings of the National Academy of Sciences of the United States of America, 2014. 111(32): p. 11679-11684.
3. Boudsocq, F., et al., *Sulfolobus solfataricus P2 DNA polymerase IV (Dpo4): an archaeal DinB-like DNA polymerase with lesion-bypass properties akin to eukaryotic polη.* Nucleic Acids Research, 2001. 29(22): p. 4607-4616.
4. Kent, S. B. H., *Total chemical synthesis of proteins.* Chemical Society Reviews, 2009. 38(2): p. 338-351.
5. Zheng, J.-S., et al., *Chemical synthesis of proteins using peptide hydrazides as thioester surrogates.* Nat Protocols, 2013. 8(12): p. 2483-2495.
6. Wan, Q. and S. J. Danishefsky, *Free-radical-based, specific desulfurization of cysteine: a powerful advance in the synthesis of polypeptides and glycopolypeptides.* Angew Chem Int Ed Engl, 2007. 46(48): p. 9248-52.
7. Fang, G.-M., et al., *Protein Chemical Synthesis by Ligation of Peptide Hydrazides.* Angewandte Chemie International Edition, 2011. 50(33): p. 7645-7649.
8. Huang, Y.-C., G.-M. Fang, and L. Liu, *Chemical synthesis of proteins using hydrazide intermediates.* National Science Review, 2016. 3(1): p. 107-116.
9. Dery, L., et al., *Accessing human selenoproteins through chemical protein synthesis.* Chemical Science, 2017.
10. Coin, I., *The depsipeptide method for solid-phase synthesis of difficult peptides.* J Pept Sci, 2010. 16(5): p. 223-30.
11. Liu, F., et al., *A Synthetic Route to Human Insulin Using Isoacyl Peptides.* Angewandte Chemie, 2014. 126(15): p. 4064-4068.
12. Raibaut, L., N. Ollivier, and O. Melnyk, *Sequential native peptide ligation strategies for total chemical protein synthesis.* Chem Soc Rev, 2012. 41(21): p. 7001-15.
13. Huang, Y. C., et al., *Synthesis of l- and d-Ubiquitin by One-Pot Ligation and Metal-Free Desulfurization.* Chemistry, 2016. 22(22): p. 7623-8.
14. Ling, H., et al., *Crystal structure of a Y-family DNA polymerase in action: a mechanism for error-prone and lesion-bypass replication.* Cell, 2001. 107(1): p. 91-102.
15. Jewett, M. C., et al., *In vitro integration of ribosomal RNA synthesis, ribosome assembly, and translation.* Mol Syst Biol, 2013. 9: p. 678.

16. Stemmer, W. P., et al., *Single-step assembly of a gene and entire plasmid from large numbers of oligodeoxyribonucleotides.* Gene, 1995. 164(1): p. 49-53.
17. Wochner, A., et al., *Ribozyme-catalyzed transcription of an active ribozyme.* Science, 2011. 332(6026): p. 209-12.
18. Williams, K. P., et al., *Bioactive and nuclease-resistant L-DNA ligand of vasopressin.* Proceedings of the National Academy of Sciences, 1997. 94(21): p. 11285-11290.
19. Yatime, L., et al., *Structural basis for the targeting of complement anaphylatoxin C5a using a mixed L-RNA/L-DNA aptamer.* Nat Commun, 2015. 6: p. 6481.
20. Sczepanski, J. T. and G. F. Joyce, *A cross-chiral RNA polymerase ribozyme.* Nature, 2014. 515(7527): p. 440-442.
21. Fiala, K. A. and Z. Suo, *Pre-steady-state kinetic studies of the fidelity of Sulfolobus solfataricus P2 DNA polymerase IV.* Biochemistry, 2004. 43(7): p. 2106-15.
22. Bode, J. W., *Emerging methods in amide- and peptide-bond formation.* Curr Opin Drug Discov Devel, 2006. 9(6): p. 765-75.
23. Englebretsen, D. R., B. Garnham, and P. F. Alewood, *A cassette ligation strategy with thioether replacement of three Gly-Gly peptide bonds: total chemical synthesis of the 101 residue protein early pregnancy factor [psi(CH (2)S)28-29,56-57,76-77].* J Org Chem, 2002. 67(17): p. 5883-90.
24. Zeng, W., et al., *Assembly of synthetic peptide vaccines by chemoselective ligation of epitopes: influence of different chemical linkages and epitope orientations on biological activity.* Vaccine, 2001. 19(28-29): p. 3843-52.
25. Pinheiro, V. B., et al., *Synthetic genetic polymers capable of heredity and evolution.* Science, 2012. 336 (6079): p. 341-4.
26. Larsen, A. C., et al., *A general strategy for expanding polymerase function by droplet microfluidics.* Nat Commun, 2016. 7: p. 11235.
27. Huang, Y.-C., et al., *Accelerated Fmoc solid-phase synthesis of peptides with aggregation-disrupting backbones.* Organic & Biomolecular Chemistry, 2015. 13(5): p. 1500-1506.
28. Huang, Y.-C., et al., *Facile synthesis of C-terminal peptide hydrazide and thioester of NY-ESO-1 (A39 A68) from an Fmoc-hydrazine 2-chlorotrityl chloride resin.* Tetrahedron, 2014. 70: p. 2951-2955.

The invention claimed is:

1. A method for replicating a minor-image nucleic acid, comprising: carrying out a reaction in the presence of a mirror-image nucleic acid polymerase, a mirror-image nucleic acid template, a mirror-image nucleic acid primer, and mirror-image dNTPs/rNTPs to obtain the mirror-image nucleic acid, wherein said mirror-image nucleic acid polymerase is in a D-form and selected from the group consisting of ASFV pol X of SEQ ID NO: 17 and a Dpo4 protein of *Sulfolobus solfataricus* which comprises mutations C31S, S86A, N123A, S207A and S313A and methionines Met1, Met76, Met89, Met157, Met216 and Met251 replaced with norleucine.

2. The method according to claim 1, wherein the mirror-image nucleic acid, the mirror-image nucleic acid template, the mirror-image nucleic acid primer, and the mirror-image dNTPs/rNTPs are in L-form.

3. The method according claim 1, wherein the mirror-image nucleic acid is L-DNA.

4. The method according to claim 1, wherein the reaction is a polymerase chain reaction.

5. The method according to claim 1, wherein the reaction is carried out in a buffer of 50 mM Tris-HCl, pH 7.5, 5 mM $MgCl_2$, 50 mM NaCl, 0.1 mM EDTA, 5 mM DTT, 10% glycerol, 3% DMSO and 0.1 mg/ml BSA.

6. A method for screening a mirror-image nucleic acid molecule, comprising:
   contacting a library of random mirror-image nucleic acid sequences with a target molecule under a condition that allows binding of the two;
   obtaining a mirror-image nucleic acid molecule that binds to the target molecule;
   and amplifying the mirror-image nucleic acid molecule that binds to the target molecule
   by mirror-image PCR using a mirror-image nucleic acid polymerase in D-form selected from the group consisting of ASFV pol X as set forth in SEQ ID NO: 17 and a Dpo4 protein of *Sulfolobus solfataricus* which comprises mutations C31S, S86A, N123A, S207A and S313A and all methionines Met1, Met76, Met89, Met157, Met216 and Met251 replaced with norleucine.

7. The method according to claim 6, wherein after the library of random mirror-image nucleic acid sequences is contacted with the target molecule, a mirror-image nucleic acid molecule that does not bind to the target molecule is removed by washing to obtain the mirror-image nucleic acid molecule that binds to the target molecule.

8. The method according to claim 6, wherein the mirror-image nucleic acid molecule is L-DNA.

9. The method according to claim 6, wherein the mirror-image PCR is performed in a buffer of 50 mM Tris-HCl, pH 7.5, 5 mM $MgCl_2$, 50 mM NaCl, 0.1 mM EDTA, 5 mM DTT, 10% glycerol, 3% DMSO and 0.1 mg/ml BSA.

10. The method according to claim 1, wherein the Dpo4 protein of *Sulfolobus solfataricus* comprises a His6 tag.

\* \* \* \* \*

```
SEQUENCE LISTING

<160> NUMBER OF SEQ ID NOS: 47

<210> SEQ ID NO 1
<211> LENGTH: 12
<212> TYPE: DNA
<213> ORGANISM: Artificial Sequence
<220> FEATURE:
<223> OTHER INFORMATION: D-/L-primer12

<400> SEQUENCE: 1
actacgaacg cg                                                          12

<210> SEQ ID NO 2
<211> LENGTH: 12
<212> TYPE: DNA
<213> ORGANISM: Artificial Sequence
<220> FEATURE:
<223> OTHER INFORMATION: D-/L-FAM-primer12

<400> SEQUENCE: 2
actacgaacg cg                                                          12

<210> SEQ ID NO 3
<211> LENGTH: 18
<212> TYPE: DNA
<213> ORGANISM: Artificial Sequence
<220> FEATURE:
<223> OTHER INFORMATION: D-/L-template18

<400> SEQUENCE: 3
ctcagtcgcg ttcgtagt                                                    18

<210> SEQ ID NO 4
<211> LENGTH: 66
<212> TYPE: DNA
<213> ORGANISM: Artificial Sequence
<220> FEATURE:
<223> OTHER INFORMATION: D-/L-DNAzymeTemplate

<400> SEQUENCE: 4
tgtacagcca cttcaactaa ttgctcaact atggctgtag cacccgcgtt cgtagtatgc      60
aatgca                                                                 66
```

<210> SEQ ID NO 5
<211> LENGTH: 20
<212> TYPE: DNA
<213> ORGANISM: Artificial Sequence
<220> FEATURE:
<223> OTHER INFORMATION: Cy5-primer20

<400> SEQUENCE: 5
agtgcgatac tacgaacgcg                                          20

<210> SEQ ID NO 6
<211> LENGTH: 26
<212> TYPE: DNA
<213> ORGANISM: Artificial Sequence
<220> FEATURE:
<223> OTHER INFORMATION: template26

<400> SEQUENCE: 6
ctcagtcgcg ttcgtagtat cgcact                                   26

<210> SEQ ID NO 7
<211> LENGTH: 18
<212> TYPE: DNA
<213> ORGANISM: Artificial Sequence
<220> FEATURE:
<223> OTHER INFORMATION: template18A

<400> SEQUENCE: 7
ctcagacgcg ttcgtagt                                            18

<210> SEQ ID NO 8
<211> LENGTH: 18
<212> TYPE: DNA
<213> ORGANISM: Artificial Sequence
<220> FEATURE:
<223> OTHER INFORMATION: template18C

<400> SEQUENCE: 8
ctcagccgcg ttcgtagt                                            18

<210> SEQ ID NO 9
<211> LENGTH: 18
<212> TYPE: DNA
<213> ORGANISM: Artificial Sequence
<220> FEATURE:
<223> OTHER INFORMATION: template18G

<400> SEQUENCE: 9
ctcatgcgcg ttcgtagt                                            18

<210> SEQ ID NO 10
<211> LENGTH: 15
<212> TYPE: DNA
<213> ORGANISM: Artificial Sequence
<220> FEATURE:
<223> OTHER INFORMATION: L-primer15

<400> SEQUENCE: 10
gatcacagtg agtac                                               15

<210> SEQ ID NO 11
<211> LENGTH: 20
<212> TYPE: DNA
<213> ORGANISM: Artificial Sequence
<220> FEATURE:

```
<223> OTHER INFORMATION: L-template21

<400> SEQUENCE: 11
ctattgtact cactgtgatc                                              20

<210> SEQ ID NO 12
<211> LENGTH: 56
<212> TYPE: DNA
<213> ORGANISM: Artificial Sequence
<220> FEATURE:
<223> OTHER INFORMATION: DNAzyme marker

<400> SEQUENCE: 12
actacgaacg cgggtgctac agccatagtt gagcaattag ttgaagtggc tgtaca     56

<210> SEQ ID NO 13
<211> LENGTH: 27
<212> TYPE: DNA
<213> ORGANISM: Artificial Sequence
<220> FEATURE:
<223> OTHER INFORMATION: L-template27

<400> SEQUENCE: 13
cgcgctgtta tagggatacg gcaaaaa                                      27

<210> SEQ ID NO 14
<211> LENGTH: 11
<212> TYPE: DNA
<213> ORGANISM: Artificial Sequence
<220> FEATURE:
<223> OTHER INFORMATION: L-primer11

<400> SEQUENCE: 14
cgcgctgtta t                                                       11

<210> SEQ ID NO 15
<211> LENGTH: 11
<212> TYPE: DNA
<213> ORGANISM: Artificial Sequence
<220> FEATURE:
<223> OTHER INFORMATION: L-FAM-primer11

<400> SEQUENCE: 15
cgcgctgtta t                                                       11

<210> SEQ ID NO 16
<211> LENGTH: 11
<212> TYPE: DNA
<213> ORGANISM: Artificial Sequence
<220> FEATURE:
<223> OTHER INFORMATION: L-reverse11

<400> SEQUENCE: 16
gccgtatccc t                                                       11

<210> SEQ ID NO 17
<211> LENGTH: 174
<212> TYPE: PRT
<213> ORGANISM: Artificial Sequence
<220> FEATURE:
<223> OTHER INFORMATION: ASFV pol X

<400> SEQUENCE: 17

Met Leu Thr Leu Ile Gln Gly Lys Lys Ile Val Asn His Leu Arg Ser
1               5                   10                  15
```

```
Arg Leu Ala Phe Glu Tyr Asn Gly Gln Leu Ile Lys Ile Leu Ser Lys
             20                  25                  30
Asn Ile Val Ala Val Gly Ser Leu Arg Arg Glu Glu Lys Met Leu Asn
         35                  40                  45
Asp Val Asp Leu Leu Ile Ile Val Pro Glu Lys Lys Leu Leu Lys His
     50                  55                  60
Val Leu Pro Asn Ile Arg Ile Lys Gly Leu Ser Phe Ser Val Lys Val
 65                  70                  75                  80
Cys Gly Glu Arg Lys Cys Val Leu Phe Ile Glu Trp Glu Lys Lys Thr
                 85                  90                  95
Tyr Gln Leu Asp Leu Phe Thr Ala Leu Ala Glu Glu Lys Pro Tyr Ala
            100                 105                 110
Ile Phe His Phe Thr Gly Pro Val Ser Tyr Leu Ile Arg Ile Arg Ala
        115                 120                 125
Ala Leu Lys Lys Lys Asn Tyr Lys Leu Asn Gln Tyr Gly Leu Phe Lys
    130                 135                 140
Asn Gln Thr Leu Val Pro Leu Lys Ile Thr Thr Glu Lys Glu Leu Ile
145                 150                 155                 160
Lys Glu Leu Gly Phe Thr Tyr Arg Ile Pro Lys Lys Arg Leu
                165                 170

<210> SEQ ID NO 18
<211> LENGTH: 525
<212> TYPE: DNA
<213> ORGANISM: Artificial Sequence
<220> FEATURE:
<223> OTHER INFORMATION: ASFV pol X

<400> SEQUENCE: 18
atgttaacgc ttattcaagg aaaaaaaatt gtaaatcact tacgttcccg acttgcgttt      60
gaatataatg gacaacttat aaaaatttta tcaaaaaaca tcgttgctgt tggtagttta     120
agacgcgaag agaaaatgct taatgacgtg gatcttctta ttattgttcc agaaaaaaaa     180
cttttaaaac acgtcctgcc caacattcgc ataaagggtc tttcttttc tgtaaaagtc      240 tgcggagaac gaaagtgtgt acttttat gaatgggaaa aaaagacgta tcaacttgat      300 cttttacgg ctttagccga ggaaaaacca tacgcaatat ttcattttac gggtcccgtt      360
tcttatctaa taagaattcg agccgcgtta aaaaaaaaga attataagct aaatcagtat     420
ggattattta aaaatcaaac tttagtacct ctaaaaatca ctactgaaaa agaacttatt     480
aaagaattag gatttacgta tcgcatacct aagaaacgtt tataa                    525

<210> SEQ ID NO 19
<211> LENGTH: 17
<212> TYPE: PRT
<213> ORGANISM: Artificial Sequence
<220> FEATURE:
<223> OTHER INFORMATION: segment of ASFV pol X

<400> SEQUENCE: 19

Glu Glu Lys Met Leu Asn Asp Val Asp Leu Leu Ile Ile Val Pro Glu
  1               5                  10                  15
Lys

<210> SEQ ID NO 20
<211> LENGTH: 21
<212> TYPE: PRT
<213> ORGANISM: Artificial Sequence
<220> FEATURE:
```

-continued

```
<223> OTHER INFORMATION: segment of ASFV pol X

<400> SEQUENCE: 20

His Val Leu Pro Asn Ile Arg Ile Lys Gly Leu Ser Phe Ser Val Lys
1               5                   10                  15

Val Cys Gly Glu Arg
            20

<210> SEQ ID NO 21
<211> LENGTH: 10
<212> TYPE: PRT
<213> ORGANISM: Artificial Sequence
<220> FEATURE:
<223> OTHER INFORMATION: segment of ASFV pol X

<400> SEQUENCE: 21

Lys Cys Val Leu Phe Ile Glu Trp Glu Lys
1               5                   10

<210> SEQ ID NO 22
<211> LENGTH: 14
<212> TYPE: PRT
<213> ORGANISM: Artificial Sequence
<220> FEATURE:
<223> OTHER INFORMATION: segment of ASFV pol X

<400> SEQUENCE: 22

Lys Lys Thr Tyr Gln Leu Asp Leu Phe Thr Ala Leu Ala Glu
1               5                   10

<210> SEQ ID NO 23
<211> LENGTH: 11
<212> TYPE: PRT
<213> ORGANISM: Artificial Sequence
<220> FEATURE:
<223> OTHER INFORMATION: segment of ASFV pol X

<400> SEQUENCE: 23

Lys Leu Leu Lys His Val Leu Pro Asn Ile Arg
1               5                   10

<210> SEQ ID NO 24
<211> LENGTH: 31
<212> TYPE: PRT
<213> ORGANISM: Artificial Sequence
<220> FEATURE:
<223> OTHER INFORMATION: segment of ASFV pol X

<400> SEQUENCE: 24

Lys Thr Tyr Gln Leu Asp Leu Phe Thr Ala Leu Ala Glu Lys Pro
1               5                   10                  15

Tyr Ala Ile Phe His Phe Thr Gly Pro Val Ser Tyr Leu Ile Arg
            20                  25                  30

<210> SEQ ID NO 25
<211> LENGTH: 38
<212> TYPE: PRT
<213> ORGANISM: Artificial Sequence
<220> FEATURE:
<223> OTHER INFORMATION: segment of ASFV pol X

<400> SEQUENCE: 25

Leu Asn Gln Tyr Gly Leu Phe Lys Asn Gln Thr Leu Val Pro Leu Lys
1               5                   10                  15

Ile Thr Thr Glu Lys Glu Leu Ile Lys Glu Leu Gly Phe Thr Tyr Arg
```

```
                  20                  25                  30

Ile Pro Lys Lys Arg Leu
        35

<210> SEQ ID NO 26
<211> LENGTH: 28
<212> TYPE: PRT
<213> ORGANISM: Artificial Sequence
<220> FEATURE:
<223> OTHER INFORMATION: segment of ASFV p

```
<220> FEATURE:
<223> OTHER INFORMATION: 5s rRNA(rrfB)-F

<400> SEQUENCE: 31
tgcctggcgg cagtagcgc                                              19

<210> SEQ ID NO 32
<211> LENGTH: 25
<212> TYPE: DNA
<213> ORGANISM: Artificial Sequence
<220> FEATURE:
<223> OTHER INFORMATION: 5s rRNA(rrfB)-R

<400> SEQUENCE: 32
atgcctggca gttccctact ctcgc                                       25

<210> SEQ ID NO 33
<211> LENGTH: 39
<212> TYPE: DNA
<213> ORGANISM: Artificial Sequence
<220> FEATURE:
<223> OTHER INFORMATION: 16s rRNA(rrsC)-F

<400> SEQUENCE: 33
aaattgaaga gtttgatcat ggctcagatt gaacgctgg                        39

<210> SEQ ID NO 34
<211> LENGTH: 27
<212> TYPE: DNA
<213> ORGANISM: Artificial Sequence
<220> FEATURE:
<223> OTHER INFORMATION: 16s rRNA(rrsC)-R

<400> SEQUENCE: 34
taaggaggtg atccaaccgc aggttcc                                     27

<210> SEQ ID NO 35
<211> LENGTH: 33
<212> TYPE: DNA
<213> ORGANISM: Artificial Sequence
<220> FEATURE:
<223> OTHER INFORMATION: dpo4-F

<400> SEQUENCE: 35
atgattgttc ttttcgttga ttttgactac ttt                              33

<210> SEQ ID NO 36
<211> LENGTH: 31
<212> TYPE: DNA
<213> ORGANISM: Artificial Sequence
<220> FEATURE:
<223> OTHER INFORMATION: dpo4-R

<400> SEQUENCE: 36
agtatcgaag aacttgtcta atcctattgc t                                31

<210> SEQ ID NO 37
<211> LENGTH: 115
<212> TYPE: DNA
<213> ORGANISM: Artificial Sequence
<220> FEATURE:
<223> OTHER INFORMATION: tC19Z-F115

<400> SEQUENCE: 37
gtcattgaaa aaaaaagaca aatctgccct cagagcttga gaacatcttc ggatgcagag    60
```
gaggcagcct tcggtggcgc gatagcgcca acgttctcaa cagacaccca atact         115

<210> SEQ ID NO 38
<211> LENGTH: 113
<212> TYPE: DNA
<213> ORGANISM: Artificial Sequence
<220> FEATURE:
<223> OTHER INFORMATION: tC19Z-R113

<400> SEQUENCE: 38
ggagccgaag ctccggggat tatgacctgg gcgtgtctaa catcgccttt tcgtcaggtg     60
ttatccccac cgccgaagc gggagtattg ggtgtctgtt gagaacgttg gcg            113

<210> SEQ ID NO 39
<211> LENGTH: 59
<212> TYPE: DNA
<213> ORGANISM: Artificial Sequence
<220> FEATURE:
<223> OTHER INFORMATION: tC19Z-F1

<400> SEQUENCE: 39
agaggaggca gccttcggtg gcgcgatagc gccaacgttc tcaacagaca cccaatact     59

<210> SEQ ID NO 40
<211> LENGTH: 59
<212> TYPE: DNA
<213> ORGANISM: Artificial Sequence
<220> FEATURE:
<223> OTHER INFORMATION: tC19Z-R1

<400> SEQUENCE: 40
caggtgttat ccccacccgc cgaagcggga gtattgggtg tctgttgaga acgttggcg    59

<210> SEQ ID NO 41
<211> LENGTH: 59
<212> TYPE: DNA
<213> ORGANISM: Artificial Sequence
<220> FEATURE:
<223> OTHER INFORMATION: tC19Z-F2

<400> SEQUENCE: 41
caaatctgcc ctcagagctt gagaacatct tcggatgcag aggaggcagc cttcggtgg    59

<210> SEQ ID NO 42
<211> LENGTH: 59
<212> TYPE: DNA
<213> ORGANISM: Artificial Sequence
<220> FEATURE:
<223> OTHER INFORMATION: tC19Z-R2

<400> SEQUENCE: 42
attatgacct gggcgtgtct aacatcgcct tttcgtcagg tgttatcccc acccgccga    59

<210> SEQ ID NO 43
<211> LENGTH: 51
<212> TYPE: DNA
<213> ORGANISM: Artificial Sequence
<220> FEATURE:
<223> OTHER INFORMATION: tC19Z-F3

<400> SEQUENCE: 43
gtcattgaaa aaaaaagaca aatctgccct cagagcttga gaacatcttc g             51

<210> SEQ ID NO 44
<211> LENGTH: 47

<212> TYPE: DNA
<213> ORGANISM: Artificial Sequence
<220> FEATURE:
<223> OTHER INFORMATION: tC19Z-R3

<400> SEQUENCE: 44
ggagccgaag ctccggggat tatgacctgg gcgtgtctaa catcgcc                47

<210> SEQ ID NO 45
<211> LENGTH: 352
<212> TYPE: PRT
<213> ORGANISM: Artificial Sequence
<220> FEATURE:
<223> OTHER INFORMATION: WT-Dpo4 amino acid sequence

<400> SEQUENCE: 45

```
Met Ile Val Leu Phe Val Asp Phe Asp Tyr Phe Tyr Ala Gln Val Glu
1               5                   10                  15

Glu Val Leu Asn Pro Ser Leu Lys Gly Lys Pro Val Val Val Cys Val
            20                  25                  30

Phe Ser Gly Arg Phe Glu Asp Ser Gly Ala Val Ala Thr Ala Asn Tyr
        35                  40                  45

Glu Ala Arg Lys Phe Gly Val Lys Ala Gly Ile Pro Ile Val Glu Ala
    50                  55                  60

Lys Lys Ile Leu Pro Asn Ala Val Tyr Leu Pro Met Arg Lys Glu Val
65                  70                  75                  80

Tyr Gln Gln Val Ser Ser Arg Ile Met Asn Leu Leu Arg Glu Tyr Ser
                85                  90                  95

Glu Lys Ile Glu Ile Ala Ser Ile Asp Glu Ala Tyr Leu Asp Ile Ser
            100                 105                 110

Asp Lys Val Arg Asp Tyr Arg Glu Ala Tyr Asn Leu Gly Leu Glu Ile
        115                 120                 125

Lys Asn Lys Ile Leu Glu Lys Glu Lys Ile Thr Val Thr Val Gly Ile
    130                 135                 140

Ser Lys Asn Lys Val Phe Ala Lys Ile Ala Ala Asp Met Ala Lys Pro
145                 150                 155                 160

Asn Gly Ile Lys Val Ile Asp Asp Glu Glu Val Lys Arg Leu Ile Arg
                165                 170                 175

Glu Leu Asp Ile Ala Asp Val Pro Gly Ile Gly Asn Ile Thr Ala Glu
            180                 185                 190

Lys Leu Lys Lys Leu Gly Ile Asn Lys Leu Val Asp Thr Leu Ser Ile
        195                 200                 205

Glu Phe Asp Lys Leu Lys Gly Met Ile Gly Glu Ala Lys Ala Lys Tyr
    210                 215                 220

Leu Ile Ser Leu Ala Arg Asp Glu Tyr Asn Glu Pro Ile Arg Thr Arg
225                 230                 235                 240

Val Arg Lys Ser Ile Gly Arg Ile Val Thr Met Lys Arg Asn Ser Arg
                245                 250                 255

Asn Leu Glu Glu Ile Lys Pro Tyr Leu Phe Arg Ala Ile Glu Glu Ser
            260                 265                 270

Tyr Tyr Lys Leu Asp Lys Arg Ile Pro Lys Ala Ile His Val Val Ala
        275                 280                 285

Val Thr Glu Asp Leu Asp Ile Val Ser Arg Gly Arg Thr Phe Pro His
    290                 295                 300

Gly Ile Ser Lys Glu Thr Ala Tyr Ser Glu Ser Val Lys Leu Leu Gln
305                 310                 315                 320
```

```
Lys Ile Leu Glu Glu Asp Glu Arg Lys Ile Arg Arg Ile Gly Val Arg
                325                 330                 335

Phe Ser Lys Phe Ile Glu Ala Ile Gly Leu Asp Lys Phe Phe Asp Thr
            340                 345                 350

<210> SEQ ID NO 46
<211> LENGTH: 358
<212> TYPE: PRT
<213> ORGANISM: Artificial Sequence
<220> FEATURE:
<223> OTHER INFORMATION: synthetic Dpo4 (with S86C, N123A, S207 A, S313A
      and C31S.)
<220> FEATURE:
<221> NAME/KEY: misc_feature
<222> LOCATION: (1)..(358)
<223> OTHER INFORMATION: D-amino acids
<220> FEATURE:
<221> NAME/KEY: misc_feature
<222> LOCATION: (7)..(7)
<223> OTHER INFORMATION: Xaa = norleucine
<220> FEATURE:
<221> NAME/KEY: misc_feature
<222> LOCATION: (82)..(82)
<223> OTHER INFORMATION: Xaa = norleucine
<220> FEATURE:
<221> NAME/KEY: misc_feature
<222> LOCATION: (95)..(95)
<223> OTHER INFORMATION: Xaa = norleucine
<220> FEATURE:
<221> NAME/KEY: misc_feature
<222> LOCATION: (163)..(163)
<223> OTHER INFORMATION: Xaa = norleucine
<220> FEATURE:
<221> NAME/KEY: misc_feature
<222> LOCATION: (222)..(222)
<223> OTHER INFORMATION: Xaa = norleucine
<220> FEATURE:
<221> NAME/KEY: misc_feature
<222> LOCATION: (257)..(257)
<223> OTHER INFORMATION: Xaa = norleucine

<400> SEQUENCE: 46

His His His His His His Xaa Ile Val Leu Phe Val Asp Phe Asp Tyr
1               5                   10                  15

Phe Tyr Ala Gln Val Glu Glu Val Leu Asn Pro Ser Leu Lys Gly Lys
            20                  25                  30

Pro Val Val Ser Val Phe Ser Gly Arg Phe Glu Asp Ser Gly Ala
        35                  40                  45

Val Ala Thr Ala Asn Tyr Glu Ala Arg Lys Phe Gly Val Lys Ala Gly
    50                  55                  60

Ile Pro Ile Val Glu Ala Lys Lys Ile Leu Pro Asn Ala Val Tyr Leu
65                  70                  75                  80

Pro Xaa Arg Lys Glu Val Tyr Gln Gln Val Ser Cys Arg Ile Xaa Asn
            85                  90                  95

Leu Leu Arg Glu Tyr Ser Glu Lys Ile Glu Ile Ala Ser Ile Asp Glu
            100                 105                 110

Ala Tyr Leu Asp Ile Ser Asp Lys Val Arg Asp Tyr Arg Glu Ala Tyr
        115                 120                 125

Ala Leu Gly Leu Glu Ile Lys Asn Lys Ile Leu Glu Lys Glu Lys Ile
    130                 135                 140

Thr Val Thr Val Gly Ile Ser Lys Asn Lys Val Phe Ala Lys Ile Ala
145                 150                 155                 160

Ala Asp Xaa Ala Lys Pro Asn Gly Ile Lys Val Ile Asp Asp Glu Glu
            165                 170                 175

Val Lys Arg Leu Ile Arg Glu Leu Asp Ile Ala Asp Val Pro Gly Ile
```

```
                    180                 185                 190
Gly Asn Ile Thr Ala Glu Lys Leu Lys Lys Leu Gly Ile Asn Lys Leu
                195                 200                 205

Val Asp Thr Leu Ala Ile Glu Phe Asp Lys Leu Lys Gly Xaa Ile Gly
            210                 215                 220

Glu Ala Lys Ala Lys Tyr Leu Ile Ser Leu Ala Arg Asp Glu Tyr Asn
225                 230                 235                 240

Glu Pro Ile Arg Thr Arg Val Arg Lys Ser Ile Gly Arg Ile Val Thr
                245                 250                 255

Xaa Lys Arg Asn Ser Arg Asn Leu Glu Glu Ile Lys Pro Tyr Leu Phe
            260                 265                 270

Arg Ala Ile Glu Glu Ser Tyr Tyr Lys Leu Asp Lys Arg Ile Pro Lys
        275                 280                 285

Ala Ile His Val Val Ala Val Thr Glu Asp Leu Asp Ile Val Ser Arg
    290                 295                 300

Gly Arg Thr Phe Pro His Gly Ile Ser Lys Glu Thr Ala Tyr Ala Glu
305                 310                 315                 320

Ser Val Lys Leu Leu Gln Lys Ile Leu Glu Glu Asp Glu Arg Lys Ile
                325                 330                 335

Arg Arg Ile Gly Val Arg Phe Ser Lys Phe Ile Glu Ala Ile Gly Leu
            340                 345                 350

Asp Lys Phe Phe Asp Thr
            355

<210> SEQ ID NO 47
<211> LENGTH: 358
<212> TYPE: PRT
<213> ORGANISM: Artificial Sequence
<220> FEATURE:
<223> OTHER INFORMATION: synthetic Dpo4 (with S86A, N123A, S207 A, S313A
      and C31S.)
<220> FEATURE:
<221> NAME/KEY: misc_feature
<222> LOCATION: (1)..(358)
<223> OTHER INFORMATION: L-amino acids
<220> FEATURE:
<221> NAME/KEY: misc_feature
<222> LOCATION: (7)..(7)
<223> OTHER INFORMATION: Xaa = norleucine
<220> FEATURE:
<221> NAME/KEY: misc_feature
<222> LOCATION: (82)..(82)
<223> OTHER INFORMATION: Xaa = norleucine
<220> FEATURE:
<221> NAME/KEY: misc_feature
<222> LOCATION: (95)..(95)
<223> OTHER INFORMATION: Xaa = norleucine
<220> FEATURE:
<221> NAME/KEY: misc_feature
<222> LOCATION: (163)..(163)
<223> OTHER INFORMATION: Xaa = norleucine
<220> FEATURE:
<221> NAME/KEY: misc_feature
<222> LOCATION: (222)..(222)
<223> OTHER INFORMATION: Xaa = norleucine
<220> FEATURE:
<221> NAME/KEY: misc_feature
<222> LOCATION: (257)..(257)
<223> OTHER INFORMATION: Xaa = norleucine

<400> SEQUENCE: 47

His His His His His Xaa Ile Val Leu Phe Val Asp Phe Asp Tyr
1               5                   10                  15

Phe Tyr Ala Gln Val Glu Glu Val Leu Asn Pro Ser Leu Lys Gly Lys
                20                  25                  30
```

-continued

```
Pro Val Val Val Ser Val Phe Ser Gly Arg Phe Glu Asp Ser Gly Ala
             35                  40                  45
Val Ala Thr Ala Asn Tyr Glu Ala Arg Lys Phe Gly Val Lys Ala Gly
             50                  55                  60
Ile Pro Ile Val Glu Ala Lys Lys Ile Leu Pro Asn Ala Val Tyr Leu
65                   70                  75                   80
Pro Xaa Arg Lys Glu Val Tyr Gln Gln Val Ser Ala Arg Ile Xaa Asn
             85                  90                  95
Leu Leu Arg Glu Tyr Ser Glu Lys Ile Glu Ile Ala Ser Ile Asp Glu
             100                 105                 110
Ala Tyr Leu Asp Ile Ser Asp Lys Val Arg Asp Tyr Arg Glu Ala Tyr
             115                 120                 125
Ala Leu Gly Leu Glu Ile Lys Asn Lys Ile Leu Glu Lys Glu Lys Ile
             130                 135                 140
Thr Val Thr Val Gly Ile Ser Lys Asn Lys Val Phe Ala Lys Ile Ala
145                 150                  155                 160
Ala Asp Xaa Ala Lys Pro Asn Gly Ile Lys Val Ile Asp Asp Glu Glu
             165                 170                 175
Val Lys Arg Leu Ile Arg Glu Leu Asp Ile Ala Asp Val Pro Gly Ile
             180                 185                 190
Gly Asn Ile Thr Ala Glu Lys Leu Lys Lys Leu Gly Ile Asn Lys Leu
             195                 200                 205
Val Asp Thr Leu Ala Ile Glu Phe Asp Lys Leu Lys Gly Xaa Ile Gly
             210                 215                 220
Glu Ala Lys Ala Lys Tyr Leu Ile Ser Leu Ala Arg Asp Glu Tyr Asn
225                 230                  235                 240
Glu Pro Ile Arg Thr Arg Val Arg Lys Ser Ile Gly Arg Ile Val Thr
             245                 250                 255
Xaa Lys Arg Asn Ser Arg Asn Leu Glu Glu Ile Lys Pro Tyr Leu Phe
             260                 265                 270
Arg Ala Ile Glu Glu Ser Tyr Tyr Lys Leu Asp Lys Arg Ile Pro Lys
             275                 280                 285
Ala Ile His Val Val Ala Val Thr Glu Asp Leu Asp Ile Val Ser Arg
             290                 295                 300
Gly Arg Thr Phe Pro His Gly Ile Ser Lys Glu Thr Ala Tyr Ala Glu
305                 310                  315                 320
Ser Val Lys Leu Leu Gln Lys Ile Leu Glu Glu Asp Glu Arg Lys Ile
             325                 330                 335
Arg Arg Ile Gly Val Arg Phe Ser Lys Phe Ile Glu Ala Ile Gly Leu
             340                 345                 350
Asp Lys Phe Phe Asp Thr
             355
```